US009827324B2

(12) United States Patent
Pipkin et al.

(10) Patent No.: US 9,827,324 B2
(45) Date of Patent: *Nov. 28, 2017

(54) INHALANT FORMULATION CONTAINING SULFOALKYL ETHER CYCLODEXTRIN AND CORTICOSTEROID

(75) Inventors: James D. Pipkin, Lawrence, KS (US); Rupert O. Zimmerer, Lawrence, KS (US); Diane O. Thompson, Overland Park, KS (US); Gerold L. Mosher, Kansas City, MO (US)

(73) Assignee: Cydex Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/586,380

(22) Filed: Aug. 15, 2012

(65) Prior Publication Data

US 2013/0059826 A1    Mar. 7, 2013

Related U.S. Application Data

(63) Continuation of application No. 13/015,959, filed on Jan. 28, 2011, now abandoned, which is a continuation of application No. 11/613,187, filed on Dec. 19, 2006, now abandoned, which is a continuation-in-part of application No. 11/479,979, filed on Jun. 30, 2006, now abandoned, which is a continuation-in-part of application No. PCT/US2005/000082, filed on Dec. 31, 2004.

(60) Provisional application No. 60/533,628, filed on Dec. 31, 2003.

(51) Int. Cl.
| | |
|---|---|
| *A61K 9/00* | (2006.01) |
| *A61K 31/58* | (2006.01) |
| *C08B 37/16* | (2006.01) |
| *A61K 47/48* | (2006.01) |
| *A61K 31/573* | (2006.01) |
| *A61K 31/724* | (2006.01) |
| *A61K 45/06* | (2006.01) |
| *A61K 47/40* | (2006.01) |
| *C08L 5/16* | (2006.01) |
| *B82Y 5/00* | (2011.01) |

(52) U.S. Cl.
CPC ...... *A61K 47/48092* (2013.01); *A61K 9/0078* (2013.01); *A61K 31/573* (2013.01); *A61K 31/58* (2013.01); *A61K 31/724* (2013.01); *A61K 45/06* (2013.01); *A61K 47/40* (2013.01); *A61K 47/48969* (2013.01); *B82Y 5/00* (2013.01); *C08B 37/0015* (2013.01); *C08L 5/16* (2013.01)

(58) Field of Classification Search
CPC .... A61K 9/0078; A61K 31/573; A61K 31/58; A61K 31/724; A61K 45/06; A61K 47/40; A61K 47/48969; C08B 37/0015; C08L 5/16; B82Y 5/00

See application file for complete search history.

(56) References Cited

U.S. PATENT DOCUMENTS

| | | | |
|---|---|---|---|
| 3,008,875 A | 11/1961 | Dale | |
| 3,219,533 A | 11/1965 | Mullins | |
| 3,426,011 A | 2/1969 | Parmerter et al. | |
| 4,383,992 A | 5/1983 | Lipari | |
| 4,642,305 A | 2/1987 | Johansson et al. | |
| 5,024,998 A | 6/1991 | Bodor | |
| 5,134,127 A * | 7/1992 | Stella et al. | 514/58 |
| 5,164,194 A | 11/1992 | Hettche | |
| 5,192,528 A | 3/1993 | Radhakrishnan et al. | |
| 5,216,151 A | 6/1993 | Murakami | |
| 5,318,780 A | 6/1994 | Viegas et al. | |
| 5,324,718 A | 6/1994 | Loftsson | |
| 5,376,645 A * | 12/1994 | Stella et al. | 514/58 |
| 5,472,954 A | 12/1995 | Loftsson | |
| 5,510,339 A | 4/1996 | Gleich et al. | |
| 5,525,623 A | 6/1996 | Spear et al. | |
| 5,556,964 A | 9/1996 | Hofstraat et al. | |
| 5,576,311 A | 11/1996 | Guy | |

(Continued)

FOREIGN PATENT DOCUMENTS

| | | |
|---|---|---|
| AU | 2006200277 | 2/2006 |
| CN | 101199855 | 6/2008 |

(Continued)

OTHER PUBLICATIONS

Adjei et al., Feb. 1992, Bioavailablity of leuprolide acetate following nasal and inhalation delivery to rats and healthy humans, Pharm. Res. 9(2):244-249.
AstraZeneca, Aug. 4, 2000, Pulmicort Respules (budesonide inhalation suspension 0.25 mg and 0.5 mg, package insert for Pulmicort Respules, 17 pp.
Bandi et al., 2004, Preparation of budesonide-and indomethacin-hydroxypropyl-β-cyclodextrin (HPBCD) complexes using a single-step, organic-solvent-free supercritical fluid process, European Journal of Pharmaceutical Sciences, 23(2):159-168.
Barry et al., Aug. 1998, The output of budesonide from nebulizers; J. Allergy Clin. Immunol., 102:321-322.
Bosco et al., A Submicron Suspension of Budesonide Improves the Mass of ICS Delivered During Early Nebulization , 1 pp.
Budesonide, in Martindale: The Complete Drug Reference, pp. 1034-1035.

(Continued)

*Primary Examiner* — John Pak
*Assistant Examiner* — Nathan W Schlientz
(74) *Attorney, Agent, or Firm* — Knobbe, Martens, Olson & Bear LLP

(57) ABSTRACT

An inhalable formulation containing SAE-CD and corticosteroid is provided. The formulation is adapted for administration to a subject by nebulization with any known nebulizer. The formulation can be included in a kit. The formulation is administered as an aqueous solution, however, it can be stored as a dry powder, ready-to-use solution, or concentrated composition. The formulation is employed in an improved nebulization system for administering corticosteroid by inhalation. SAE-CD present in the formulation significantly enhances the chemical stability of budesonide. A method of administering the formulation by inhalation is provided. The formulation can also be administered by conventional nasal delivery apparatus.

3 Claims, 12 Drawing Sheets

(56) References Cited

U.S. PATENT DOCUMENTS

| | | | |
|---|---|---|---|
| 5,576,645 A | 11/1996 | Farwell | |
| 5,587,175 A | 12/1996 | Viegas et al. | |
| 5,631,267 A | 5/1997 | Gleich et al. | |
| 5,654,276 A | 8/1997 | Barrett et al. | |
| 5,668,110 A | 9/1997 | Barrett et al. | |
| 5,677,280 A | 10/1997 | Barrett et al. | |
| 5,683,983 A | 11/1997 | Barrett et al. | |
| 5,691,336 A | 11/1997 | Dorn et al. | |
| 5,750,549 A | 5/1998 | Caldwell et al. | |
| 5,756,483 A | 5/1998 | Merkus | |
| 5,780,467 A | 7/1998 | Dorn et al. | |
| 5,837,713 A | 11/1998 | Gleich | |
| 5,840,881 A | 11/1998 | Uda et al. | |
| 5,855,916 A | 1/1999 | Chiesi et al. | |
| 5,874,418 A * | 2/1999 | Stella et al. | 514/58 |
| 5,877,191 A | 3/1999 | Caldwell et al. | |
| 5,914,122 A | 6/1999 | Otterbeck et al. | |
| 5,929,094 A | 7/1999 | Durette et al. | |
| 5,935,941 A | 8/1999 | Pitha | |
| 5,942,251 A | 8/1999 | Merkus | |
| 5,955,454 A | 9/1999 | Merkus | |
| 5,958,443 A | 9/1999 | Viegas et al. | |
| 5,977,070 A | 11/1999 | Piazza et al. | |
| 6,027,714 A | 2/2000 | Trofast | |
| 6,046,177 A | 4/2000 | Stella et al. | |
| 6,071,910 A | 6/2000 | Gleich et al. | |
| 6,136,603 A | 10/2000 | Dean et al. | |
| 6,153,746 A | 11/2000 | Shah et al. | |
| 6,218,375 B1 | 4/2001 | Raghavan et al. | |
| 6,267,985 B1 | 7/2001 | Chen et al. | |
| 6,284,287 B1 | 9/2001 | Sarlikiotis et al. | |
| 6,287,540 B1 | 9/2001 | Trofast | |
| 6,291,445 B1 | 9/2001 | Nilsson et al. | |
| 6,297,227 B1 | 10/2001 | Johnson | |
| 6,346,523 B1 | 2/2002 | Bisrat et al. | |
| 6,358,935 B1 | 3/2002 | Beck et al. | |
| 6,407,079 B1 | 6/2002 | Muller et al. | |
| 6,436,902 B1 | 8/2002 | Backstrom et al. | |
| 6,468,994 B1 | 10/2002 | Bisrat et al. | |
| 6,479,467 B1 | 11/2002 | Buchanan et al. | |
| 6,509,323 B1 | 1/2003 | Davis et al. | |
| 6,518,239 B1 | 2/2003 | Kuo et al. | |
| 6,598,603 B1 | 7/2003 | Andersson et al. | |
| 6,610,671 B2 | 8/2003 | Buchanan et al. | |
| 6,660,804 B1 | 12/2003 | Weltrowski et al. | |
| 6,686,346 B2 | 2/2004 | Nilsson et al. | |
| 6,761,903 B2 | 7/2004 | Chen et al. | |
| 6,899,099 B2 | 5/2005 | Andersson et al. | |
| 6,962,151 B1 | 11/2005 | Knoch et al. | |
| 6,969,706 B1 | 11/2005 | Chang | |
| 6,986,904 B2 | 1/2006 | Nilsson et al. | |
| 7,034,013 B2 | 4/2006 | Thompson et al. | |
| 7,115,586 B2 | 10/2006 | Loftsson | |
| 7,128,928 B2 | 10/2006 | Singh et al. | |
| 7,625,878 B2 | 12/2009 | Stella et al. | |
| 7,829,114 B2 | 11/2010 | Thompson et al. | |
| 7,893,040 B2 | 2/2011 | Loftsson et al. | |
| 8,114,438 B2 | 2/2012 | Pipkin et al. | |
| 2002/0022629 A1 | 2/2002 | Cagle et al. | |
| 2002/0035264 A1 | 3/2002 | Kararli et al. | |
| 2002/0055496 A1 | 5/2002 | McCoy et al. | |
| 2002/0128468 A1 | 9/2002 | Buchanan et al. | |
| 2002/0150616 A1 | 10/2002 | Vandecruys | |
| 2002/0151597 A1 | 10/2002 | Banerjee et al. | |
| 2002/0183293 A1* | 12/2002 | Banerjee et al. | 514/171 |
| 2002/0198174 A1 | 12/2002 | Lyons | |
| 2003/0055023 A1 | 3/2003 | Rajewski et al. | |
| 2003/0069253 A1 | 4/2003 | Cagle et al. | |
| 2003/0091513 A1 | 5/2003 | Mohsen et al. | |
| 2003/0103864 A1 | 6/2003 | McAffer et al. | |
| 2003/0113367 A1 | 6/2003 | Penkler | |
| 2003/0129242 A1 | 7/2003 | Bosch et al. | |
| 2003/0143274 A1 | 7/2003 | Viegas et al. | |
| 2003/0175313 A1 | 9/2003 | Garrec et al. | |
| 2003/0194378 A1 | 10/2003 | Rogueda | |
| 2004/0045546 A1 | 3/2004 | Hirsh et al. | |
| 2004/0063663 A1 | 4/2004 | Buchanan et al. | |
| 2004/0091546 A1 | 5/2004 | Johnson et al. | |
| 2004/0106575 A1 | 6/2004 | Zhana et al. | |
| 2004/0109888 A1 | 6/2004 | Pun et al. | |
| 2004/0204394 A1 | 10/2004 | Minaskanian | |
| 2004/0220153 A1 | 11/2004 | Jost-Price et al. | |
| 2004/0224876 A1 | 11/2004 | Jost-Price et al. | |
| 2005/0048127 A1 | 3/2005 | Brown et al. | |
| 2005/0112199 A1 | 5/2005 | Padval et al. | |
| 2005/0119160 A1 | 6/2005 | Keith et al. | |
| 2005/0175546 A1 | 8/2005 | Sambuco et al. | |
| 2005/0186267 A1 | 8/2005 | Thompson et al. | |
| 2005/0222111 A1 | 10/2005 | Andersson et al. | |
| 2005/0234018 A1 | 10/2005 | Lyons et al. | |
| 2005/0244339 A1 | 11/2005 | Jauernig et al. | |
| 2005/0244472 A1 | 11/2005 | Hughes et al. | |
| 2005/0250737 A1 | 11/2005 | Hughes et al. | |
| 2006/0025391 A1 | 2/2006 | Lulla et al. | |
| 2006/0035874 A1 | 2/2006 | Lulla et al. | |
| 2006/0045850 A1 | 3/2006 | Namburi et al. | |
| 2006/0078505 A1 | 4/2006 | McAffer et al. | |
| 2006/0105045 A1 | 5/2006 | Buchanan et al. | |
| 2006/0110331 A1 | 5/2006 | Dang et al. | |
| 2006/0120967 A1 | 6/2006 | Namburi et al. | |
| 2006/0193783 A1 | 8/2006 | Bhowmick et al. | |
| 2006/0194840 A1 | 8/2006 | Gozal | |
| 2006/0258537 A1 | 11/2006 | Stella et al. | |
| 2006/0263350 A1 | 11/2006 | Lane | |
| 2007/0020196 A1 | 1/2007 | Pipkin et al. | |
| 2007/0020298 A1 | 1/2007 | Pipkin et al. | |
| 2007/0020299 A1 | 1/2007 | Pipkin et al. | |
| 2007/0020330 A1 | 1/2007 | Dang et al. | |
| 2007/0020336 A1 | 1/2007 | Loftsson | |
| 2007/0148192 A1 | 6/2007 | Laddha et al. | |
| 2007/0160542 A1 | 7/2007 | Hill | |
| 2007/0178049 A1 | 8/2007 | Hill | |
| 2007/0178050 A1 | 8/2007 | Hill | |
| 2007/0185066 A1 | 8/2007 | Hill | |
| 2007/0191323 A1 | 8/2007 | Hill et al. | |
| 2007/0191327 A1 | 8/2007 | Hill et al. | |
| 2007/0191599 A1 | 8/2007 | Hill et al. | |
| 2007/0197486 A1 | 8/2007 | Hill | |
| 2007/0197487 A1 | 8/2007 | Hill | |
| 2007/0202051 A1 | 8/2007 | Schuschnig | |
| 2007/0202054 A1 | 8/2007 | Pipkin et al. | |
| 2007/0249572 A1 | 10/2007 | Hill | |
| 2009/0253745 A1 | 10/2009 | Mata et al. | |
| 2011/0008325 A1 | 1/2011 | Pipkin et al. | |
| 2011/0123518 A1 | 5/2011 | Pipkin et al. | |
| 2011/0251157 A1 | 10/2011 | Pipkin et al. | |
| 2011/0281901 A1 | 11/2011 | Gupta | |
| 2013/0303498 A1 | 11/2013 | Pipkin et al. | |

FOREIGN PATENT DOCUMENTS

| | | |
|---|---|---|
| CN | 101273993 | 10/2008 |
| DE | 4207922 | 9/1993 |
| EP | 0 579 435 | 1/1994 |
| EP | 0 709 099 | 5/1996 |
| EP | 1 894 559 | 3/2008 |
| GB | 2109381 | 6/1983 |
| JP | 58225010 | 12/1983 |
| JP | 61221120 | 10/1986 |
| JP | 02-167228 | 6/1990 |
| RU | 2157214 | 10/2000 |
| RU | 2180217 | 3/2002 |
| WO | WO 91/04026 | 4/1991 |
| WO | WO 91/04984 | 4/1991 |
| WO | WO 91/11172 | 8/1991 |
| WO | WO 91/13100 | 9/1991 |
| WO | WO 94/02518 | 2/1994 |
| WO | WO 97/11090 | 3/1997 |
| WO | WO 98/18827 | 5/1998 |
| WO | WO 98/50077 | 11/1998 |
| WO | WO 99/42111 | 8/1999 |
| WO | WO 00/41704 | 7/2000 |
| WO | WO 01/85137 | 11/2001 |
| WO | WO 02/39993 | 5/2002 |

(56) References Cited

FOREIGN PATENT DOCUMENTS

| WO | WO 03/035030 | 5/2003 |
|---|---|---|
| WO | WO 03/070194 | 8/2003 |
| WO | WO 03/080079 | 10/2003 |
| WO | WO 2004/069280 | 8/2004 |
| WO | WO 2004/082590 | 9/2004 |
| WO | WO 2004/087043 | 10/2004 |
| WO | WO 2005/060945 | 7/2005 |
| WO | WO 2005/065435 | 7/2005 |
| WO | WO 2005/065649 | 7/2005 |
| WO | WO 2005/065651 | 7/2005 |
| WO | WO 2006/102494 | 9/2006 |
| WO | WO 2007/054974 | 5/2007 |
| WO | WO 2007/075798 | 7/2007 |
| WO | WO 2007/075799 | 7/2007 |
| WO | WO 2007/075800 | 7/2007 |
| WO | WO 2007/075801 | 7/2007 |
| WO | WO 2007/075859 | 7/2007 |
| WO | WO 2007/075963 | 7/2007 |
| WO | WO 2007/095339 | 8/2007 |
| WO | WO 2007/095341 | 8/2007 |
| WO | WO 2007/095342 | 8/2007 |
| WO | WO 2008/005692 | 1/2008 |
| WO | WO 2008/005802 | 1/2008 |
| WO | WO 2008/005819 | 1/2008 |

OTHER PUBLICATIONS

Challa et al., 2005, Cyclodextrins in drug delivery: an updated review, AAPS PharmaSciTech, 6(2) Article 43, E329-E357.
CyDex Announces Multiple Agreements: Cydex Press release Apr. 2002, 5(1):3.
CyDex, Inc., Aug. 8, 2007, Captisol-Enabled Budesonide Solution for Nebulization, http//www.cydexinc.com/captisol-enabledbudesonide.asp, 12 pp.
CyDex, Inc., Captisol: Sulfobutylether β-Cyclodextrin: Frequently Ased Questions, http://www.cydexinc.com, 14 pp.
CyDex, Inc., Oct. 31, 2004, Innovative Drug Delivery Technology for Enhanced Solubility and Stability, product brochure, 8 pp.
Evrard et al., 2004, Cyclodextrins as potential carrier in drug nebulization, Journal of Controlled Release, 96:403-410.
Flood et al., 2000, Characterization of inclusion complexes of betamethasone related steroids with cyclodextrins using high-performance liquid chromatography.; Journal of Chromatography, 903:49-65.
Friedrich et al., Dec. 7-9, 2005, Colloidal formulations to improve drug delivery by eFlow a new electronic nebuliser; Drug Delivery to the Lungs XVI Proceedings, pp. 125-128.
FrymaKoruma Dinex Vacuum Processing Unit for Liquids and Semi Solids, Romaco, 2005 Romaco Ag.
Gudmundsdottir et al., Dec. 2001, Intranasal administration of midazolam in a cyclodextrin based formulation: bioavailability and clinical evaluation in humans, Pharmazie, 56(12):963-966.
Hou, 2001, Kinetics and mechanisms of budesonide degradation in propylene glycol solutions; File 35: Dissertation Abs Online 186—Jul. 2007, 2 pp.
Ilangovan et al., 1993, Treatment of severe steroid dependent preschool asthma with nebulised budesonide suspension; Archives of Disease in Childhood, 68:356-359.
Jackson, 1995, Nebulised Budesonide Therapy in Asthma: A Scientific and Practical Review, Clinical Vision Ltd, Harwell, UK.
Jain et al.., 2001, Hygroscopicity, phase solubility and dissolution of variosubstituted sulfobutylether beta-cyclodextrins (SBE) and danazol-SBE inclusion complexes; International Journal of Pharmaceutics, 212:177-186.
Jauernig et al., 2004, Effects of the test set-up, formulation. and nebulizer type on aerodynamic droplet characteristics; Respiratory Drug Delivery IX, pp. 609-612.
Jauernig et al., Dec. 12, 2003, Assessment of the next generation impactor (NGI) for the use in the nebuliser CEN standard EN-13544-1, Drug Delivery to the Lungs XIV, 20 pp.
Jauernig et al., May 20-25, 2004, A novel budesonide formulation (BUDeFlow) to improve Asthma Treatment in babies using a new electronic inhaler, American Thoracic Society, Orlando Florida, 1 p.
Keller et al., Sep. 4-8, 2004, Prediction of the lung dose in young children by cascade impaction methods alternatively to the SAINT Model; European Respiratory Society Annual Congress, Glasgow, UK, 1 pp.
Keller, Jan. 30, 2003, The PARI eFlow: a sophisticated electronic nebuliser for improved pulmonary drug delivery; Pharmapack Conference Presentation, 22 pp.
Kinnarinen et al., 2002, The in vitro pulmonary deposition of a budesonid/γ-cyclodextrin inclusion complex, Journal of Inclusion Phenomena and Macrocyclic Chemistry, 44:97-100.
Knoch et al., Dec. 7, 2002, Testing of pharmaceutical aerosols generated by nebulizers: relevant definitions and methods; Symposium on Drug Inhalation Therapy, Tokyo, 17 pp.
Kraft et al., 2004, The Pharmacokinetics of Nebulized Nanocrystal Budsonide Suspension in Healthy Volunteers, J. Clin. Pharmacology, 44:67-72.
Lammers et al., 1971, Properties of cyclodextrins: Part VI. Water-soluble cyclodextrin-derivatives, Preparation and Analysis, Die Starke, 23(5):167-171.
Lammers et al., 1972, Properties of Cyclodextrins: Part VIII, Recueil, 91:733-742.
Lintz et al., Dec. 9-10, 2004, A novel formulation approach for improved nebulised drug delivery of poorly water soluble drugs; Drug Delivery to the Lungs XV, London, UK, 4 pp.
Liu et al., 1990, Beta-cyclodextrin/steroid complexation: effect of steroid structure on association equilibria; Pharmaceutical Research, 7(8):869-873.
Loftsson et al., 2005, Cyclodextrins in drug delivery; Expert Opin. Drug Deliv. 2(2):335-351.
Luangkhot et al., Dec. 11-12, 2000, Characterisation of salbutamol solution compared to budesonide suspensions consisting of submicron, and micrometer particles in the Pari LC Star and a new Pari Electronic nebuliser (eFlow); Delivery to the Lungs XI, London, 4 pp.
Luangkhot et al., Oct. 29-Nov. 2, 2000, Characterisation of salbutamol solution compared to budesonide suspensions consisting of submicron and micrometer particles in the PARI LC star and a PARI Electronic Nebuliser (eFlow) prototype; AAPS Annual Meeting, Indianapolis, 1 p.
MAP Pharmaceuticals, Inc., Unit Dose Budesonide (UDB), 2005, 2 pp.
Miles et al., Preformulation Studies on a Captisol-Enabled Budesonide Inhalation Solution; http://www.cydexinc.com; 1 pp.
Muller et al., 1985, Change of phase-solubility behavior by gamma-cyclodextrin derivatization; Pharmaceutical Research, pp. 309-310.
Muller et al., 1997, Budesonide microparticles for pulmonary delivery produced by supercritical carbon dioxide, Proceed. Int'l. Symp. Control. Rel. Bioact. Mater, 24:69-70.
Nakate et al., Mar. 2003, Improvement of pulmonary absorption of cyclopeptide FK224 in rats by co-formulating with Eur. J. Pharm. Biopharm., 55(2):147-154.
Nimbalkar et al., 2001, Activation of diacetyldapsone and a preliminary evaluation of a cyclodextrin-diacetyldapsone complex in cultured lung cells, Biotechnol, Appl. Biochem. 33:123-125.
Pinto et al., 1999, Beclomethasone/cyclodextrin inclusion complex for dry powder inhalation, S.T.P. Pharma. Sciences, 9(3):253-256 (abstract).
Qu et al., 2002, Sulfoalkyl ether β-cyclodextrin derivatives: synthesis and characterizations, J. Inclusion Phenom. Macro. Chem, 43:213-221.
Raposo et al., Nov. 6-10, 2005, Cyclodextrin nanoparticles loaded with cyclosporine A for inhalation; AAPS Annual Meeting, Nashville, TN, 1 p.
Reid et al., Apr. 1996, Linear growth of very young asthmatic children treated with high-dose nebulized budesonide; Acta Pediatrica: An International Journal of Pediatrics, 85(4):421-424.
Rhinocort—CMI, Aug. 6, 2007, APP Guide Online Consumer Medicine Information, http://appco.com.au/appguide/drug.asp?drug id=00071322&t=cmi Rhinocort-CMI; 6 pp.

(56) References Cited

OTHER PUBLICATIONS

Schoni, Inhalation of aerosols by children: an ongoing controversy; Swiss Medical Weekly, 3pp.

Schueepp et al., May 16-21, 2003, Assessment of an Electronic Inhaler (eFlow) with a Budesonide Solution Utilizing a Baby Cast Model Applying Different Breathing Patterns; American Thoracic Society 99th International Conference, 1 p.

Shao et al., 1994, Cyclodextrins as mucosal absorption promoters of insulin: III. Pulmonary route of delivery, Eur. J. Pharm, Biopharm. 40(5):283-288.

Shrewbury et al., Tolerability of a Novel Submicron Particle Formulation of Budesonide for Nebulized Delivery in Asthma; Presentation (PP), 1 p.

Skoner et al., Feb. 2000, Longitudinal growth in infants and young children treated with budesonide inhalation suspension for persistent asthma; J. Allergy Clin. Immunol., 105(2, part 1):259-268.

Skoner et al., Oct. 1999, Clinical use of nebulized budesonide inhalation suspension in a child with asthma; J Allergy Clin Immunology, 104(4, part 2):S210-S214.

Smaldone et al., 1998, In vitro determination of inhaled mass and particle distribution for budesonide nebulizing suspension; Journal of Aerosol Medicine, 11(2):113-125.

Srichana et al., 2001, Cyclodextrin as a potential drug carrier in salbutamol dry powder aerosols: the in-vitro deposition and toxicity studies of the complexes; Respiratory Medicine, 95:513-519.

Szefler, Oct. 1999, Pharmacodynamics and pharmacokinetics of budesonide: A new nebulized corticosteroid; J Allergy Clin Immunology, 104(4, part 2):S175-S183.

Vozone et al., 2002, Complexation of budesonide in cyclodextrins and particle aerodynamic characterization of the complex solid form for dry powder Inhalation, Journal of Inclusion Phenomena and Macrocyclic Chemistry, 44:111-115.

Waldrep et al., 1997, High dose cyclosporin A and budesonide-liposome aerosols, International Journal of Pharmaceutics, 152:27-36.

Williams et al., 1999, Influence of formulation technique for hydroxypropyl-B- cyclodextrin on the stability of aspirin in HFA 134a; European Journal of Pharmaceutics and Biopharmaceutics 47:145-152.

Williams et al., 1999, Study of Solubility of Steroids in hydrofluoroalkanes propellants; Drug Development and Industrial Pharmacy, 25(12):1227-1234.

Worth et al., 1997, Steroid/cyclodextrin complexes for pulmonary delivery, Proceedings of the International Symposium on Controlled Release of Bioactive Materials, 24:747-748.

Worth et al., Sep. 15-17, 1996, Solubility of beclomethasone dipropionate-cyclodextrin complexes, Eur. J. Pharm. Sciences, 4(Suppl.):S143.

Yoshida et al., 1988, Pharmaceutical evaluation of the hydroxyalkyl ethers of 13- cyclodextrin; International Journal of Pharmaceutics, 46:217-222.

Zannou et al., 2001, Osmotic Properties of Sulfobutylether and Hydroxypropyl Cyclodextrins, Pharmaceutical Research, 18(8):1226-1231.

International Search Report for International Application No. EP 05704917.3.

International Search Report for International Application No. EP 05 70 4919.

International Search Report for International Application No. EP 05 70 4920.

International Search Report for International Application No. PCT/US05/00082.

International Search Report for International Application No. PCT/US05/00084.

International Search Report for International Application No. PCT/US05/00085.

International Search Report for International Application No. PCT/US06/48735.

International Search Report for International Application No. PCT/US06/62346.

International Search Report for International Application No. PCT/US07/04052.

International Search Report for International Application No. PCT/US07/04056.

International Search Report for International Application No. PCT/US07/04057.

International Search Report for International Application No. PCT/US07/71748.

International Search Report for International Application No. PCT/US07/71758.

Barnes et al., 1998, Efficacy and safety of inhaled cortocosterioids, Am. J. Respir. Care Med. 157:S1-S53.

Berg et al., 1998, Pulmicort® suspension for nebulizing tested with different jet nebulizers, J. Aerosol Sci., 19(7):1101-1104.

Bosley et al., 1994, Patient Compliance with Inhaled Medication: Does Combining Beta- Agonists with Corticosteroids Improve Compliance?, Eur. Respir. J., 7:504-509.

Brain et al., 2002, 53. Aerosols: basics and clinical considerations, in Bronchial Asthma, 2nd ed., E.B. Weis et al., eds., Little Brown & Co., pp. 594-603.

Davies et al., 1997, Evaluation of a hydrocortisone/hydroxypropyl-β-cyclodextrin solution for ocular drug delivery, Inti J. Pharmaceutics, 156(2):201-209.

Day et al., 1999, Onset of action of intranasal budesonide (Rhinocort Aqua) in seasonal allergic rhinitis studied in a controlled exposure model, J. Allerg. Clin. Immunol., 105(3):489-494.

Dorow et al., 1993, Efficacy and tolerability of azelastine nasal spray in patients with allergic rhinitis compared to placebo and budesonide, Arzneimmittelforschung, 43(8):909-912.

Edsbacker, 2002, Uptake, retention and biotransformation of corticosteroids in the lung and airways, in. Schleimer et al. eds., Inhaled Steroids in Ashthma: Optimizing Effects in the Airways, Marcel Dekker, New York, pp. 213-246.

Evrard et al., 1999, Influence of cyclodextrins on the solubility and the pharmacokinetics of albendazole, Proceedings of the Ninth International Symposium on Cyclodextrins, Torres Labandeira et al. eds., Kluwer Academic Publishers, NL, pp. 223-226.

Fridriksdottir et al., 1997, Formulation and testing of methazolamide cyclodextrin eye drop solutions, Journal of Controlled Release, 44(1):95-99.

Fridriksdottir et al., Jan. 1996, Design and in vivo testing of 17β-estradiol HPβCD sublingual tablets, Die Pharmazie, 51(1):39-42.

Fridriksdottir et al., Mar. 31-Apr. 2, 1996, Solubilization of β-cyclodextrin: the effect of polymers and various drugs on the solubility of (3-cyclodextrin, Proceedings of the Eighth International Symposium on Cyclodextrins, eds. Szejtli et al., Budapest, 373-376.

Higuchi et al., 1965, Phase-Solubility Techniques, in Advances in Analytical Chemistry and Instrumentation, vol. 4, Reilly ed., John Wiley & Sons, Inc., pp. 117-212.

Jodal et al., Apr. 20-22, 1988, Investigation of the hemolytic effect of the cyclodextrin derivatives, Proceedings of the Fourth International Symposium on Cyclodextrins, Munich, West Germany, pp. 421-425.

Keller et al., May 12-16, 2002, Nebulizer nanosuspensions: important device and formulation interactions, Respiratory Drug Delivery VIII, Tuscon, AZ, pp. 197-206.

Kobayashi et al., Jan. 1996, Pulmonary delivery of salmon calcitonin dry powders containing absorption enhancers in rats, Pharm. Res., 13(1):80-83.

Kristinsson et al., 1996, Dexamethasone-cyclodextrin-polymer co-complexes in aqueous eye drops, Investigative Ophthalmology & Visual Science, 37(6):1199-1203.

Loftsson et al., 1994, The effect of polyvinylpyrrolidone and hydroxypropyl methylcellulose on HPβCD complexation of hydrocortisone and its permeability through hairless mouse skin, European Journal of Pharmaceutical Sciences, 2:297-301.

Loftsson et al., 1994, The effect of water-soluble polymers on drug-cyclodextrin complexation, International Journal of Pharmaceutics (Netherlands), 110(2):169-177.

Loftsson et al., 1996, Effects of cyclodextrins and polymers on topical drug delivery to the eye—evaluations in humans, Proceed-

(56) References Cited

OTHER PUBLICATIONS ings of the 23rd International Symposium on Controlled Release of Bioactive Materials, pp. 453-454.
Loftsson et al., 1996, The influence of water-soluble polymers and pH on hydroxypropyl-β-cyclodextrin complexation of drugs, Drug Development and Industrial Pharmacy, 22(5):401-405.
Loftsson et al., 1997, Cyclodextrins as pharmaceutical excipients, Pharm. Technol. Eur. 9(5):26-34.
Loftsson et al., 1997, Enhanced complexation efficiency of cyclodextrins, Pharmaceutical Research, 14(11):S203.
Loftsson et al., 1998, Cyclodextrin solubilization of ETH-615, a zwitterionic drug, Drug Development and Industrial Pharmacy, 24(4):365-370.
Loftsson et al., 1998, The effect of water-soluble polymers on the aqueous solubility and complexing abilities of β-cyclodextrin, International Journal of Pharmaceutics, 163(1-2):115-121.
Loftsson et al., 1999, Methods to enhance the complexation efficiency of cyclodextrins, S.T.P. Pharma Sciences, 9(3):237-242.
Loftsson et al., 2001, Cyclodextrin solubilization of benzodiazepines: formulation of midazolam nasal spray, International Journal of Pharmaceutics, 212(1):29-40.
Loftsson et al., 2002, Cyclodextrins in eye drop formulations: enhanced topical delivery of corticosteroids to the eye, Acta Ophthalmologica Scandinavica, 80(2):144-50.
Loftsson et al., Apr. 11, 1994, The effect of hydroxypropyl methylcellulose on the release of dexamethasone from aqueous 2-hyroxypropyl-3-cyclodextrin formulations, International Journal of Pharmaceutics (Netherlands), 104:181-184.
Loftsson et al., Oct. 1994, Polymer-cyclodextrin-drug complexes, Pharmaceutical Research, 11(10):S225.
Loftsson et al., Oct. 1996, Pharmaceutical applications of cyclodextrins. 1. Drug solubilization and stabilization, Journal of Pharmaceutical Sciences, 85(10):1017-1025.
Loftsson et al., Sep. 16, 1996, Drug-cyclodextrin-polymer ternary complexes, European Journal of Pharmaceutical Sciences, 4(SUPPL):5144.
Loftsson et al., Sep. 1996, Solubilization of β-cyclodextrin, Eur. J. Pharm. Sci, 4(Suppl.):5143.
Loftsson et al., Sep. 2001, Sustained drug delivery system based on a cationic polymer and an anionic drug/cyclodextrin complex, Pharmazie, 56(9):746-747.
Loftsson, 1996, Topically effective acetazolamide eye-drop solution in man, Pharmaceutical Sciences, 2(6):277-279.
Loftsson, 1998, Drug-cyclodextrin complexation in the presence of water soluble polymers: enhanced solubility and percutaneous transport, Abstracts of Papers Part 1, 216th ACS National Meeting, Boston, Aug. 23-27, CELL-016.
Loftsson, Apr. 2-6, 1995, The effect of polymers on cyclodextrin complexation, Book of Abstracts, 209th ACS National Meeting, 209(1):33-CELL.
Loftsson, Nov. 1988, Increasing the cyclodextrin complexation of drugs and drug bioavailability through addition of water-soluble polymers, Pharmazie, 53(11):733-740.
Mager et al., Nov. 2002, Quantitative structure-pharmacokinetic/pharmacodynamic relationships of corticosteroids in man, J. Pharm. Sci. 91(11):2441-2451.
Masson et al., 1999, Drug-cyclodextrin complexation in the presence of water-soluble polymers: enhanced solubility and percutaneous transport, ACS Symposium Series, 737 (Polysaccharide Applications), pp. 24-45.
Modified Cyclodextrins: Scaffolds and Templates for Supremolecular Chemistry, Easton et al., eds., Imperial College Press, London, UK, 1999.
Nagase et al., 2001, Improvement of some pharmaceutical properties of DY-9760e by sulfobutyl ether (β-cyclodextrin, International Journal of Pharmaceutics, 229: 163-172.
New Trends in Cyclodextrins and Derivatives, Duchene ed., Editions de Sante, Paris, France, 1991.

O'Callaghan, 1990, Particle size of beclomethasone dipropionate produced by two nebulisers and two spacing devices, Thorax, 45:109-111.
O'Callaghan, 2002, The output of flunisolide from different nebulisers, J. Pharm, Pharmacol., 54:565-569.
Okimoto et al., 1996, The Interaction of Charged and Uncharged Drugs with Neutral (HP-β-CD) and Anionically Charged (SBE7-β-CD) β-Cyclodextrins, Pharmaceutical Research, 13(2):256-264.
O'Riordan, 2002, Formulations and nebulizer performance, Respiratory Care, 47(11):1305-1313.
Plaut et al., Nov. 3, 2005, Allergic Rhinitis, New England Journal of Medicine, 353:1934-1944, 2005.
Polymer Science, in Physical Pharmacy. Physical Chemical Principles in Pharmaceutical Sciences, 3rd edition, Martin et al., 1983, pp. 592-638.
Polymers and Macromolecules, in Physicochemical Principles of Pharmacy, 2nd edition, Florence et al., eds. pp. 281-334, 1988.
Rajewski et al., 1996, Pharmaceutical applications of cyclodextrins. 2. In vivo drug delivery, J. Pharm. Sci. 85(11):1142-1169 (abstract).
Remington's Pharmaceutical Sciences, 18th Ed., Gennaro ed., Mack Publishing Company, Easton, PA, 1990, pp. 291-294.
Salapatek et al., 2011, Solubilized nasal steroid (CDX-947) when combined in the same solution nasal spray with an antihistamine (CDX-313) provides improved, fast-acting symptom relief in patients with allergic rhinitis, Allergy Asthma Proc., 32:221-229.
Savolainen et al., 1998, Co-administration of a water-soluble polymer increases the usefulness of cyclodextrins in solid oral dosage forms, Pharmaceutical Research, 15(11):1696-1701.
Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.
Sharpe et al., 2003, Comparison of the flow properties of aqueous suspension corticosterioid nasal sprays under differing sampling conditions, Drug Dev. Ind. Pharm. 29(9)1005-1012.
Sigurdardottir et al., Dec. 29, 1995, The effect of polyvinylpyrrolidone on cyclodextrin complexation of hydrocortisone and its diffusion through hairless mouse skin, International Journal of Pharmaceutics (Netherlands), 126:73-78,.
Stella et al., 1999, Mechanisms of drug release from cyclodextrin complexes, Advanced Drug Delivery Rviews, 36:3-16.
Stella, Mar. 31-Apr. 2, 1996, SBE7-β-CD, a new, novel and safe polyanionic β-cyclodextrin derivative: characterization and biomedical applications, Proceedings of the Eighth International Symposium on Cyclodextrins, Budapest, Hungary, pp. 471-476.
Stern et al,, Oct. 1998, Nasal budesonide offers superior symptom relief in perennial allergic rhinitis in comparison to nasal azelastine, Ann. Allergy Asthma Immunol,, 81(4):354-358.
Storr et al., 1986, Nebulised beclomethasone dipropionate in preschool asthma, Archives of Desease in Childhood, 61:270-273.
van der Kuy et al., Nov. 1999, Eur. J. Olin. Pharmacol., 55(9):677-680.
Waldrep et al., 1994, J. Aerosol Med., 7(2):135-145.
Wang et al., 1997, Effect of topical applications of budesonide and azelastine of nasal symptoms, eosinophil count and mediator release in atopic patients after nasal allergen challenge during the pollen season, Int. Arch. Allergy Immunol. 114(2):185-192.
Webb et al., 1986, Nebulised beclomethasone dipropionate suspension, Arch. Dis. Child, 61:1108-1110.
Unpublished Experimental Results, Oct. 2006, 4 pp.
Jarvinen et al., 1995, Sulfobutyl ether β-cyclodextrin (SBE-β-CD) in eye drops improves the tolerability of a topically applied pilocarpine prodrug in rabbits, Journal of Ocular Pharmacology and Therapeutics, 11(2):95-106.
Uekama et al., 1994, 14. Application of cyclodextrins, in de Boer., ed., Drug Absorption Enhancement: Concepts, Possibilities, Limitations and Trends, Harwood Academic Publishers, Switzerland, pp. 411-456.
Uekama et al., 1998, Cyclodextrin drug carrier systems, Chem. Rev., 98:2045-2076.

(56) References Cited

OTHER PUBLICATIONS

Waldrep et al., 1994, Nebulized glucocorticoids in liposomes: aerosol characteristics and human dose estimates, J. Aerosol Med., 7(2):135-145.
Drugs in Japan, 2009, pp. 2161-2162.

* cited by examiner

Cyclodextrin Concentration [Molar] in Phosphate Buffered Saline
pH 7.4, 37° C, 5 min Incubation o-HPCD; ■-SBE4CD; ▲-SBE7CD; -SBE9CD

FIG. 8

Comparison of Dv50 Values for all Three Nebulizers

(Bar chart: Diameter (um) vs Nebulizer Device — Pari LC Plus, Hudson, Mystique; series: Pulmicort, 5% Captisol, 10% Captisol, 20% Captisol)

FIG. 9

Captisol Output From Various Nebulizer Setups

(Line chart: Captisol Output (mg/min) vs Captisol Concentration (mg/mL); series: Raindrop-Dog, Raindrop-Rat, Pari LC Star-Rat, DeVilbiss-Rat, Pari LC Plus-NB, Pari LC Star-UNC)

Budesonide Stability - pH 6 @ 60°C

Light Stability of Budesonide with and without SBE7-β-CD

Average Distribution of Radiolabel in Budesonide Studies of CEBUD Comparison of eFlow and Pari LC+ Nebulizers

INHALANT FORMULATION CONTAINING SULFOALKYL ETHER CYCLODEXTRIN AND CORTICOSTEROID

CROSS-REFERENCE TO EARLIER FILED APPLICATIONS

The present application is a continuation-in-part of and claims the priority of U.S. application Ser. No. 11/479,979 filed Jun. 30, 2006, which is a continuation-in-part of PCT International Application No. PCT/US05/00082 filed Dec. 31, 2004, which claims benefit of the filing date of provisional application No. 60/533,628 filed Dec. 31, 2003, the disclosures of which are hereby incorporated by reference in their entirety.

FIELD OF THE INVENTION

The present invention relates to methods of and systems for administering formulations of sulfoalkyl ether cyclodextrin and corticosteroid, such as budesonide, by nebulization and inhalation. The invention also relates to methods of treating respiratory diseases or disorders of the air passageways.

BACKGROUND OF THE INVENTION

The delivery of a drug by inhalation allows deposition of the drug in different sections of the respiratory tract, e.g., throat, trachea, bronchi and alveoli. Generally, the smaller the particle size, the longer the particle will remain suspended in air and the farther down the respiratory tract the drug can be delivered. Corticosteroids are delivered by inhalation using nebulizers, metered dose inhalers, or dry powder inhalers. The principle advantages of nebulizers over other methods of pulmonary installation are that patient cooperation is not required and the delivery of higher doses of medication is easier. The main concerns about nebulizers, however, are their increased cost, reduced portability and the inconvenience of needing to prepare medication beforehand and the increased time requirement for administering a treatment. A method of improving the administration of drugs, such as corticosteroids by nebulization would be desired.

Budesonide ((R,S)-11β, 16α, 17, 21-tetrahydroxypregna-1, 4-diene-3, 20-dione cyclic 16, 17-acetal with butyraldehyde; $C_{25}H_{34}O_6$; Mw: 430.5) is well known. It is provided commercially as a mixture of two isomers (22R and 22S). Budesonide is an anti-inflammatory corticosteroid that exhibits potent glucocorticoid activity. Administration of budesonide is indicated for maintenance treatment of asthma and as prophylactic therapy in children.

Commercial formulations of budesonide are sold by AstraZeneca LP (Wilmington, Del.) under the trademarks ENTOCORT™ EC, PULMICORT RESPULES®, Rhinocort Aqua®, Rhinocort® Nasal Inhaler and Pulmicort Turbuhaler®, and under its generic name. PULMICORT RESPULES® suspension, which is a sterile aqueous suspension of micronized budesonide, is administered by inhalation using a nebulizer, in particular a compressed air driven jet nebulizer that delivers from 2 to 18% of the drug mass contained in the nominal charge. The general formulation for a unit dose of the PULMICORT RESPULES is set forth in U.S. Pat. No. 6,598,603, and it is an aqueous suspension in which budesonide is suspended in an aqueous medium comprising about 0.05 to 1.0 mg of budesonide, 0.05 to 0.15 mg of NaEDTA, 8.0 to 9.0 mg of NaCl, 0.15 to 0.25 mg of polysorbate, 0.25 to 0.30 mg of anhydrous citric acid, and 0.45 to 0.55 mg of sodium citrate per one ml of water. RHINOCORT® NASAL INHALER™ is a metered-dose pressurized aerosol unit containing a suspension of micronized budesonide in a mixture of propellants. RHINOCORT® AQUA™ is an unscented metered-dose manual-pump spray formulation containing a suspension of micronized budesonide in an aqueous medium. The suspensions should not be administered with an ultrasonic nebulizer.

A wide variety of nebulizers differing in mode of operation are available, e.g. jet nebulizers (optionally sold with compressors), ultrasonic nebulizers, vibrating membrane, vibrating mesh nebulizers, vibrating plate nebulizers, vibrating cone nebulizers, and others. The vibrating mesh, vibrating cone or vibrating plate nebulizers are of particular interest since they do not require the use of an air compressor for delivery, have a minimal residual volume in the reservoir after delivery of a unit dose, and can be used to deliver low volumes of inhalable solutions. Exemplary vibrating membrane, mesh or plate nebulizers are described by R. Dhand (*Respiratory Care*, (December 2002), 47(12), p. 1406-1418). Keller et al. (ATS 99th International Conference, Seattle, May 16-21, 2003; poster 2727) disclose the results of a study on the administration of AZTREONAM with a PARI eFlow nebulizer and report low oropharyngeal deposition, nebulization efficiency unaffected by fill volume, a respirable fraction of 82±1.7%, constant dose administration per inhalation cycle time, and an excellent correlation between delivered dose, fill volume and nebulization time, and expected high lung deposition.

The desired properties of a liquid for nebulization generally include: 1) reduced viscosity; 2) sterile medium; 3) reduced surface tension; 4) stability toward the mechanism of the nebulizer; 5) moderate pH of about 4-10; 6) ability to form droplets with an MMAD of <5 µm or preferably <3 µm; 7) absence of irritating preservatives and stabilizing agents; 8) suitable tonicity. On the one hand, suspensions possess some advantages but on the other hand solutions possess other advantages.

Smaldone et al. (*J. Aerosol Med.* (1998), 11, 113-125) disclose the results of a study on the in vitro determination of inhaled mass and particle distribution of a budesonide suspension. They conclude that 2%-18% of the nebulizer's charge of budesonide was delivered from the suspension, meaning that budesonide delivery was incomplete resulting in a significant waste of drug. In the thirteen most efficient systems, the suspension can be nebulized sufficiently well for lower respiratory tract delivery.

Another study further demonstrated the highly variable efficiency of nebulization from one nebulizer to another. Barry et al. (*J. Allergy Clin. Immunol.* (1998), 320-321) state that this variability should be taken into account when treating patients with nebulized budesonide. Berg et al. (*J. Aerosol Sci.* (1998), 19(7), 1101-1104) also report the highly variable efficiency of nebulization of PULMICORT™ suspension from one nebulizer to the next. Moreover, the mass mean aerodynamic diameter (MMAD) of the nebulized droplets is highly variable from one nebulizer to the next. In general, suspensions are less efficiently nebulized than solutions, O'Riordan (Respiratory Care, (2002), 1305-1313). Inhaled corticosteroids are utilized in the treatment of asthma and are of significant benefit because they are delivered directly to the site of action, the lung. The goal of an inhaled corticosteroid is to provide localized therapy with immediate drug activity in the lungs. Inhaled corticosteroids are well absorbed from the lungs. In fact, it can be assumed that all of the drug available at the receptor site in the lungs will be absorbed systemically. However, it is well known that using current methods and formulations the greater part of an inhaled corticosteroid dose is swallowed and becomes available for oral absorption, resulting in unwanted systemic effects. For inhaled corticosteroids, high pulmonary availability is more important than high oral bioavailability because the lung is the target organ. A product with high pulmonary availability has greater potential to exert positive effects in the lung. The ideal inhaled corticosteroid formulation would provide minimum oral delivery thereby reducing the likelihood of systemic adverse effects.

The majority of the corticosteroid dose delivered to the lung is absorbed and available systemically. For the portion of the inhaled corticosteroid dose delivered orally, bioavailability depends upon absorption from the GI tract and the extent of first pass metabolism in the liver. Since this oral component of corticosteroid drug delivery does not provide any beneficial therapeutic effect but can increase systemic side effects, it is desirable for the oral bioavailability of inhaled corticosteroid to be relatively low.

Both particle size and formulation influence the efficacy of an inhaled corticosteroid. The formulation of a drug has a significant impact on the delivery of that drug to the lungs, and therefore its efficacy. Most important in the delivery of drug to the lung are the aerosol vehicle and the size of the particles delivered. Additionally, a reduced degree of pulmonary deposition suggests a greater degree of oropharyngeal deposition. Due to a particular formulation employed, some corticosteroids are more likely to be deposited in the mouth and throat and may cause local adverse effects.

While receptor distribution is the major determinant of bronchodilator efficacy, particle size appears to be more important in determining the efficacy of an inhaled corticodsteroid. The smallest airways have an internal diameter of 2 micrometers (mcm) or less. Thus, an inhaler with particles having a mean aerodynamic diameter of 1 mcm should have a greater respirable fraction than an inhaler with particles that have an average diameter of 3.5 to 4 mcm. For patients with obstructive lung disease, all particles should ideally be no greater than 2 to 3 mcm. A particle that is small (less than 5 mcm) is more likely to be inhaled into the smaller airways of the lungs, thus improving efficacy. In contrast, particles that are larger than 5 mcm can be deposited in the mouth and throat, both reducing the proportion of particles that reach the lungs and potentially causing local adverse effects such as oral candidiasis and hoarseness (dysphonia). Particles having a mass median aerodynamic diameter (MMAD) of close to 1 mcm are considered to have a greater respirable fraction per dose than those with a diameter of 3.5 mcm or greater.

A further disadvantage to the nebulization of budesonide suspensions is the need to generate very small droplets, MMDD of about <3 µm. Since the nebulized droplets are so small, then the micronized budesonide must be even smaller or in the range of 0.5-2.0 µm and the particles should have a narrow particle size distribution. Generation of such particles is difficult.

Even so, efforts have been made to improve the nebulization of budesonide suspensions with ultrasonic nebulizers by using submicron-sized particles (Keller et al. in *Respiratory Drug Delivery VIII* (2002), 197-206). A suspension of nanoparticles (0.1-1.0 µm) of the corticosteroid might be used to increase the proportion of respirable particles as compared to a coarser suspension as in the PULMICORT™ suspension. No improvement over PULMICORT™ suspension (about 4.4 µm budesonide particle size in suspension) was observed. Moreover, concerns exist regarding the use of nanosuspensions in that the small particles (<0.05 µm) may induce an allergic response in a subject. Sheffield Pharmaceuticals, Inc. (St. Louis, Mo.; "*The Pharmacokinetics of Nebulized Nanocrystal Budesonide Suspension in Healthy Volunteers*", Kraft, et al. in *J. Clin. Pharmacol.*, (2004), 44:67-72) has disclosed the preparation and evaluation of UDB (unit dose budesonide), which is a suspension-based formulation containing nanoparticles of budesonide dispersed in a liquid medium. This product is being developed by MAP Pharmaceuticals, Inc. (Mountain View, Calif.). Seeman et al. (ATS 99th International Conference, Seattle, May 16-21, 2003; poster 2727) disclose the results of a study evaluating the performance of the PARI eFlow nebulizer with a budesonide suspension (PULMICORT RESPULES, 500 µg/ml, in a 2 ml ampoule) and report achieving a MMAD of 3.6-4.2 µm and a respirable fraction of greater than 67%.

The inhalation of drug particles as opposed to dissolved drug is known to be disadvantageous. Brain et al. (*Bronchial Asthma*, 2nd Ed. (Ed. E. B. Weis et al., Little Brown & Co. (1985), pp. 594-603) report that less soluble particles that deposit on the mucous blanket covering pulmonary airways and the nasal passages are moved toward the pharynx by the cilia. Such particles would include the larger drug particles deposited in the upper respiratory tract. Mucus, cells and debris coming from the nasal cavities and the lungs meet at the pharynx, mix with saliva, and enter the gastrointestinal tract upon being swallowed. Reportedly, by this mechanism, particles are removed from the lungs with half-times of minutes to hours. Accordingly, there is little time for solubilization of slowly dissolving drags, such as budesonide. In contrast, particles deposited in the nonciliated compartments, such as the alveoli, have much longer residence times. Since it is difficult to generate very small particles of budesonide for deep lung deposition, much of the inhaled suspension would likely be found in the upper to middle respiratory tract. However, it is much easier to generate small droplets from a solution than it is from a suspension of solids. For these reasons, nebulization of a budesonide-containing solution should be preferred over that of a suspension.

O'Riordan (*Respiratory Care* (2002 November), 47(11), 1305-1313) states that drugs can be delivered by nebulization of either solutions or suspensions, but that in general, nebulization of a solution is preferred over that of a suspension. He states that ultrasonic nebulizers should not be used on suspensions and should be used only on solutions.

O'Callaghan (*Thorax*, (1990), 45, 109-111), Storr et al. (*Arch. Dis. Child* (1986), 61, 270-273), and Webb et al. (*Arch. Dis. Child* (1986), 61, 1108-1110) suggest that nebulization of corticosteroid (in particular beclomethasone) solutions may be preferred over that of suspensions because the latter may be inefficient if the nebulized particles are too large to enter the lung in therapeutically effective amounts. However, data presented by O'Callaghan (*J. Pharm. Pharmacol.* (2002), 54, 565-569) on the nebulization of flunisolide solution versus suspension showed that the two performed similarly. Therefore, it cannot be generalized that nebulization of a solution is preferred over that of a suspension.

Accordingly, there is a widely recognized need for a non-suspension formulation comprising a corticosteroid for administration via nebulization. However, the PULMICORT® suspension unit dose formulation is widely available and accepted in the field of inhalation therapy. It would be of great benefit to this field of therapy to provide a method of improving the administration of the PULMICORT® suspension unit dose formulation, or more generally, of a suspension unit dose formulation containing a corticosteroid.

However, the current focus in nebulizer therapy is to administer higher concentrations of drug, use solution, preferably predominantly aqueous-based solutions in preference to non-aqueous or alcoholic or non-aqueous alcoholic solutions or suspensions if possible, minimize treatment time, synchronize nebulization with inhalation, and administer smaller droplets for deeper lung deposition of drug.

Corticosteroid-containing solutions for nebulization are known. There are a number of different ways to prepare solutions for nebulization. These generally have been prepared by the addition of a cosolvent, surfactant, or buffer. However, cosolvents, such as ethanol, polyethylene glycol and propylene glycol are only tolerated in low amounts when administered by inhalation due to irritation of the respiratory tract. There are limits to acceptable levels of these cosolvents in inhaled products. Typically, the cosolvents make up less than about 35% by weight of the nebulized composition, although it is the total dose of cosolvent as well as its concentration that determines these limits. The limits are set by the propensity of these solvents either to cause local irritation of lung tissue, to form hyperosmotic solutions that would draw fluid into the lungs, and/or to intoxicate the patient. In addition, most potential hydrophobic therapeutic agents are not sufficiently soluble in these cosolvent mixtures.

Saidi et al. (U.S. Pat. No. 6,241,969) disclose the preparation of corticosteroid-containing solutions for nasal and pulmonary delivery. The dissolved corticosteroids are present in a concentrated, essentially non-aqueous form for storage or in a diluted, aqueous-based form for administration.

Keller et al. (in Respiratory Drug Delivery IX (2004) 221-231) disclose the deposition of solution formulations containing budesonide and surfactants to children.

Lintz et al. (AAPS Annual Meeting and Exposition, Baltimore, Nov. 8, 2004; Poster M1128) disclose the preparation and aerosol characterization of liquid formulations containing budesonide, water, citrate salt, sodium chloride and alcohol, propylene glycol and/or surfactant, such as Tween, Pluronic, or phospholipids with HLB-values between 10 and 20. The aerosol characterization of such a combination surfactant solution in a vibrating membrane/mesh nebulizer (the Pari eFlow) compared to a suspension was studied using adult and child breath simulation. They reported a respirable fraction of 83.3% for the PARI eFlow with the solution and 61% for the PULMICORT RESPULES with the PARI LC+. They also reported the results regarding the respirable drug delivery rate (% drug <5 μm/min), delivered dose (% of drug charged to device), drug delivery rate (% drug/min), and respirable dose (%<5 μm).

Schueepp et al. (ATS 99th International Conference, Seattle, May 16-21, 2003; poster 1607) disclose assessment of the aerosol performance of a customized eFlow Baby Functional Model with an experimental budesonide solution (100 μg in 0.5 ml) utilizing a baby cast model and applying different breathing patterns.

An alternative approach to administration of the PULMICORT™ suspension is administration of a liposome formulation. Waldrep et al. (*J. Aerosol Med.* (1994), 7(2), 135-145) reportedly succeeded in preparing a liposome formulation of budesonide and phosphatidylcholine derivatives.

None of the above-identified formulations has provided a method of improving the administration of a suspension-based unit dose formulation containing a corticosteroid. Instead, the general focus of the art has been to completely circumvent formulating a suspension by first preparing a liquid formulation that is then divided into multiple unit doses that are packaged for marketing and then sold for use.

Solubilization of drugs by cyclodextrins and their derivatives is well known. Cyclodextrins are cyclic carbohydrates derived from starch. The unmodified cyclodextrins differ by the number of glucopyranose units joined together in the cylindrical structure. The parent cyclodextrins contain 6, 7, or 8 glucopyranose units and are referred to as α-, β-, and γ-cyclodextrin respectively. Each cyclodextrin subunit has secondary hydroxyl groups at the 2 and 3 positions and a primary hydroxyl group at the 6-position. The cyclodextrins may be pictured as hollow truncated cones with hydrophilic exterior surfaces and hydrophobic interior cavities. In aqueous solutions, these hydrophobic cavities provide a haven for hydrophobic organic compounds that can fit all or part of their structure into these cavities. This process, known as inclusion complexation, may result in increased apparent aqueous solubility and stability for the complexed drug. The complex is stabilized by hydrophobic interactions and does not involve the formation of any covalent bonds.

This dynamic and reversible equilibrium process can be described by Equations 1 and 2, where the amount in the complexed form is a function of the concentrations of the drug and cyclodextrin, and the equilibrium or binding constant, $K_b$. When cyclodextrin formulations are administered by injection into the blood stream, the complex rapidly dissociates due to the effects of dilution and non-specific binding of the drug to blood and tissue components.

$$\text{Drug} + \text{Cyclodextrin} \overset{K_b}{\leftrightarrow} \text{Complex} \qquad \text{Equation 1}$$

$$K_b = \frac{[\text{Complex}]}{[\text{Drug}][\text{Cyclodextrin}]} \qquad \text{Equation 2}$$

Binding constants of cyclodextrin and an active agent can be determined by the equilibrium solubility technique (T. Higuchi et al. in "Advances in Analytical Chemistry and Instrumentation Vol. 4"; C. N. Reilly ed.; John Wiley & Sons, Inc, 1965, pp. 117-212). Generally, the higher the concentration of cyclodextrin, the more the equilibrium process of Equations 1 and 2 is shifted to the formation of more complex, meaning that the concentration of free drug is generally decreased by increasing the concentration of cyclodextrin in solution.

The underivatized parent cyclodextrins are known to interact with human tissues and extract cholesterol and other membrane components, particularly upon accumulation in the kidney tubule cells, leading to toxic and sometimes fatal renal effects.

The parent cyclodextrins often exhibit a differing affinity for any given substrate. For example, γ-cyclodextrin often forms complexes with limited solubility, resulting in solubility curves of the type Bs. This behavior is known for a large number of steroids which imposes serious limitations towards the use of γ-CD in liquid preparations. β-CD, however, does not complex well with a host of different classes of compounds. It has been shown for β-DD and γ-CD that derivatization, e.g. alkylation, results in not only better aqueous solubility of the derivatives compared to the parent CD, but also changes the type of solubility curves from the limiting Bs-type to the more linear A-type curve (Bernd W. Muller and Ulrich Brauns, "Change of Phase-Solubility Behavior by Gamma-Cyclodextrin Derivatization", *Pharmaceutical Research* (1985) p 309-310).

Chemical modification of the parent cyclodextrins (usually at the hydroxyls) has resulted in derivatives with improved safety while retaining or improving the complexation ability. Of the numerous derivatized cyclodextrins prepared to date, only two appear to be commercially viable: the 2-hydroxypropyl derivatives (HP-CD; neutral

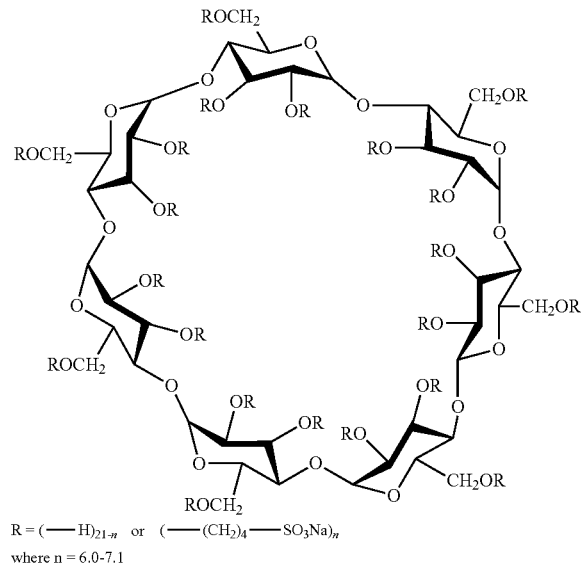

R = (——H)$_{21-n}$ or (——(CH$_2$)$_4$——SO$_3$Na)$_n$
where n = 6.0-7.1

Sulfobutyl Ether-β-Cyclodextrin (Captisol®)

cyclodextrins being commercially developed by Janssen and others), and the sulfoalkyl ether derivatives, such as sulfobutyl ether, (SBE-CD; anionic cyclodextrins being developed by CyDex, Inc.) However, the HP-β-CD still possesses toxicity that the SBE-CD does not.

U.S. Pat. No. 5,376,645 and U.S. Pat. No. 5,134,127 to Stella et al., U.S. Pat. No. 3,426,011 to Parmerter et al., Lammers et al. (*Recl. Trav. Chim. Pays-Bas* (1972), 91(6), 733-742); *Staerke* (1971), 23(5), 167-171) and Qu et al. (*J. Inclusion Phenom. Macro. Chem.*, (2002), 43, 213-221) disclose sulfoalkyl ether derivatized cyclodextrins. The references suggest that SAE-CD should be suitable for solubilizing a range of different compounds. However, Stella discloses that the molar ratio of sulfoalkyl ether derivatized cyclodextrin to active ingredient suitable for solubilization of the active ingredient, even a corticosteroid, in water ranges from 10:1 to 1:10.

A sulfobutyl ether derivative of beta cyclodextrin (SBE-β-CD), in particular the derivative with an average of about 7 substituents per cyclodextrin molecule (SBE7-β-CD), has been commercialized by CyDex, Inc. as CAPTISOL®. The anionic sulfobutyl ether substituent dramatically improves the aqueous solubility of the parent cyclodextrin. In addition, the presence of the charges decreases the ability of the molecule to complex with cholesterol as compared to the hydroxypropyl derivative. Reversible, non-covalent, complexation of drugs with CAPTISOL® cyclodextrin generally allows for increased solubility and stability of drugs in aqueous solutions. While CAPTISOL® is a relatively new but known cyclodextrin, its use in the preparation of corticosteroid-containing solutions for nebulization has not previously been evaluated.

Hemolytic assays are generally used in the field of parenteral formulations to predict whether or not a particular formulation is likely to be unsuitable for injection into the bloodstream of a subject. If the formulation being tested induces a significant amount of hemolysis, that formulation will generally be considered unsuitable for administration to a subject. It is generally expected that a higher osmolality is associated with a higher hemolytic potential. As depicted in FIG. 1 (Thompson, D. O., *Critical Reviews in Therapeutic Drug Carrier Systems*, (1997), 14(1), 1-104), the hemolytic behavior of the CAPTISOL® is compared to the same for the parent β-cyclodextrin, the commercially available hydroxypropyl derivatives, ENCAPSIN™ cyclodextrin (degree of substitution~3-4) and MOLECUSOL® cyclodextrin (degree of substitution~7-8), and two other sulfobutyl ether derivatives, SBE1-β-CD and SBE4-β-CD. Unlike the other cyclodextrin derivatives, sulfoalkyl ether (SAE-CD) derivatives, in particular those such as the CAPTISOL (degree of substitution~7) and SBE4-β-CD (degree of substitution~4), show essentially no hemolytic behavior and exhibit substantially lower membrane damaging potential than the commercially available hydroxypropyl derivatives at concentrations typically used to solubilize pharmaceutical formulations. The range of concentrations depicted in the figure includes the concentrations typically used to solubilize pharmaceutical formulations when initially diluted in the blood stream after injection. After oral administration, SAE-CD does not undergo significant systemic absorption.

The osmolality of a formulation is generally associated with its hemolytic potential: the higher the osmolality (or the more hypertonic), the greater the hemolytic potential. Zannou et al. ("Osmotic properties of sulfobutyl ether and hydroxypropyl cyclodextrins", *Pharma. Res.* (2001), 18(8), 1226-1231) compared the osmolality of solutions containing SBE-CD and HP-CD. As depicted in FIG. 2, the SBE-CD containing solutions have a greater osmolality than HP-CD containing solutions comprising similar concentrations of cyclodextrin derivative. Thus, it is surprising that SAE-CD exhibits lower hemolysis than does HP-CD at equivalent concentrations, even though HP-CD has a lower osmolality.

Methylated cyclodextrins have been prepared and their hemolytic effect on human erythrocytes has been evaluated. These cyclodextrins were found to cause moderate to severe hemolysis (Jodal et al., *Proc. 4$^{th}$ Int. Symp. Cyclodextrins*, (1988), 421-425; Yoshida et al., *Int. J. Pharm.*, (1988), 46(3), 217-222).

Administration of cyclodextrins into the lungs of a mammal may not be acceptable. In fact, literature exists on the potential or observed toxicity of native cyclodextrins and cyclodextrin derivatives. The NTP Chemical Repository indicates that α-cyclodextrin may be harmful by inhalation. Nimbalkar et al. (*Biotechnol. Appl. Biochem.* (2001), 33, 123-125) cautions on the pulmonary use of an HP-β-CD/diacetyldapsone complex due to its initial effect of delaying cell growth of lung cells.

Even so, a number of studies regarding the use of cyclodextrins for inhalation have been reported although none have been commercialized. The studies suggest that different drug-cyclodextrin combinations will be required for specific optimal or even useful inhaled or intra-nasal formulations. Attempts have been made to develop cyclodextrin-containing powders and solutions for buccal, pulmonary and/or nasal delivery.

U.S. Pat. No. 5,914,122 to Otterbeck et al. discloses the preparation of stable budesonide-containing solutions for rectal administration as a foam. They demonstrate the use of cyclodextrin, such as β-CD, γ-CD or HP-β-CD, and/or EDTA as a stabilizer. Cyclodextrin is also suggested as a solubilizer for increasing the concentration of budesonide in solution. In each case, the greatest shelf-life they report for any of their formulations is, in terms of acceptable retention of the active ingredient, only three to six months.

U.S. Pregrant Patent Publication No. 20020055496 to McCoy et al. discloses essentially non-aqueous intra-oral formulations containing HP-β-CD. The formulations may be administered with an aerosol, spray pump or propellant.

Russian Patent No. 2180217 to Chuchalin discloses a stable budesonide-containing solution for inhalation. The solution comprises budesonide, propylene glycol, poly(ethylene oxide), succinic acid, Trilon B, nipazole, thiourea, water, and optionally HP-β-CD.

Müller et al. (*Proceed. Int'l. Symp. Control. Rel. Bioact. Mater.* (1997), 24, 69-70) discloses the results of a study on the preparation of budesonide microparticles by an ASES (Aerosol Solvent Extraction System) supercritical carbon dioxide process for use in a dry powder inhaler. HP-β-CD is suggested as a carrier for a powder.

Müller et al. (U.S. Pat. No. 6,407,079) discloses pharmaceutical compositions containing HP-β-CD. They suggest that nasal administration of a solution containing the cyclodextrin is possible.

The art recognizes that it may be necessary to evaluate structurally related variations of a particular type of cyclodextrin derivative in order to optimize the binding of a particular compound with that type of cyclodextrin derivative. However, it is often the case that there are not extreme differences in the binding of a particular compound with a first embodiment versus a second embodiment of a particular cyclodextrin derivative. For example, cases where there are extreme differences in the binding of a particular therapeutic agent for a first cyclodextrin derivative versus a structurally related second cyclodextrin derivative are uncommon. When such situations do exist, they are unexpected. Worth et al. (24th *International Symposium on Controlled Release of Bioactive Materials* (1997)) disclose the results of a study evaluating the utility of steroid/cyclodextrin complexes for pulmonary delivery. In side-by-side comparisons, β-CD, SBE7-β-CD, and HP-β-CD were evaluated according to their ability to form inclusion complexes with beclomethasone dipropionate (BDP) and its active metabolite beclomethasone monopropionate (BMP). BMP was more easily solubilized with a cyclodextrin, and the observed order of solubilizing power was: HP-β-CD (highest)>β-CD>SBE7-β-CD. Thus, the artisan would expect that SAE-CD derivatives would not be as suitable for use in solubilizing corticosteroids such as BMP or BDP. Although no results regarding actual utility in an inhaled formulation were disclosed, they suggest that BMP rather than BDP would be a better alternative for development of a nebulizer solution.

Kinnarinen et al. (11th *International Cyclodextrin Symposium* CD, (2002)) disclose the results of a study of the in vitro pulmonary deposition of a budesonide/γ-CD inclusion complex for dry powder inhalation. No advantage was observed by complexation with γ-CD. Vozone et al. (11th *International Cyclodextrin Symposium* CD, (2002)) disclose the results of a study on the complexation of budesonide with γ-cyclodextrin for use in dry powder inhalation. No difference was observed within emitted doses of the cyclodextrin complex or a physical mixture of budesonide and the CD. But, a difference observed in the fine particle fraction of both formulations suggested that use of a cyclodextrin complex for pulmonary drug delivery might increase the respirable fraction of the dry powder.

Pinto et al. (*S.T.P. Pharma. Sciences* (1999), 9(3), 253-256) disclose the results of a study on the use of HP-β-CD in an inhalable dry powder formulation for beclomethasone. The HP-β-CD was evaluated as a complex or physical mixture with the drug in a study of in vitro deposition of the emitted dose from a MICRO-HALER™ inhalation device. The amount of respirable drug fraction was reportedly highest with the complex and lowest with the micronized drug alone.

Rajewski et al. (*J. Pharm. Sci.* (1996), 85(11), 1142-1169) provide a review of the pharmaceutical applications of cyclodextrins. In that review, they cite studies evaluating the use of cyclodextrin complexes in dry powder inhalation systems.

Shao et al (*Eur. J. Pharm. Biopharm.* (1994), 40, 283-288) reported on the effectiveness of cyclodextrins as pulmonary absorption promoters. The relative effectiveness of cyclodextrins in enhancing pulmonary insulin absorption, as measured by pharmacodynamics, and relative efficiency was ranked as follows: dimethyl-β-cyclodextrin>α-cyclodextrin>β-cyclodextrin>γ-cyclodextrin>hydroxypropyl-β-cyclodextrin. In view of this report, the artisan would expect the water soluble derivative of γ-CD to be less suitable for delivering compounds via inhalation than the respective derivative of β-CD because the underivatized β-CD is more suitable than the underivatized γ-CD.

Williams et al. (*Eur. J. Pharm. Biopharm.* (1999 March), 47(2), 145-52) reported the results of a study to determine the influence of the formulation technique for 2-hydroxypropyl-beta-cyclodextrin (HP-β-CD) on the stability of aspirin in a suspension-based pressurized metered-dose inhaler (pMDI) formulation containing a hydrofluoroalkane (HFA) propellant. HP-β-CD was formulated in a pMDI as a lyophilized inclusion complex or a physical mixture with aspirin. Aspirin in the lyophilized inclusion complex exhibited the most significant degree of degradation during the 6-months storage, while aspirin alone in the pMDI demonstrated a moderate degree of degradation. Aspirin formulated in the physical mixture displayed the least degree of degradation. Reportedly, HP-β-CD may be used to enhance the stability of a chemically labile drug, but the drug stability may be affected by the method of preparation of the formulation.

Gudmundsdottir et al. (*Pharmazie* (2001 December), 56(12), 963-6) disclose the results of a study in which midazolam was formulated in aqueous sulfobutylether-beta-cyclodextrin buffer solution. The nasal spray was tested in healthy volunteers and compared to intravenous midazolam in an open crossover trial. The nasal formulation reportedly approaches the intravenous form in speed of absorption, serum concentration and clinical sedation effect. No serious side effects were observed.

Srichana et al. (*Respir. Med.* (2001 June), 95(6), 513-9) report the results of a study to develop a new carrier in dry powder aerosols. Two types of cyclodextrin were chosen; gamma cyclodextrin (γ-CD) and dimethyl-beta-cyclodextrin (DMCD) as carriers in dry powder formulations. Salbutamol was used as a model drug and a control formulation containing lactose and the drug was included. A twin-stage impinger (TSI) was used to evaluate in delivery efficiency of those dry powder formulations. From the results obtained, it was found that the formulation containing γ-CD-enhanced drug delivery to the lower stage of the TSI (deposition=65%) much greater than that of both formulations containing DMCD (50%) and the control formulation (40%) (P<0.05). The haemolysis of red blood cells incubated with the DMCD complex was higher than that obtained in the γ-CD complex. The drug release in both formulations containing γ-CD and DMCD was fast (over 70% was released in 5 min) and nearly all the drug was released within 30 min.

van der Kuy et al. (*Eur. J. Clin. Pharmacol.* (1999 November), 55(9), 677-80) report the results of the pharmacokinetic properties of two intranasal preparations of dihydroergotamine mesylate (DHEM)-containing formulation using a commercially available intranasal preparation. The formulations also contained randomly methylated β-cyclodextrin (RAMEB). No statistically significant differences were found in maximum plasma concentration (Cmax), time to reach Cmax (tmax), area under plasma concentration-time curve (AUC0-8 h), Frel(t=8 h) and Cmax/AUC(t=8 for the three intranasal preparations. The results indicate that the pharmacokinetic properties of the intranasal preparations are not significantly different from the commercially available nasal spray.

U.S. Pat. Nos. 5,942,251 and 5,756,483 to Merkus cover pharmaceutical compositions for the intranasal administration of dihydroergotamine, apomorphine and morphine comprising one of these pharmacologically active ingredients in combination with a cyclodextrin and/or a disaccharide and/or a polysaccharide and/or a sugar alcohol.

U.S. Pat. No. 5,955,454 discloses a pharmaceutical preparation suitable for nasal administration containing a progestogen and a methylated (3-cyclodextrin having a degree of substitution of between 0.5 and 3.0.

U.S. Pat. No. 5,977,070 to Piazza et al. discloses a pharmaceutical composition for the nasal delivery of compounds useful for treating osteoporosis, comprising an effective amount of a physiologically active truncated analog of PTH or PTHrp, or salt thereof and an absorption enhancer selected from the group consisting of dimethyl-β-cyclodextrin.

U.S. Pat. No. 6,436,902 to Backstrom et al. discloses compositions and methods for the pulmonary administration of a parathyroid hormone in the form of a dry powder suitable for inhalation in which at least 50% of the dry powder consists of (a) particles having a diameter of up to 10 microns; or (b) agglomerates of such particles. A dry powder inhaler device contains a preparation consisting of a dry powder comprising (i) a parathyroid hormone (PTH), and (ii) a substance that enhances the absorption of PTH in the lower respiratory tract, wherein at least 50% of (i) and (ii) consists of primary particles having a diameter of up to 10 microns, and wherein the substance is selected from the group consisting of a salt of a fatty acid, a bile salt or derivative thereof, a phospholipid, and a cyclodextrin or derivative thereof.

U.S. Pat. No. 6,518,239 to Kuo et al. discloses a dispersible aerosol formulation comprising an active agent and a dipeptide or tripeptide for aerosolized administration to the lung. The compositions reportedly may also include polymeric excipients/additives, e.g., polyvinylpyrrolidones, derivatized celluloses such as hydroxymethylcellulose, hydroxyethylcellulose, and hydroxypropyl methylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

Nakate et al. (*Eur. J. Pharm. Biopharm.* (2003 March), 55(2), 147-54) disclose the results of a study to determine the improvement of pulmonary absorption of the cyclopeptide FK224 (low aqueous solubility) in rats by co-formulating it with beta-cyclodextrin. The purpose of the study was to investigate the effect of pulmonary delivery on the systemic absorption of FK224 in comparison with other administration routes, and to determine the bioavailability (BA) of FK224 following pulmonary administration in rats using various dosage forms. After administration of an aqueous suspension, the bioavailability was reduced to 2.7% compared with 16.8% for the solution. However, β-cyclodextrin (β-CD) was found to be an effective additive as far as improving the solubility of FK224 was concerned. The bioavailability of the aqueous suspension containing β-CD was increased to 19.2%. It was observed that both the C(max) and AUC of FK224 were increased as the amount of β-CD increased. The plasma profiles showed sustained absorption. They suggest that β-CD is an extremely effective additive as far as improving the pulmonary absorption of FK224 is concerned. They also suggest that β-CD or derivatives with various degrees of aqueous solubility are potential drug carriers for controlling pulmonary absorption.

Kobayashi et al. (*Pharm. Res.* (1996 January), 13(1), 80-3) disclose the results of a study on pulmonary delivery of salmon calcitonin (sCT) dry powders containing absorption enhancers in rats. After intratracheal administration of sCT dry powder and liquid (solution) preparations to rats, plasma sCT levels and calcium levels were measured. Reportedly, sCT in the dry powder and in the liquid were absorbed nearly to the same degree. Absorption enhancers (oleic acid, lecithin, citric acid, taurocholic acid, dimethyl-β-cyclodextrin, octyl-β-D-glucoside) were much more effective in the dry powder than in the solution.

Adjei et al. (*Pharm. Res.* (1992 February), 9(2), 244-9) disclose the results of a study on the bioavailability of leuprolide acetate following nasal and inhalation delivery to rats and healthy humans. Systemic delivery of leuprolide acetate, a luteinizing hormone releasing hormone (LHRH) agonist, was compared after inhalation (i.h.) and intranasal (i.n.) administration. The i.n. bioavailability in rats was significantly increased by α-cyclodextrin (CD), EDTA, and solution volume. Absorption ranged from 8 to 46% compared to i.v. controls. Studies in healthy human males were conducted with leuprolide acetate i.n. by spray, or inhalation aerosol (i.h.), and subcutaneous (s.c.) and intravenous (i.v.) injection. The s.c. injection was 94% bioavailable compared with i.v. The i.n. bioavailability averaged 2.4%, with significant subject-to-subject variability. Inhalation delivery gave a slightly lower intersubject variability. Mean Cmax with a 1-mg dose of solution aerosol was 0.97 ng/ml, compared with 4.4 and 11.4 ng/ml for suspension aerosols given at 1- and 2-mg bolus dosages, respectively. The mean bioavailability of the suspension aerosols (28% relative to s.c. administration) was fourfold greater than that of the solution aerosol (6.6%).

CyDex (*Cyclopedia* (2002), 5(1), 3) discloses that SBE-CD is non-toxic to rats in an inhaled aerosol composition when present alone. They do not disclose a nebulizable composition comprising a drug, in particular a corticosteroid, and SBE-CD. Studies comparing the nebulization of PULMICORT RESPULES and an aqueous inhalable solution of budesonide and SAE-CD in various nebulizers have been disclosed (Zimmerer et al. *Respiratory Drug Delivery IX* (2004) 461-464).

In deciding whether to administer a suspension versus solution, one must also consider the type of nebulizer to be used. The two most common types of nebulizers are the ultrasonic nebulizer and the air driven jet nebulizer. There are significant differences between the two. For example, jet nebulizers cool rather than heat the liquid in the reservoir, whereas ultrasonic nebulizers heat the liquid. While heating of the solution in reservoir can reduce the viscosity of the solution and enhance formation of droplets, excessive heating could lead to drug degradation. The ultrasonic nebulizer is quieter and provides faster delivery than the jet nebulizer, but ultrasonic nebulizers are more expensive and are not advised for the administration of the currently available steroid for nebulization. Most importantly, however, ultrasonic nebulizers generally provide a significantly higher rate of administration than do jet nebulizers.

Patients with asthma are often treated with inhaled short acting or long acting β2-agonists, inhaled anticholinergics, and inhaled corticosteroids alone, sequentially or in combination. Combinations of inhaled corticosteroids and long acting β2-agonists are known, for example budesonide plus formoterol or fluticasone plus salmeterol are available in a dry powder inhaler. However, there is no example of such combinations that are available as a solution for nebulization. Combining the medications into one solution would reduce the time required to administer the medications separately.

For inhaled corticosteroids, high pulmonary availability is more important than high oral bioavailability because the lung is the target organ. A product with high pulmonary availability has greater potential to exert positive effects in the lung. The ideal ICS would have minimum oral bioavailability, reducing the likelihood of systemic adverse effects.

Although extremely effective in the treatment of asthma, inhaled corticosteroids can have a number of adverse side effects such as oral candidiasis, hoarseness (dysphonia), and pharyngitis. Therefore, inhaled corticosteroids are best delivered by a method that minimizes the oral and/or pharyngeal deposition of the corticosteroid and instead maximizes pulmonary delivery.

Some corticosteroids posses a hydroxyl group at position 21 of the corticosteroid. Those compounds include budesonide, flunisolide, triamcinolone acetonide, beclomethasone monopropionate, and the active form of ciclesonide (desisobutyryl-ciclesonide). It is known that ciclesonide is inhaled as an inactive compound and converted by esterases in the lung to its active form, desisobutyryl-ciclesonide (des-CIC). Budesonide conjugates to form intracellular fatty acid esters, which are highly lipophilic. Budesonide forms conjugates with 5 fatty acids: oleate, palmitate, linoleate, palmitoleate, and arachidonate.

In summary, the art suggests that, in some cases, nebulization of solutions may be preferred over that of suspensions and that, in some cases, an ultrasonic nebulizer, vibrating mesh, electronic or other mechanism of aerosolization may be preferred over an air driven jet nebulizer depending upon the nebulization liquid formulations being compared. Even though the art discloses inhalable solution formulations containing a corticosteroid and cyclodextrin, the results of the art are unpredictable. In other words, the combination of one cyclodextrin with one drug does not suggest that another cyclodextrin may be suitable. Neither does the art suggest that one cyclodextrin-corticosteroid inhalable formulation will possess advantages over another cyclodextrin-corticosteroid inhalable formulation.

A need remains in the art for a stabilized aqueous solution budesonide-containing inhalable formulation that does not require the addition of preservatives and that provides significant advantages over other stabilized aqueous solution budesonide-containing inhalable formulations. A need also remains for a method of improving the administration of budesonide-containing suspension formulations by nebulization by converting the suspension to a solution.

There is also a need to develop improved systems that can solubilize water-insoluble drugs for nebulization, and to minimize the levels of cosolvent necessary to accomplish this. The ideal system would consist of non-toxic ingredients and be stable for long periods of storage at room temperature. When nebulized, it would produce respirable droplets in the less than 10 micron or less than 5 micron or less than 3 micron and a substantial portion of extra-fine aerosol in the less than about 1 micron size range.

The need continues to remain for a method of improving the administration, by nebulization, of a suspension-based unit dose formulation. Such a method would reduce the overall time of administration, increase the overall amount of drug administered, reduce the amount of drug left in the reservoir of the nebulizer, increase the portion of pulmonary deposition relative to oropharyngeal deposition of corticosteroid, and/or enhance deep lung penetration of the corticosteroid as compared to such administration, absent the improvement, of the suspension-based unit dose formulation.

SUMMARY OF THE INVENTION

The present invention seeks to overcome the disadvantages present in known formulations. As such, a derivatized cyclodextrin-based, e.g., sulfoalkyl ether cyclodextrin (SAE-CD)-based, inhalable formulation is provided. The present formulation includes a corticosteroid as a principle active agent. The present formulation may provide enhanced solubility and/or enhanced chemical, thermochemical, hydrolytic and/or photochemical stability of the active agent or other ingredients in the formulation. Moreover, the present formulation may possess other advantages, e.g. enhanced drug delivery, increased rate of drug administration, reduced treatment time, reduced toxicity, ease of manufacture, assurance of sterility, improved stability, enhanced bioabsorption, no requirement of particle size control, increased output rate, increased total output, no concern for solid particle growth, enhanced pharmacokinetic profile, reduced corticosteroid-related side effects, enhanced pulmonary deposition, reduced oropharyngeal deposition, improved nebulization performance, and/or no need to confirm formation of a suspension, over other inhalable solution or suspension formulations containing a corticosteroid, such as budesonide.

The invention provides a formulation, system and method for treating a respiratory disease or disorder that is therapeutically responsive to corticosteroid therapy. The system of the invention comprises a nebulizer, and a liquid formulation of the invention. The liquid formulation of the invention comprises a dose of corticosteroid, an aqueous liquid carrier and a solubility enhancer.

The invention provides a method of treating, preventing or ameliorating in a subject a corticosteroid-responsive disease or disorder, meaning a disease or disorder in a subject that can be treated with a therapeutically effective amount of corticosteroid to provide a clinical or therapeutic benefit to the subject. The method comprises: providing an aqueous inhalable formulation comprising a corticosteroid, an aqueous liquid carrier, and solubility enhancer; and delivering or administering via nebulization to a subject in need thereof a dose of about at least 25 µg, 40 µg, at least 45 µg, at least 48 µg, 45-1000 µg, about 1 µg to 20 mg, or 1 µg to 10 mg, 0.01 mg to 10 mg, 0.025 mg to 10 mg, 0.05 mg to 5 mg, 0.1 mg to 5 mg, 0.125 mg to 5 mg, 0.25 mg to 5 mg, 0.5 mg to 5 mg, 0.05 mg to 2 mg, 0.1 mg to 2 mg, 0.125 mg to 2 mg, 0.25 mg to 2 mg, 0.5 mg to 2 mg, 1 µg, 10 µg, 25 µg, 50 µg, 100 µg, 125 µg, 200 µg, 250 µg, 25 to 66 µg, 48 to 81 µg, 73 to 125 µg, 40 µg, 64 µg, 95 µg, 35 to 95 µg, 25 to 125 µg, 60 to 170 µg, 110 µg, 170 µg, 45 to 220 µg, 45 to 85 µg, 48 to 82 µg, 85 to 160 µg, 140 to 220 µg, 120 to 325 µg, 205 µg, 320 µg, 325 µg, 90 to 400 µg, 95 to 170 µg, 165 to 275 µg, or 275 to 400 µg of the corticosteroid. In some embodiments, the corticosteroid is budesonide.

In some embodiments: 1) the inhalable formulation has a volume of about 10 p. 1 to 100 ml, 50 µl to 50 ml, 50 µl to 10 ml, 0.1 to 10 ml, 0.1 ml to less than 10 ml, 0.1 ml to 7.5 ml, 0.1 ml to 5 ml, 0.1 ml to 3 ml, 0.1 ml to 2 ml, 0.1 ml to 1 ml, 0.05 ml to 7.5 ml, 0.05 ml to 5 ml, 0.05 ml to 3 ml, 0.05 ml to 2 ml, or 0.05 ml to 1 ml; 2) the step of delivering or administering is conducted over a period of less than 30 min, less than 20 min, less than 10 min, less than 7 min, less than 5 min, less than 3 min, or less than 2 min, or the time is about 0.05 to 10 min, about 0.1 to 5 min, about 0.1 to 3 min, about 0.1 to 2 min, about 0.1 to 1.5 min, about 0.5 min to about 1.5 min, or about 1 min, or the time is about the time it takes for a subject to take a single breath (about 1 to 3 or 1 to 5 sec); 3) 20% to 85%, or 30% to 80%, or at least 30%, at least 40%, at least 56%, at least 59%, at least 62% of the dose of corticosteroid is delivered to the lungs of the subject; 4) the formulation, system or method provides an enhanced pharmacokinetic profile of 1.5 to 8 fold, 1.5 to 6 fold, 1.5 to 4 fold, 1.5 to 2 fold, 1.64 to 3.55 fold for Cmax, 1.48 to 6.25 fold for Cmax, 1.59 to 3.55 or 1.19 to 6.11 fold for $AUC_{inf}$, 1.69-3.67 or 1.21 to 7.66 fold for $AUC_{last}$, on normalized dose, as compared to administration of a suspension formulation comprising approximately the same amount of corticosteroid and delivered under substantially the same conditions; 5) no more than, 15% to 85%, 15% to 70%, no more than 20% to 70%, no more than 50%, no more than 40%, or no more than 60% of the dose of corticosteroid is delivered to the subject outside the lung.

The present inventors have unexpectedly discovered that SAE-CD is systemically absorbed following administration via inhalation. It is also eliminated from the lungs. SAE-CD also complexes with corticosteroids in aqueous inhalable liquid formulations. Coadministration of the corticosteroid with SAE-CD may result in increased output rate and total drug delivery as compared to a control excluding SAE-CD. Moreover, an inhalable solution of the invention administered by nebulization provides other advantages set forth herein as compared to a control/reference sample of a suspension comprising substantially the same amount of corticosteroid in substantially the same volume of liquid when administered under substantially the same conditions.

The inhalable solution can be used in more types of nebulizers as suspensions can clog vibrating mesh nebulizers and do not perform well in ultrasonic nebulizers. The nebulizers would be more easily cleaned of residual corticosteroid resulting in less contamination. As drug in solution will be distributed equally in the large and small droplets leaving the nebulizer, the fine particle fraction will contain more corticosteroid resulting in a greater respirable dose that can reach the peripheral lung and smaller airways. This may result in less of the total drug depositing in the oropharyngeal cavity and being swallowed, thus reducing the potential for undesired side effects while enhancing bioavailability and maximizing the desired effect. The inhalable solution will also allow reducing the amount of drug in the unit dose and/or reducing the time of nebulization to achieve the desired amount of drug in the lung. The inhalable solution is more easily manufactured and filled into unit doses and product performance does not depend on very tight control of the particle size of ingoing corticosteroid and maintenance of a homogeneous suspension during filling. However, smaller particle size will, in general, facilitate more rapid dissolution during manufacturing. It is not necessary to maintain tight control as described above. It may be terminally sterilized without risk of changing the corticosteroid's particle size of the suspended corticosteroid. The inhalable solution is not subject to change due to particle growth via Ostwald ripening or agglomeration thus the amount of drug in the respirable fraction will not change over time. It does not need to be resuspended prior to administration with carefully scripted procedures to reduce foaming so as not to create large variation is dose. It may be more accurately diluted to achieve the desired amount of drag in the volume placed in the nebulizer. Alternatively, dose adjustment may be controlled more easily by adjusting the time of nebulization as the concentration of the inhalable solution does not change as fast in the nebulizer as does concentration of the suspension, especially in air-jet nebulizers.

An SAE-CD-containing formulation can be prepared with sufficient active agent solubility and stability for a commercial product. If needed, the SAE-CD-containing formulation can be prepared as a clear aqueous solution that can be sterile filtered through a filter having a pore size of 0.45 µm or less and that is stable and preserved under a variety of storage conditions. The invention thus provides a filtration-sterilized liquid formulation comprising a solution of the invention and a method of sterilizing a solution of the invention by sterile filtration through a filter. Sterile filtration can be done without substantial mass loss of solubilized corticosteroid, meaning less than 5% mass loss.

Any corticosteroid suitable for administration via inhalation can be used according to the invention. Exemplary suitable corticosteroids are listed herein. Some embodiments of the invention comprise a corticosteroid having a lipophilicity approximating or exceeding that of flunisolide. Some embodiments of the invention exclude a corticosteroid having a lipophilicity less than flunisolide, i.e, embodiments excluding hydrocortisone, prednisolone, prednisone, dexamethasone, betamethasone, methylprednisolone, triamcinolone, fluocortolone.

One aspect of the invention provides a liquid formulation comprising an effective amount of corticosteroid, such as budesonide, and an SAE-CD, wherein the SAE-CD is present in an amount sufficient to dissolve and stabilize the corticosteroid during storage.

Another aspect of the invention provides a method of improving the administration of corticosteroid to a subject by nebulization, the method comprising the steps of:

providing in a unit dose an aqueous suspension formulation comprising water and corticosteroid suspended therein;

combining the suspension with an amount of SAE-CD sufficient to and for a period of time sufficient to solubilize the corticosteroid and form a solution; and administering the solution to the subject, wherein the amount of time required to administer a therapeutic dose of corticosteroid with the solution is less than the amount of time required to administer the same therapeutic dose of corticosteroid with the suspension under similar, or otherwise comparable, nebulization conditions.

When administered with a nebulizer, a suspension for nebulization will provide a first corticosteroid output rate under a first set of nebulization conditions. However, when SAE-CD is added to the suspension and mixed therein, a sufficient amount of the corticosteroid is dissolved to form a liquid formulation for nebulization that provides a greater corticosteroid output rate as compared to the formulation excluding the SAE-CD when administered under substantially the same conditions. In one embodiment, the drug output rate of the formulation is increased over that of the suspension even though the total volume of nebulized composition, i.e., the total volume of solution emitted by the nebulizer, has not increased. In another embodiment, SAE-CD is present in an amount sufficient to solubilize at least 50%, at least 75%, at least 90%, at least 95% or substantially all of the corticosteroid. Some embodiments of the invention include those wherein at least 50% wt., at least 75% wt., at least 90% wt., at least 95% wt., at least 98% wt., or all of the corticosteroid is dissolved in the inhalable liquid formulation.

In some embodiments, SAE-CD is present in an amount sufficient to decrease the amount of unsolubilized corticosteroid in the suspension formulation and to improve the administration of the suspension formulation via nebulization. In some embodiments, SAE-CD is present in an amount sufficient to solubilize enough corticosteroid such that the suspension formulation to which the SAE-CD was added is converted to a solution, substantially clear solution (containing less than 5% precipitate or solid), or a clear solution. It is possible that other components of the suspension formulation will not completely dissolve in, or may separate out from, the solution formulation containing SAE-CD.

According to some embodiments, a nebulizer charged with a corticosteroid/SAE-CD-containing solution generates smaller droplets than does the same nebulizer charged with a corticosteroid/HP-β-CD-containing solution operated under otherwise similar conditions. As a result of generating smaller droplets, the system comprising SAE-CD is improved over an otherwise similar system comprising HP-β-CD, since the SAE-CD based system will generate a greater proportion of respirable droplets and permit deeper lung penetration.

Some aspects of the invention provides for the use of SAE-CD in a nebulizable unit dose liquid formulation. In one embodiment, the invention provides use of SAE-CD for converting a nebulizable corticosteroid-containing suspension-based unit dose formulation to a nebulizable corticosteroid-containing liquid unit dose formulation.

Some embodiments of the invention include those wherein: 1) the corticosteroid to SAE-CD molar ratio is 0.5 to 0.0001 (1:2 to 1:10,000), 1:1 to 1:100, 1:1 to 1:10,000, or 0.1 (1:10) to 0.03 (1:33.33). The molar ratio of SAE-CD to corticosteroid in the formulation or system is generally greater than 10:1, greater than about 11:1, greater than 13:1, or greater than 14:1. Depending upon the corticosteroid used in the formulation, the molar ratio of corticosteroid to SAE-CD can vary in order to obtain a solution suitable for administration via inhalation for the treatment of a respiratory disease or disorder. In some embodiments, the nebulization composition comprises at least 4.8±0.5% wt./vol of SAE-CD to provide a self-preserved formulation for a period predetermined period of time. In some embodiments, the nebulization composition comprises less than or about 21.5±2% wt./wt. of SAE-CD. In some embodiments, the SAE-CD is present in an amount sufficient to provide a clear solution. For example, the nebulization composition can be visibly clear as viewed by the unaided eye.

Some suitable SAE-CD's include, for example, sulfobutyl ether 4-β-CD or sulfobutyl ether 7-β-CD, sulfobutyl ether 6-γ-CD, sulfobutyl ether 4-γ-CD, sulfobutyl ether 3 to 8-γ-CD, or a sulfobutyl ether 5-γ-CD, or a compound of the formula 1 or a mixture thereof.

A composition of the invention can further comprise a conventional preservative, an antioxidant, a buffering agent, an acidifying agent, a solubilizing agent, a complexation enhancing agent, saline, an electrolyte, another therapeutic agent, an alkalizing agent, a tonicity modifier, surface tension modifier, viscosity modifier, surfactant, density modifier, volatility modifier, or a combination thereof. If desired, the composition further comprises a liquid carrier other than water. If a conventional preservative is included in the composition, the corticosteroid, such as budesonide, may have a greater binding with the SAE-CD than does a conventional preservative. A composition can be purged with an inert gas prior to storage to remove substantially all of the oxygen contained in the formulation. In general, the formulation or composition of the invention has a shelf-life of at least 6 months depending upon the intended use.

The formulation can be prepared at a temperature at or above 5° C., at or above 25° C., at or above 35° C., at or above 45° C. or at or above 50° C. Specific embodiments of the methods of preparing a liquid formulation include those wherein: 1) the method further comprises the step of sterile filtering the formulation through a filtration medium having a pore size of 0.1 microns or larger; 2) the liquid formulation is sterilized by irradiation or autoclaving; 3) the nebulization solution is purged with nitrogen or argon or other inert pharmaceutically acceptable gas prior to storage such that a substantial portion of the oxygen dissolved in, and/or in surface contact with the solution is removed.

The invention provides a method of stabilizing corticosteroid in an aqueous corticosteroid-containing formulation comprising the step of adding SAE-CD to an aqueous corticosteroid-containing suspension of solution formulation in an amount sufficient to reduce the rate of degradation of corticosteroid as compared to a control sample excluding SAE-CD.

The invention also provides a method of improving the administration of an inhalable aqueous corticosteroid-containing suspension unit dose formulation by nebulization, the method comprising the step of adding SAE-CD to an aqueous corticosteroid-containing suspension unit dose formulation in an amount sufficient to solubilize the corticosteroid to form an inhalable aqueous corticosteroid-containing solution unit dose formulation, the improvement comprising increasing the output rate and/or extent of nebulized corticosteroid.

The invention provides a method of reducing the amount of time required to provide a therapeutically effective amount of corticosteroid to a subject by inhalation of an corticosteroid-containing composition with a nebulizer, the method comprising the steps of: including SAE-CD in the composition in an amount sufficient to solubilize the corticosteroid to form an inhalable aqueous corticosteroid-containing solution; and administering the solution to the subject by inhalation with a nebulizer, wherein the amount of time required to provide a therapeutically effective amount of corticosteroid to the subject with the solution is reduced as compared to the amount of time required to provide a therapeutically effective amount of corticosteroid to the subject with a corticosteroid-containing suspension comprising the same amount or concentration of corticosteroid when the suspension and solution are administered under otherwise similar nebulization conditions. In some embodiments, the time required to administer or deliver a dose of corticosteroid is less than 30 min, less than 20 min, less than 10 min, less than 7 min, less than 5 min, less than 3 min, or less than 2 min, or the time is about 0.05 to 10 min, about 0.1 to 5 min, about 0.1 to 3 min, about 0.1 to 2 min, about 0.1 to 1.5 min, about 0.5 min to about 1.5 min, or about 1 min, or about the time it takes for a subject to take a single breath (about 1 to 3 sec, or 1 to 5 sec). The time will vary according to the dose of corticosteroid in, the concentration of corticosteroid in, and the volume of the inhalable composition in the reservoir of a nebulizer, and it will also depend upon the nebulizer format, nebulization efficiency, and reservoir volume. In a given nebulizer, the lower the volume of the inhalable composition, the more quickly a corresponding dose of corticosteroid is nebulized. The higher the concentration of corticosteroid in an inhalable composition, the faster a dose of the corticosteroid can be administered or delivered.

The output rate (the rate at which the dose corticosteroid is administered or delivered) will vary according to the performance parameters of the nebulizer used to administer it. The higher the output rate of a given nebulizer, the lower the amount of time required to deliver or administer an inhalable composition, as defined herein, or dose of corticosteroid.

The invention also provides an inhalable composition comprising a water soluble γ-CD derivative, a corticosteroid (either esterified or unesterified) and an aqueous liquid medium. Another embodiment of the invention also provides an inhalable composition comprising a water soluble β-CD derivative, a corticosteroid (unesterified) and an aqueous liquid medium.

Also, the invention provides an improved system for administering a corticosteroid-containing inhalable formulation by inhalation, the improvement comprising including SAE-CD in the inhalable formulation such that SAE-CD is present in an amount sufficient to provide an increased rate of inhaled corticosteroid as compared to administration of a control inhalable formulation excluding SAE-CD but otherwise being administered under approximately the same conditions.

The invention can be used to provide a system for administration of a corticosteroid by inhalation, the system comprising an inhalation device, such as a nebulizer, and a drug composition comprising a therapeutically effective amount of corticosteroid, liquid carrier and SAE-CD present in an amount sufficient to solubilize the corticosteroid when presented to an aqueous environment, wherein the molar ratio of corticosteroid to SAE-CD is in the range of about 0.072 (1:13.89 or about 1:14) to 0.0001 (1:10,000) or 0.063 (1:15.873 or about 1:16) to 0.003 (1:333.33 or about 1:333). The molar ratio of SAE-CD to corticosteroid ranges from >10:1 to about 1000:1, about from >10:1 to about 100:1, from >10:1 to about 50:1, from >10:1 to about 30:1, from >10:1 to about 500:1. During operation, the system forms droplets having a MMAD in the range of about 1-8μ or 3-8μ. The corticosteroid is delivered at a rate, of at least about 20-50 μg/min, wherein this range may increase or decrease according to the concentration of corticosteroid in the nebulization solution in the reservoir of the nebulizer.

As a result of using SAE-CD corticosteroid therapy with an inhalable nebulization solution, one can expect advantages such as enhanced drug delivery, enhanced delivery especially to the peripheral or small airways facilitated by the finer aerosol produced, potentially improved treatment of nocturnal, asymptomatic asthma and recovery from acute asthma attacks, increased rate of drug administration, enhanced pharmacokinetic profile, reduced treatment time, improved formulation stability and/or improved patient compliance as compared to comparable corticosteroid therapy with an inhalable nebulization suspension or suspension chlorofluorocarbon (CFC) or hydrofluoroalkanes (HFA) pressurized metered-dose inhaler (pMDI).

The invention can be employed in a kit comprising SAE-CD, an aqueous carrier, and corticosteroid, wherein the kit is adapted for the preparation of a nebulization solution. Embodiments of the kit are detailed below. The invention provides the potential to accommodate combination products to overcome incompatibilities with suspension by other solution dosage forms.

The liquid formulation and composition of the invention provide an enhanced bioavailability/bioabsorption of the corticosteroid as compared to a suspension-based aqueous formulation containing approximately the same amount of corticosteroid and excluding SAE-CD. The liquid formulation or composition provides a higher ratio of AUCi (or AUCt) to amount of budesonide delivered to a subject than does the suspension based formulation. Thus, the liquid formulation and/or composition provides an improved clinical benefit or therapeutic benefit over the suspension-based formulation.

The invention also provides a method of administering a corticosteroid to a subject comprising the step of administering via inhalation to a subject an aqueous liquid composition comprising a unit dose of corticosteroid dissolved therein, wherein the composition provides a mean AUCt, normalized for dose of the corticosteroid, of at least 6 (pg*h/ml) per μg of corticosteroid administered. In some embodiments, the unit dose comprises at least 45 μg, at least 48 μg, 45-1000 μg, about 1 μg to 20 mg, about 1 μg to 10 mg, 0.01 mg to 10 mg, 0.025 mg to 10 mg, 0.05 mg to 5 mg, 0.1 mg to 5 mg, 0.125 mg to 5 mg, 0.25 mg to 5 mg, 0.5 mg to 5 mg, 0.05 mg to 2 mg, 0.1 mg to 2 mg, 0.125 mg to 2 mg, 0.25 mg to 2 mg, 0.5 mg to 2 mg, 1 μg, 10 μg, 25 μg, 50 μg, 100 μg, 125 μg, 200 μg, 250 μg, 25 to 66 μg, 48 to 81 μg, 73 to 125 μg, 40 μg, 64 μg, 95 μg, 35 to 95 μg, 25 to 125 μg, 60 to 170 μg, 110 μg, 170 μg, 45 to 220 μg, 45 to 85 μg, 48 to 82 μg, 85 to 160 μg, 140 to 220 μg, 120 to 325 μg, 205 μg, 320 μg, 325 μg, 90 to 400 μg, 95 to 170 μg, 165 to 275 μg, or 275 to 400 μg of corticosteroid. In some embodiments, the normalized AUCt is based upon the dose to subject, the normalized AUCt is based upon the dose to lung of subject, or the normalized AUCt is based upon the emitted dose or nominal dose. As used herein, AUCt (or $AUC_{last}$, $AUC_{0-t}$) is the area under the plasma level versus time curve to the last time point t for which there is a quantifiable value.

The invention also provides a method of administering a corticosteroid to a subject comprising the step of administering via inhalation to a subject an aqueous liquid composition comprising a unit dose of corticosteroid dissolved therein, wherein the composition provides a mean AUCi, normalized for dose of the corticosteroid, of at least 8 (pg*h/ml) per μg of corticosteroid administered. In some embodiments, the unit dose comprises at least 45 μg, at least 48 μg, or 45-1000 μg, about 1 μg to 20 mg, about 1 μg to 10 mg, 0.01 mg to 10 mg, 0.025 mg to 10 mg, 0.05 mg to 5 mg, 0.1 mg to 5 mg, 0.125 mg to 5 mg, 0.25 mg to 5 mg, 0.5 mg to 5 mg, 0.05 mg to 2 mg, 0.1 mg to 2 mg, 0.125 mg to 2 mg, 0.25 mg to 2 mg, or 0.5 mg to 2 mg of corticosteroid. In some embodiments, the normalized AUCi is based upon the dose to subject, the normalized AUCi is based upon the dose to lung of subject, or the normalized AUCi is based upon the emitted dose or nominal dose. As used herein, the AUCi ($AUC_{inf}$, $AUC_{(0-\infty)}$) is the AUC extrapolated to infinity.

When the aqueous liquid solution formulation of the invention is administered via inhalation it can provide at least a two-fold increase in the AUCt or AUCi, normalized for dose of the corticosteroid, per microgram of corticosteroid administered as compared to administration via inhalation of an aqueous liquid suspension formulation comprising substantially the same amount of corticosteroid suspended therein. In some embodiments, the formulation provides at least a 1.6 to five-fold (range as determined on an individual subject basis or a mean of 3 with a standard deviation of +/−1 as determined from the individual subject data) or a two to four-fold increase (as determined using the geometric mean across a patient population) in the AUCt or AUCi, normalized for dose of the corticosteroid, per microgram of corticosteroid administered. The basis for amount of "corticosteroid administered" can be "dose to subject" or "dose to lung" or "emitted dose" or "nominal dose" or "nominal available dose" or "loaded dose".

The aqueous liquid formulation can be administered with any type of device suitable for administration of a liquid formulation to the lung. For example, the formulation can be administered with an air driven jet, ultrasonic, capillary, electromagnetic, pulsating membrane, pulsating plate (disc), pulsating mesh nebulizer, a nebulizer comprising a vibration generator and an aqueous chamber, and a nebulizer comprising a nozzle array.

In some embodiments, the invention provides a system comprising a nebulizer and an aqueous liquid formulation/composition as described herein. When charged with a liquid formulation of the invention comprising a dose of corticosteroid, the nebulizer can provide a decreasing rate of increasing concentration (RIC) of corticosteroid in the formulation in the reservoir of the nebulizer, in particular when comparing the performance of the liquid formulation to the performance of a suspension-based formulation, e.g. PULMICORT RESPULES, in the nebulizer. In some embodiments, the percentage decrease in the RIC ranges from 10% to 60%, 15% to 60%, 20% to 60%, 30% to 60%, or 40% to 60%. In some embodiments, the system may provide a RIC of 0 to 40, 1 to 40, 5 to 30, or 10 to 30 mcg of corticosteroid/mL of solution volume per min of operation/nebulization.

The pharmacokinetic enhancement provided by the system and formulation/composition of the invention can be determined by comparison of Cmax, AUC and Tmax parameters. In some embodiments, the formulation and system of the invention can provide a $C_{max}$ (pg of corticosteroid/ml) of 90 to 900, 200 to 600, 200 to 550, 200 to 250, 400 to 450, 500 to 600, 225, 437, or 545 on a dose non-normalized basis. The formulation and system of the invention can provide a dose normalized $C_{max}$ (pg/ml/μg) of: 1) 0.3 to 2, 0.35 to 2, 0.6 to 1.5, 0.5 to 1.2, 0.8 to 1, 0.8 to 0.9, 0.7 to 0.8, 0.4, 1.9, 0.6, 1.5, 0.5, 1.2, 0.35, 2, 0.7, 0.8, or 0.9 on a nominal available dose normalized basis; 2) 3.4 to 9.2, 3.5 to 8.5, 5.5 to 9.2, 4.5 to 7.5, 5.8 to 7, 3.4, 3.5, 4.5, 5.5, 9.2, 8.5, 7.5, 5.8, 5.9, 6, or 7 on a dose to lung normalized basis; 3) 1.7 to 7.5, 3.2 to 4.1, 1.9 to 6, 3.2 to 7.5, 1.7 to 5.2, 3.6, 4.1, 3.2, 1.9, 6, 3.2, 7.4, 7.5, 1.7, 5.2 or 5.3 on a dose to subject normalized basis; 4) 0.9 to 3.3, 1.7 to 2.2, 0,9 to 3, 1 to 3, 1.7 to 3.3, 1 to 2.7, 1.9, 2.1, 2.2, 1.7, 0.9, 1, 2, 3, 2.9, 3, 2, 3.3, or 2.7 on an emitted dose normalized basis.

In some embodiments, on the basis of the non-normalized dose of corticosteroid, the Cmax provided by the corticosteroid solution is 1.6 to 2, 1.5 to 3, 1.5 to 2.5, 1.5 to 2, 1.5, 1.6, 2, 2.5, or 3 fold higher than the Cmax provided by the suspension-based formulation when the dose of corticosteroid in the solution and the suspension is approximately the same amount loaded. On the basis of normalization to the nominal available dose of corticosteroid, the Cmax provided by the corticosteroid solution is 1.8 to 6.2, 1.5 to 6.5, 2 to 6.5, 1.5 to 5.5, 2 to 4, 1.5 to 4, 1.5 to 3, 2.7, 3.3, 3.4, 1.5, 6.5, 2, 5.5, 4, or 3 fold higher than the Cmax provided by the suspension-based formulation. On the basis of normalization to the dose of corticosteroid to lung, the Cmax provided by the corticosteroid solution is 1.4 to 4.3, 1.4 to 4.5, 1.5 to 4.5, 1.5 to 3.5, 1.5 to 3, 1.4 to 3, 1.5 to 2.5, 1.5 to 2, 2, 2.3, 1.4, 4.5, 3.5, 3, 1.5 or 2.5 fold higher than the Cmax provided by the suspension-based formulation. On the basis of normalization to the dose of corticosteroid to subject, the Cmax provided by the corticosteroid solution is 2 to 3.5, 2 to 5, 1.7 to 3.8, 1.7 to 5, 2.7, 3, 2.4, 2, 3.5, 5, 1.7, or 3.8 fold higher than the Cmax provided by the suspension-based formulation. On the basis of normalization to the emitted dose of corticosteroid, the Cmax provided by the corticosteroid solution is 1.9 to 6.3, 1.75 to 6.5, 2.2 to 4.2, 2.2 to 6.3, 1.9 to 4.2, 3.2, 3.5, 3.6, 2.8, 1.75, 6.5, 2.2, 4.2, or 6.3 fold higher than the Cmax provided by the suspension-based formulation.

In some embodiments, the Cmax provided by the corticosteroid solution is at least 1.5, 1.6, 2, 2.6, and 3 fold higher than the Cmax provided by the suspension-based formulation when the dose of corticosteroid in the solution is about 2 fold lower than the dose in the suspension.

In some embodiments, the formulation and system of the invention can provide an $AUC_{inf}$ (pg*h/ml) of 500 to 1700, 530 to 1650, 250 to 2500, 280 to 1300, 780 to 1300, 980 to 2450, 275, 775, 980, 2400, 2500, 1300, 1290, 530, 1650, 250, 280 or 780 on a dose non-normalized basis. The formulation and system of the invention can provide a dose normalized $AUC_{inf}$ (pg/ml/μg) of: 1) 1 to 5.5, 2 to 2.2, 1 to 5.3, 1.1 to 5.2, 1.5 to 2.6, 1.3 to 3.3, 2, 2.1, 2.2, 1, 5.5, 5.3, 5.2, 1.5, 2.6, 1.3 or 3.3 on a nominal available dose normalized basis; 2) 10 to 25, 14 to 18, 10.2 to 20, 13.6 to 18.8, 11.2 to 24.7, 10.2, 20, 13.6, 14, 19, 18.8, 11, 11.2, 25, 24.7, 14.2, 16.2, 17.3 on a dose to lung normalized basis; 3) 4 to 16, 4.2 to 16.1, 8 to 12.2, 5.4 to 16, 5.4 to 17, 8.5 to 9.6, 8.5, 9.5, 9.6, 4.2, 16.1, 8, 12.2, 12, 5.4, 16, 17, or 16.5 on a dose to subject normalized basis; 4) 2.5 to 9, 2.6 to 8.5, 4.5 to 5.1, 2.5 to 8, 2.6 to 7.9, 4.2 to 6.7, 3.1 to 8.5, 3.2 to 8.5, 4.5, 4.6, 5, 5.1, 2.5, 2.6, 4.2, 3.1, 9, 8.5, 5.1, 8, 7.9, or 6.7 to on an emitted dose normalized basis.

In some embodiments, on the basis of the non-normalized dose of corticosteroid, the $AUC_{inf}$ provided by the corticosteroid solution is 1.6 to 2.5, 1.6 to 3.1, 1.5 to 3.5, 1.5 to 3.3, 2.5 to 3.3, 3.1, 1.5, 3.3, 1.6, or 2.5 fold higher than the $AUC_{inf}$ provided by the suspension-based formulation when the dose of corticosteroid in the solution and the suspension is approximately the same. On the basis of normalization to the nominal available dose of corticosteroid, the $AUC_{inf}$ provided by the corticosteroid solution is 1.75 to 6.5, 1.75 to 6.1, 2 to 6.5, 2 to 6.1, 2 to 4.5, 2 to 4.4, 3.3, 3.2, 3.5, 3.4, 1.75, 6.5, 6.1, 2, 4.5, or 4.4 fold higher than the $AUC_{inf}$ provided by the suspension-based formulation. On the basis of normalization to the dose of corticosteroid to lung, the $AUC_{inf}$ provided by the corticosteroid solution is 1.2 to 3.5, 1.2 to 4, 1.2 to 3, 1.2 to 2.85, 1.5 to 3.5, 1.4 to 3.5, 2, 2.2, 2.3, 2.4, 1.2, 3, 4, 2.85, 1.5, 3.5, or 1.4 fold higher than the $AUC_{inf}$ provided by the suspension-based formulation. On the basis of normalization to the dose of corticosteroid to subject, the $AUC_{inf}$ provided by the corticosteroid solution is 1.6 to 4.9, 1.5 to 5, 1.6 to 5, 1.6 to 3.7, 1.6 to 3.6, 2 to 4.9, 1.9 to 4, 2.6, 1.5, 5, 1.6, 3.7, 3.6, 2, 4.9, 1.9, or 4 fold higher than the $AUC_{inf}$ provided by the suspension-based formulation. On the basis of normalization to the emitted dose of corticosteroid, the $AUC_{inf}$ provided by the corticosteroid solution is 1.5 to 6, 1.7 to 6, 1.9 to 6, 1.9 to 5.4, 2.3 to 5.8, 1.9 to 5.5, 1.9 to 5.8, 1.5, 6, 1.7, 1.9, 5.4, 2.3, 5.8, 5.8, 3.2, 3.5, or 3.6 fold higher than the $AUC_{inf}$ provided by the suspension-based formulation.

In some embodiments, the $AUC_{inf}$ provided by the corticosteroid solution is at least 1.5, 1.6, 2, 2.5, 3 and 3.1 fold higher than the $AUC_{inf}$ provided by the suspension-based formulation when the dose of corticosteroid in the solution is about 2 fold lower than the dose in the suspension.

The formulation and system of the invention can provide an $AUC_{0-8\ hr}$ (pg*h/ml) of 2000 to 3000, 2500 to 2700, 2000, 3000, or 2600 on a dose non-normalized basis for the corticosteroid. The formulation and system of the invention can provide a dose normalized $AUC_{inf}$ (pg/ml/µg) of: 1) 2 to 3, 2.5 to 2.7, or 2.6 on a loaded dose nominal normalized basis for the corticosteroid; 2) 3 to 4, 3.4 to 3.5, or 3.4 on an emitted dose normalized basis for the corticosteroid.

In some embodiments, on the basis of the normalized nominal (loaded) dose of corticosteroid, the $AUC_{0-8}hr$ provided by the corticosteroid solution is at least 1.7, 1.8, 1.9, or 2 fold higher than the $AUC_{0-8\ hr}$ provided by the suspension-based formulation when the dose of corticosteroid in the solution and the suspension is approximately the same. On the basis of normalization to the emitted dose of corticosteroid, the $AUC_{0-8\ hr}$ provided by the corticosteroid solution is at least 1.5, 1.6, to 2 fold higher than the $AUC_{0-8\ hr}$ provided by the suspension-based formulation.

The formulation and system of the invention can provide a $C_{max}$ (pg/ml) of 1600 to 1800, 1650 to 1750, or 1700 on a dose non-normalized basis. The formulation and system of the invention can provide a dose normalized $C_{max}$ (pg/ml/µg) of: 1) 1 to 2, 1.6 to 1.8, or 1.7 on a loaded dose nominal normalized basis; 2) 2 to 2.5, or 2.2 on an emitted dose normalized basis.

In some embodiments, on the basis of the normalized nominal (loaded) dose of corticosteroid, the $C_{max}$ provided by the corticosteroid solution is at least 1.7, 1.8, 1.9, or 2 fold higher than the $C_{max}$ provided by the suspension-based formulation when the dose of corticosteroid in the solution and the suspension is approximately the same. On the basis of normalization to the emitted dose of corticosteroid, the $C_{max}$ provided by the corticosteroid solution is at least 1.5, 1.6, to 2 fold higher than the $C_{max}$ provided by the suspension-based formulation.

In some embodiments, greater than 20%, greater than 25%, greater than 29%, greater than 35% of the emitted dose may be absorbed into the bloodstream of the patient. In some embodiments, greater than 40%, greater than 50%, greater than 55% of the dose to subject may be absorbed into the bloodstream of the patient. In some embodiments, greater than 10%, greater than 12%, greater than 15% of the nominal available dose may be absorbed into the bloodstream of the patient.

Some aspects of the invention provide a method of administering or delivering a dose of corticosteroid to the air passageways of a subject in need thereof, the method comprising administering or delivering the corticosteroid with a nebulizer comprising a charge of an aqueous liquid formulation, the formulation comprising an aqueous liquid carrier, sulfoalkyl ether cyclodextrin, and the corticosteroid dissolved therein, wherein, during operation, the system provides enhanced drug delivery, increased rate of drug administration, reduced treatment time, reduced toxicity, improved stability, enhanced bioabsorption, increased output rate, increased total output, enhanced pharmacokinetic profile, reduced corticosteroid-related side effects, enhanced pulmonary deposition, reduced oropharyngeal deposition, and/or improved nebulization performance over another system comprising the nebulizer and a suspension based formulation of the corticosteroid. The systems can be operated under similar conditions or dissimilar conditions.

The invention includes all combinations of the embodiments and aspects disclosed herein. Accordingly, the invention includes the embodiments and aspects specifically disclosed, broadly disclosed, or narrowly disclosed herein, as well as combinations thereof and subcombinations of the individual elements of said embodiments and aspects.

These and other aspects of this invention will be apparent upon reference to the following detailed description, examples, claims and attached figures.

BRIEF DESCRIPTION OF THE FIGURES

The following drawings are given by way of illustration only, and thus are not intended to limit the scope of the present invention.

FIG. 1 depicts a graph of the hemolytic behavior of the CAPTISOL® as compared to the same for the parent β-cyclodextrin, the commercially available hydroxypropyl derivatives, ENCAPSIN™ (degree of substitution ~3-4) and MOLECUSOL® (degree of substitution ~7-8), and two other sulfobutyl ether derivatives, SBE1-β-CD and SBE4-β-CD.

FIG. 2 depicts a graph of the osmolality of SBE-CD containing solutions of various degrees of substitution and HP-β-CD containing solutions comprising similar concentrations of cyclodextrin derivative.

FIG. 3 depicts a phase solubility graph of the concentration (molar) of cyclodextrin versus the concentration (molar) of budesonide for γ-CD, HP-β-CD and SBE7-β-CD.

FIG. 4 depicts a chart of the estimated percentage of nebulization composition emitted from three different nebulizers (PARI LC PLUS, HUDSON UPDRAFT II NEB-U-MIST, and MYSTIQUE) for each of four different nebulization compositions (PULMICORT RESPULES suspension, 5% w/v SBE7-β-CD solution, 10% w/v SBE7-β-CD solution and 20% w/v SBE7-β-CD solution).

FIGS. 5*a*-5*b* depict droplet size data for nebulization of solutions with a PARI LC PLUS nebulizer.

FIG. 6 depicts droplet size data for nebulization of solutions with a HUDSON UPDRAFT II NEBUMIST nebulizer.

FIG. 7 depicts droplet size data for nebulization of solutions with a MYSTIQUE ultrasonic nebulizer.

FIG. 8 depicts comparative $Dv_{50}$ droplet size data for nebulization of composition with the three nebulizers PARI LC PLUS, HUDSON UPDRAFT II NEBUMIST, and MYSTIQUE.

FIG. 9 is a graph depicting the relationship between concentration of SAE-CD versus output rate of SAE-CD in various different nebulizers.

FIGS. 10*a*-10*b* depict comparative droplet size data for nebulization solutions with the PARI LC PLUS and MYSTIQUE nebulizers of PULMICORT RESPULES suspension and a modified PULMICORT RESPULES-based SAE-CD solution.

FIG. 11 depicts a semi-log plot of the % of initial concentration of the R- and S-isomers of budesonide in solutions with and without CAPTISOL versus time at 60° C. in solution.

FIG. 12 depicts a semi-log plot of the % of initial concentration of budesonide versus Lux hours when the samples are exposed to fluorescent lamps.

FIG. 13 depicts a phase solubility diagram for fluticasone propionate in the presence of several different cyclodextrins.

FIG. 14 depicts a phase solubility diagram for mometasone furoate in the presence of several different cyclodextrins.

DETAILED DESCRIPTION OF THE INVENTION

Figure 1:
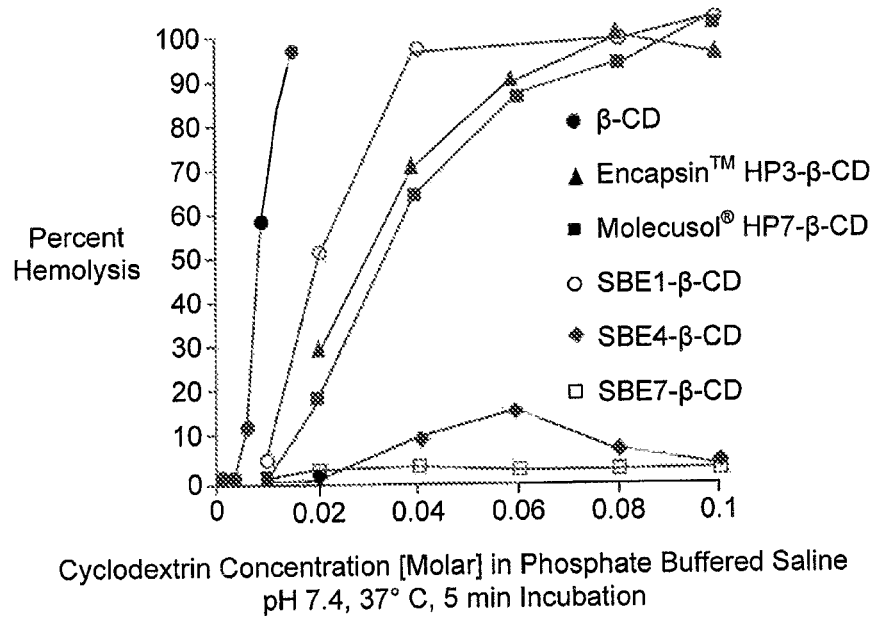
Figure 2:
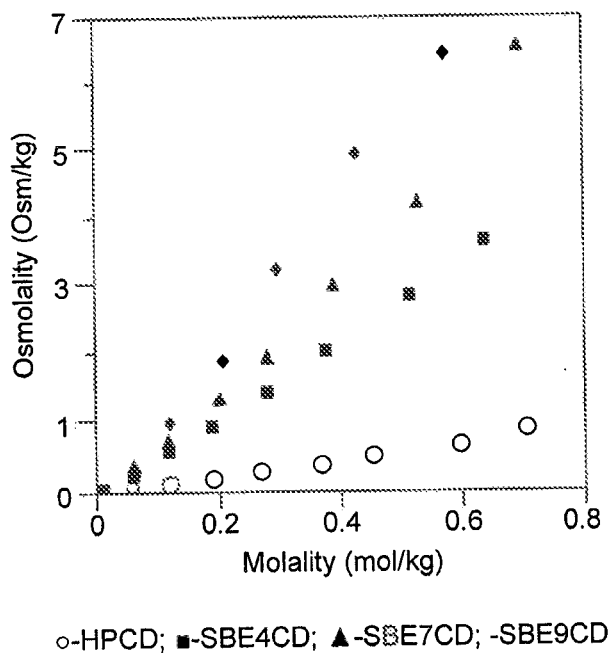

The presently claimed formulation overcomes many of the undesired properties of other known aqueous inhalable solution or suspension corticosteroid-containing formulations. By including SAE-CD, in an inhalable liquid formulation containing corticosteroid, the corticosteroid is dissolved. Unexpectedly, the nebulization of corticosteroid is improved in both an air driven jet nebulizer and an ultrasonic nebulizer. Moreover, the corticosteroid exhibits greater stability in the presence of SAE-CD than it does in its absence.

The inhalable formulation and system of the invention provides an improved pharmacokinetic profile over a suspension formulation comprising approximately the same amount of corticosteroid and delivered under substantially the same conditions. The term "enhanced pharmacokinetic profile" is taken to mean a higher AUC (e.g. $AUC_{last}$ or $AUC^{(0\rightarrow\infty)}$ per μg of corticosteroid delivered or administered, a higher Cmax per μg of corticosteroid delivered or administered, increased bioavailability, absorption or distribution of the corticosteroid at the site of delivery, a shorter Tmax or a longer Tmax.

Alternatively, the inhalable formulation and system of the invention provides substantially the same pharmacokinetic profile or an enhanced pharmacokinetic profile over a suspension formulation comprising approximately a higher amount of corticosteroid and delivered under substantially the same conditions. The corticosteroid in the formulation can be present at a dose that is less than 80%, less than 70% less than 60% less than 50%, less than 40%, less than 20%, and less than 10% of that in the suspension.

The corticosteroid can be present in an amount sufficient for single dose or multi-dose administration. SAE-CD can be present in an amount sufficient to solubilize the corticosteroid when the two are placed in the aqueous carrier. The aqueous carrier can be present in an amount sufficient to aid in dissolution of the corticosteroid and form a nebulization solution of sufficient volume and sufficiently low viscosity to permit single dose or multi-dose administration with a nebulizer. SAE-CD can be present in solid form or in solution in the aqueous carrier. The corticosteroid can be present in dry powder/particle form or in suspension in the aqueous carrier.

Commercially available air driven jet, ultrasonic or pulsating membrane nebulizers include the AERONEB™ (Aerogen, San Francisco, Calif.), AERONEB GO (Aerogen); PARI LC PLUS™, PARI BOY™ N, PARI eflow, PARI LC SINUS, PARI SINUSTAR™, PARI SINUNEB, and PARI DURANEB™ (PARI Respiratory Equipment, Inc., Monterey, Calif.); MICROAIR™ (Omron Healthcare, Inc, Vernon Hills, Ill.), HALOLITE™ (Profile Therapeutics Inc, Boston, Mass.), RESPIMAT™ (Boehringer Ingelheim Ingelheim, Germany) AERODOSE™ (Aerogen, Inc, Mountain View, Calif.), OMRON ELITE™ (Omron Healthcare, Inc, Vernon Hills, Ill.), OMRON MICROAIR™ (Omron Healthcare, Inc, Vernon Hills, Ill.), MABISMIST™ II (Mabis Healthcare, Inc, Lake Forest, Ill.), LUMISCOPE™ 6610, (The Lumiscope Company, Inc, East Brunswick, N.J.), AIRSEP MYSTIQUE™, (AirSep Corporation, Buffalo, N.Y.), ACORN-1 and ACORN-II (Vital Signs, Inc, Totowa, N.J.), AQUATOWER™ (Medical Industries America, Adel, Iowa), AVA-NEB (Hudson Respiratory Care Incorporated, Temecula, Calif.), AEROCURRENT™ utilizing the AEROCELL™ disposable cartridge (AerovectRx Corporation, Atlanta, Ga.), CIRRUS (Intersurgical Incorporated, Liverpool, N.Y.), DART (Professional Medical Products, Greenwood, S.C.), DEVILBISS™ PULMO AIDE (DeVilbiss Corp; Somerset, Pa.), DOWNDRAFT™ (Marquest, Englewood, Colo.), FAN JET (Marquest, Englewood, Colo.), MB-5 (Mefar, Bovezzo, Italy), MISTY NEB™ (Baxter, Valencia, Calif.), SALTER 8900 (Salter Labs, Arvin, Calif.), SIDESTREAM™ (Medic-Aid, Sussex, UK), UPDRAFT-II™ (Hudson Respiratory Care; Temecula, Calif.), WHISPER JET™ (Marquest Medical Products, Englewood, Colo.), AIOLOS™ (Aiolos Medicnnsk Teknik, Karlstad, Sweden), INSPIRON™ (Intertech Resources, Inc., Bannockburn, Ill.), OPTIMIST™ (Unomedical Inc., McAllen, Tex.), PRODOMO™, SPIRA™ (Respiratory Care Center, Hameenlinna, Finland), AERx™ Essence™ and Ultra™, (Aradigm Corporation, Hayward, Calif.), SONIK™ LDI Nebulizer (Evit Labs, Sacramento, Calif.), and SWIRLER® Radioaerosol System (AMICI, Inc., Spring City, Pa.). Nebulizers that nebulize liquid formulations containing no propellant are suitable for use with the compositions provided herein. Any of these and other known nebulizers can be used to deliver the formulation of the invention including but not limited to the following: nebulizers available from Pari GmbH (Starnberg, Germany), DeVilbiss Healthcare (Heston, Middlesex, UK), Healthdyne, Vital Signs, Baxter, Allied Health Care, Invacare, Hudson, Omron, Bremed, AirSep, Luminscope, Medisana, Siemens, Aerogen, Mountain Medical, Aerosol Medical Ltd. (Colchester, Essex, UK), AFP Medical (Rugby, Warwickshire, UK), Bard Ltd. (Sunderland, UK), Carri-Med. Ltd. (Dorking, UK), Plaem Nuiva (Brescia, Italy), Henleys Medical Supplies (London, UK), intersurgical (Berkshire, UK), Lifecare Hospital Supplies (Leies, UK), Medic-Aid Ltd. (West Sussex, UK), Medix Ltd. (Essex, UK), Sinclair Medical Ltd. (Surrey, UK), and many other companies. The AERx and RESPIMAT nebulizers are described by D. E. Geller (*Respir. Care* (2002), 47 (12), 1392-1404), the entire disclosure of which is incorporated by reference.

Nebulizers for use herein include, but are not limited to, jet nebulizers (optionally sold with compressors), ultrasonic nebulizers, vibrating membrane, vibrating mesh nebulizers, vibrating plate nebulizers, vibrating cone nebulizer, and others. Exemplary jet nebulizers for use herein include Pari LC plus/ProNeb, Pari LC plus/ProNeb Turbo, Pari LC Plus/Dura Neb 1000 & 2000 Pari LC plus/Walkhaler, Pari LC plus/Pari Master, Pari LC star, Omron CompAir XL Portable Nebulizer System (NE-C18 and JetAir Disposable nebulizer), Omron compare Elite Compressor Nebulizer System (NE-C21 and Elite Air Reusable Nebulizer, Pari LC Plus or Pan LC Star nebulizer with Proneb Ultra compressor, Pulomo-aide, Pulmo-aide LT, Pulmo-aide traveler, Invacare Passport, Inspiration Healthdyne 626, Pulmo-Neb Traverler, DeVilbiss 646, Whisper Jet, Acorn II, Misty-Neb, Allied aerosol, Schuco Home Care, Lexan Plasic Pocet Neb, Side-Stream Hand Held Neb, Mobil Mist, Up-Draft, Up-Draft II, T Up-Draft, ISO-NEB, Ava-Neb, Micro Mist, and Pulmo-Mate. Exemplary ultrasonic nebulizers for use herein include MicroAir, UltraAir, Siemens Ultra Nebulizer 145, CompAir, Pulmosonic, Scout, 5003 Ultrasonic Neb, 5110 Ultrasonic Neb, 5004 Desk Ultrasonic Nebulizer, Mystique Ultrasonic, Lumiscope's Ultrasonic Nebulizer, Medisana Ultrasonic Nebulizer, Microstat Ultrasonic Nebulizer, and Mabismist Hand Held Ultrasonic Nebulizer. Other nebulizers for use herein include 5000 Electromagnetic Neb, 5001 Electromagnetic Neb 5002 Rotary Piston Neb, Lumineb I Piston Nebulizer 5500, Aeroneb Portable Nebulizer System, Aerodose™ Inhaler, and AeroEclipse Breath Actuated Nebulizer. Exemplary vibrating membrane, mesh or plate nebulizers are described by R. Dhand (*Respiratory Care*, (December 2002), 47(12), p. 1406-1418), the entire disclosure of which is hereby incorporated by reference.

Other suitable nebulizers are described in U.S. Pat. No. 5,954,047, No. 6,026,808, No. 6,095,141, and No. 6,527,151, the entire disclosures of which are hereby incorporated by reference.

The present invention provides SAE-CD based formulations, wherein the SAE-CD is a compound of the Formula 1:

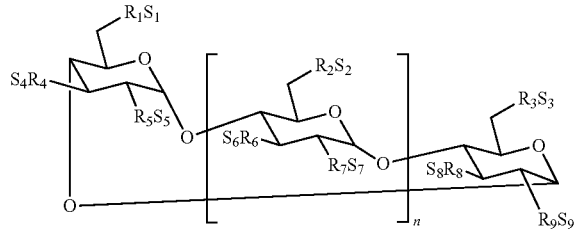

Formula 1 wherein:

n is 4, 5 or 6;

$R_1$, $R_2$, $R_3$, $R_4$, $R_5$, $R_6$, $R_7$, $R_8$ and $R_9$ are each, independently, —O— or a —O—$(C_2$-$C_6$ alkylene)-$SO_3^-$ group, wherein at least one of $R_1$ to $R_9$ is independently a —O—$(C_2$-$C_6$ alkylene)-$SO_3^-$ group, preferably a —O—$(CH_2)_m SO_3^-$ group, wherein m is 2 to 6, preferably 2 to 4, (e.g. —$OCH_2CH_2CH_2SO_3^-$ or —$OCH_2CH_2CH_2CH_2SO_3$); and $S_1$, $S_2$, $S_3$, $S_4$, $S_5$, $S_6$, $S_7$, $S_8$ and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of $(C_1$-$C_6)$-alkylamines, piperidine, pyrazine, $(C_1$-$C_6)$-alkanolamine and $(C_4$-$C_8)$-cycloalkanolamine.

Exemplary embodiments of the SAE-CD derivative of the invention include derivatives of the Formula II (SAEx-α-CD), wherein "x" ranges from 1 to 18; of the Formula III (SAEy-β-CD), wherein "y" ranges from 1 to 21; and of the Formula IV (SAEz-γ-CD), wherein "z" ranges from 1 to 24 such as:

| SAEx-α-CD | SAEy-β-CD | SAEz-γ-CD | Name |
|---|---|---|---|
| SEEx-α-CD | SEEy-β-CD | SEEz-γ-CD | Sulfoethyl ether CD |
| SPEx-α-CD | SPEy-β-CD | SPEz-γ-CD | Sulfopropyl ether CD |
| SBEx-α-CD | SBEy-β-CD | SBEz-γ-CD | Sulfobutyl ether CD |
| SptEx-α-CD | SPtEy-β-CD | SPtEz-γ-CD | Sulfopentyl ether CD |
| SHEx-α-CD | SHEy-β-CD | SHEz-γ-CD | Sulfohexyl ether CD |

"SAE" represents a sulfoalkyl ether substituent bound to a cyclodextrin. The values "x", "y" and "z" represent the average degree of substitution as defined herein in terms of the number of sulfoalkyl ether groups per CD molecule.

The SAE-CD used is described in U.S. Pat. No. 5,376,645 and No. 5,134,127 to Stella et al, the entire disclosures of which are hereby incorporated by reference. U.S. Pat. No. 3,426,011 to Parmerter et al. discloses anionic cyclodextrin derivatives having sulfoalkyl ether substituents. Lammers et al. (*Recl. Trav. Chim. Pays-Bas* (1972), 91(6), 733-742); *Staerke* (1971), 23(5), 167-171) and Qu et al. (*J. Inclusion Phenom. Macro. Chem.*, (2002), 43, 213-221) disclose sulfoalkyl ether derivatized cyclodextrins. U.S. Pat. No. 6,153,746 to Shah et al. discloses a process for the preparation of sulfoalkyl ether cyclodextrin derivatives. An SAE-CD can be made according to the disclosures of Stella et al., Parmerter et al., Lammers et al. or Qu et al., and if processed to remove the major portion (>50%) of the underivatized parent cyclodextrin, used according to the present invention. The SAE-CD can contain from 0% to less than 50% wt. of underivatized parent cyclodextrin.

The terms "alkylene" and "alkyl," as used herein (e.g., in the —O—$(C_2$-$C_6$alkylene)$SO_3^-$ group or in the alkylamines), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl)cyclic alcohols.

An embodiment of the present invention provides compositions containing a mixture of cyclodextrin derivatives, having the structure set out in formula (I), where the composition overall contains on the average at least 1 and up to 3n+6 alkylsulfonic acid moieties per cyclodextrin molecule. The present invention also provides compositions containing a single type of cyclodextrin derivative, or at least 50% of a single type of cyclodextrin derivative. The invention also includes formulations containing cyclodextrin derivatives having a narrow or wide and high or low degree of substitution. These combinations can be optimized as needed to provide cyclodextrins having particular properties.

The present invention also provides compositions containing a mixture of cyclodextrin derivatives wherein two or more different types of cyclodextrin derivatives are included in the composition. By different types, is meant cyclodextrins derivatized with different types of functional groups e.g., hydroxyalkyl and sulfoalkyl. Each independent different type can contain one or more functional groups, e.g. SBE-CD where the cyclodextrin ring has only sulfobutyl functional groups, and hydroxypropyl-ethyl-β-CD where the cyclodextrin ring has both hydroxypropyl functional groups and ethyl functional groups. The amount of each type of cyclodextrin derivative present can be varied as desired to provide a mixture having the desired properties.

Exemplary SAE-CD derivatives include SBE4-β-CD, SBE7-β-CD, SBE11-β-CD, SBE3.4-γ-CD, SBE4.2-γ-CD, SBE4.9-γ-CD, SBE5.2-γ-CD, SBE6.1-γ-CD, SBE7.5-γ-CD, SBE7.8-γ-CD and SBE5-γ-CD which correspond to SAE-CD derivatives of the formula wherein n=5, 5, 5 and 6; m is 4; and there are on average 4, 7, 11 and 5 sulfoalkyl ether substituents present, respectively. These SAE-CD derivatives increase the solubility of poorly water soluble active agents to varying degrees.

Figure 13:
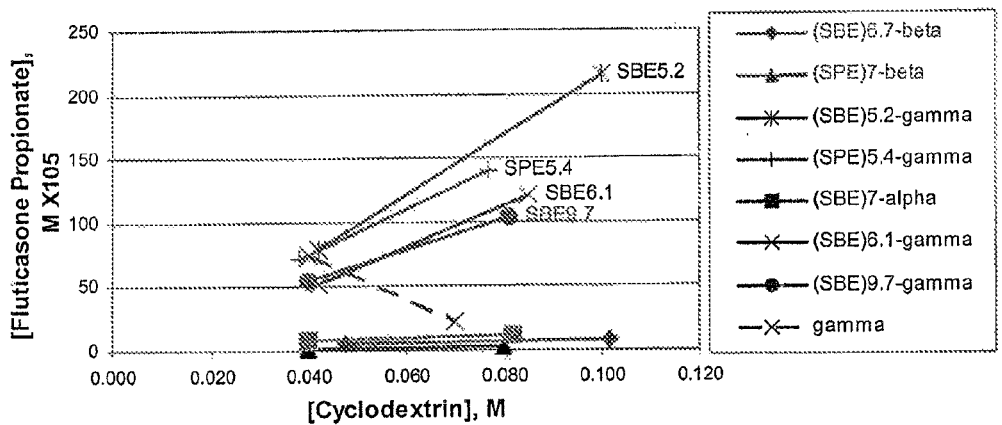
Figure 14:
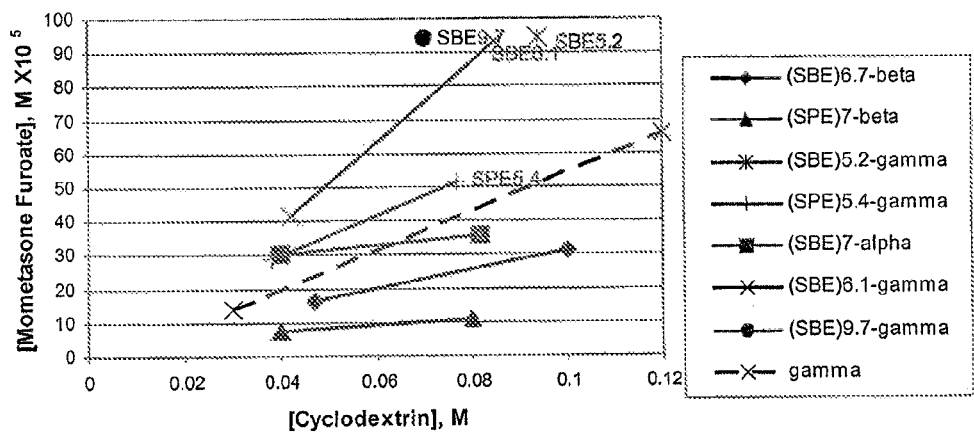

Since SAE-CD is a poly-anionic cyclodextrin, it can be provided in different salt forms. Suitable counterions include cationic organic atoms or molecules and cationic inorganic atoms or molecules. The SAE-CD can include a single type of counterion or a mixture of different counterions. The properties of the SAE-CD can be modified by changing the identity of the counterion present. For example, a first salt form of SAE-CD can have a greater corticosteroid stabilizing and/or solubilizing power than a different second salt form of SAE-CD. Likewise, an SAE-CD having a first degree of substitution can have a greater corticosteroid stabilizing and/or solubilizing power than a second SAE-CD having a different degree of substitution. The enhanced solubilization of a corticosteroid by one SAE-CD versus another is demonstrated by the data in the following tables which depict the molar solubility for fluticasone propionate with different SAE-CDs at about 0.03 to 0.12M concentrations such that the solubilizing power followed about this rank order over this concentration range of SAE-CD: SBE5.2-γ-CD>SPE5.4-γ-CD>SBE6.1-γ-CD>SBE9.7-γ-CD>>SBE7-α-CD>SBE6.7-β-CD>SPE7-β-CD. For mometasone furoate, the solubilizing power followed about this rank order over this concentration range of SAE-CD: SBE9.7-γ-CD>SBE6.1-γ-CD>SBE5.2-γ-CD>>SPE5.4-γ-CD>SBE7-α-CD>SBE6.7-β-CD>SPE7-β-CD. Differences were also observed for the binding of budesonide and triamcinolone with specific embodiments of SAE-CD. According to the invention, a SAE-γ-CD binds a corticosteroid better than a SAE-β-CD does. Also, a SAE-β-CD binds budesonide better than a SAE-α-CD does. The data is summarized in FIGS. 13-14.

| -CD | [CD] M | [Fluticasone] ×10⁵ M as propionate | [Fluticasone] ×10⁵ M non esterified | [Mometasone] ×10⁵ M as furoate | [Mometasone] ×10⁵ M non esterified | [Budesonide] ×10⁵ M | [Triamcinolone acetonide] ×10⁵ M |
|---|---|---|---|---|---|---|---|
| H₂O | NA | 0.39 | 0.16 | 1.82 | 0.00 | 6.59 | 3.56 |
| β | 0.015M | | | 1.36 | 12.9 | 81.3 | |
| (SBE)₆.₇ β | 0.0465 | 5.41 | 126.4 | 16.4 | 121.7 | 254.8 | 457.0 |
| | 0.0950 | 7.99 | 215.9 | 31.1 | 226.1 | 428.1 | 1023.3 |
| (SBE)₂.₄ β | 0.04 | 1.70 | 12.8 | | | | |
| | 0.08 | 2.46 | | | | | |
| (SPE)₇ β | 0.04 | 1.05 | 93.9 | 7.23 | 122.4 | | |
| | 0.08 | 2.12 | 151.2 | 10.8 | 223.3 | 241.6 | |

Solubility of Selected Steroids Enhanced by Alpha-Cyclodextrins

| -CD | [CD] M | [Fluticasone] ×10⁵ M as propionate | [Fluticasone] ×10⁵ M non esterified | [Mometasone] ×10⁵ M as furoate | [Mometasone] ×10⁵ M non esterified | [Budesonide] ×10⁵ M | [Triamcinolone acetonide] ×10⁵ M |
|---|---|---|---|---|---|---|---|
| H₂O | NA | 0.39 | 0.16 | 1.82 | 0.00 | 6.59 | 3.56 |
| A | 0.04 | | | 0.00 | 8.4 | | |
| | 0.08 | | | 0.27 | 28.5 | | |
| (SBE)₇ α | 0.04 | 8.37 | | 30.1 | 55.0 | 348.1 | |
| | 0.08 | 11.4 | | 35.5 | 116.9 | 597.9 | |

Solubility of Selected Steroids Enhanced by Gamma-Cyclodextrins

| -CD | [CD] M | [Fluticasone] ×10⁵ M as propionate | [Fluticasone] ×10⁵ M non esterified | [Mometasone] ×10⁵ M as furoate | [Mometasone] ×10⁵ M non esterified | [Budesonide] ×10⁵ M | [Triamcinolone acetonide] ×10⁵ M |
|---|---|---|---|---|---|---|---|
| H₂O | NA | 0.39 | 0.16 | 1.82 | 0.00 | 6.59 | 3.56 |
| Γ | 0.035 | 73.5 | | 14.1 | 2.71 | 10.1 | 197.8 |
| | 0.1 | 22.1 | 82.2 | 65.8 | 0.09 | 4.1 | 138.6 |

-continued

| -CD | [CD] M | [Fluticasone] ×10⁵ M | | [Mometasone] ×10⁵ M | | [Budesonide] ×10⁵ M | [Triamcinolone acetonide] ×10⁵ M |
|---|---|---|---|---|---|---|---|
| | | as propionate | non esterified | as furoate | non esterified | | |
| (SBE)$_{5.2}$ | 0.04 | 79.12 | | | | 375.8 | |
| γ | 0.1 | 215.3 | 1440.4 | 93.9 | 889.2 | 861.6 | |
| (SBE)$_{6.1}$ | 0.04 | 51.82 | 575.6 | 41.5 | 841.1 | 306.6 | 1059.5 |
| γ | 0.08 | 120.8 | 949.0 | 92.9 | 1423.1 | 698.8 | 2386.1 |
| (SBE)$_{9.7}$ | 0.04 | 54.5 | | | | | |
| γ | 0.075 | 103.1 | 895.0 | 94.0 | 889.6 | 453.4 | |
| (SPE)$_{5.4}$ | 0.04 | 71.7 | 759.5 | 28.7 | | 400.9 | |
| γ | 0.08 | 140.1 | 1387.8 | 51.3 | 1467.1 | 774.2 | |

Figure 15:
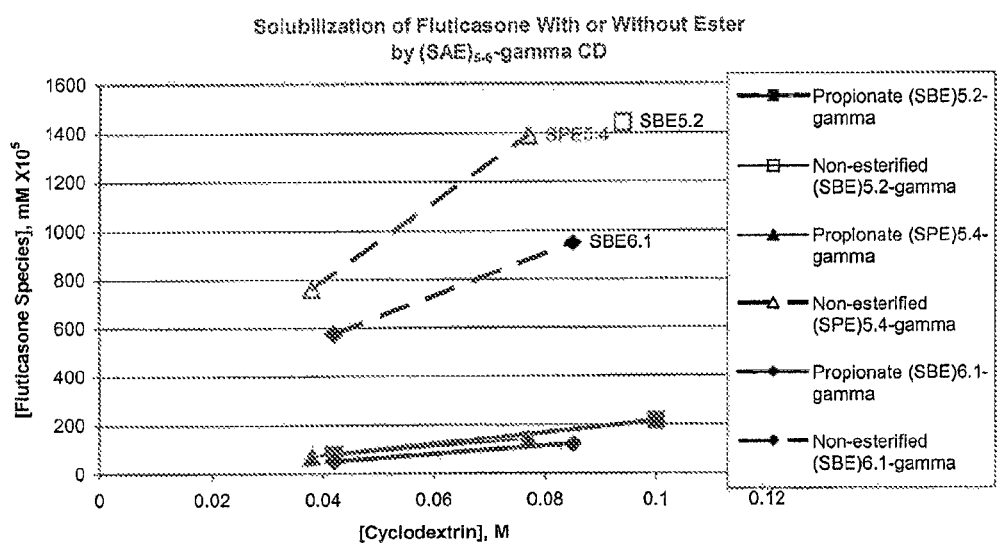
FIG. 15 depicts a phase solubility diagram for esterified and non-esterified fluticasone in the presence of SAE(5-6)-γ-CD.

The inventors have also discovered that SAE-γ-CD is particularly suitable for use in complexing esterified and non-esterified corticosteroids as compared to complexation of the same corticosteroids with SAE-β-CD or SAE-α-CD. The table above also summarizes the phase solubility data depicted in FIG. 15 for fluticasone and fluticasone propionate with various different SAE-γ-CD species having a degree of substitution in the range of 5-10.

The present inventors have discovered that SAE-γ-CD is also much more effective at binding with a particular regioisomer of esterified corticosteroids than is SAE-β-CD or SAE-α-CD. The procedure set forth in Example 18 details the comparative evaluation of the binding of SAE-γ-CD and SAE-β-CD with a series of structurally related corticosteroid derivatives. The table below summarizes the results of a study comparing the binding of SBEx-γ-CD, wherein x represents the average degree of substitution, derivatives and SBE-β-CD derivative with different forms of beclmethasone.

| CD | Beclomethasone dipropionate (μg/mL) | Beclomethasone 17-mono-propionate (μg/mL) | Beclomethasone 21-mono-propionate (μg/mL) | Beclomethasone (unesterified) (μg/mL) |
|---|---|---|---|---|
| SBE$_{3.4}$ γ-CD | 0.04M →336.8 | 0.04M →10621.6 | 0.04M →172.6 | 0.04M →11360.2 |
| SBE$_{5.24}$ γ-CD | 0.04M → 267.0 | 0.04M →9500.8 | 0.04M →139.8 | 0.04M →10949.9 |
| SBE$_{6.1}$ γ-CD | 0.04M →243.8 | 0.04M →11666.9 | 0.04M →153.8 | 0.04M →11007.0 |
| SBE$_{7.5}$ γ-CD | 00.04M → 168.5 | 0.04M →8539.1 | 0.04M →122.4 | 0.04M →9635.2 |
| SBE$_{6.7}$ β-CD | 0.04M →60.4 | 0.04M →6799.6 | 0.04M → 50.6 | 0.04M → 6927.0 |
| γ-CD | 0.04M →105.8 | 0.04M →136.9 | 0.04M →9.4 | 0.04M →114.8 |

Figure 16:
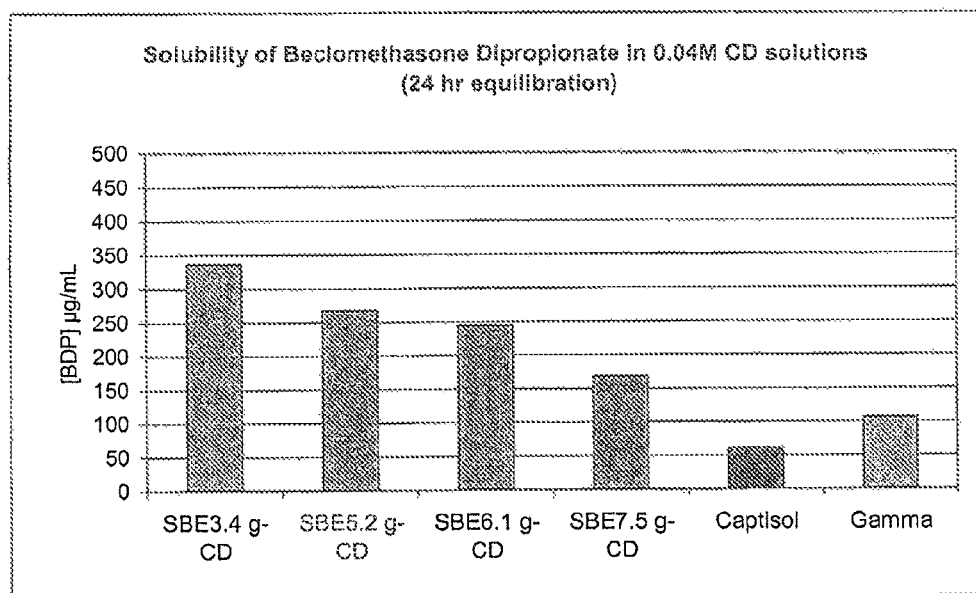
FIG. 16 depicts a bar chart summarizing the aqueous solubility of beclomethasone dipropionate in the presence of various SAE-CD derivatives.

The survey study shows that in the presence of SBE(3.4) γ-CD (0.04M), all of the forms of beclomethasone were at or near their highest solubilities. B17P, the active metabolite of BDP, has the highest solubility of the esterified beclomethasone forms in any of the derivatized CDs. The results indicate that SBE-γ-CD complexes with beclomethasone dipropionate better than Captisol or γ-CD alone. Of the SAE-CD derivatives evaluated, the optimal degree of substitution of the SBE γ-CD that provides the greatest enhancement in solubility of BDP is DS=3.4, and solubility decreases almost linearly as the degree of substitution increases. This is true for both the 24 hr and 5 day equilibration times. So in terms of BDP solubilization with SAE-CD: SBE(3.4)γ-CD>SBE(5.2)γ-CD>SBE(6.1)γ-CD>SBE(7.5)γ-CD>γ-CD>Captisol (SBE7-β-CD). The data is summarized in FIG. 16. Therefore, the present inventors have discovered that SAE-γ-CD cyclodextrin derivatives are unexpectedly better at solubilizing corticosteroids than are SAE-β-CD derivatives. Moreover, the formulations based upon SAE-γ-CD are suitable for use in inhalable formulations contrary to the disclosure of Worth et a (above), which suggests that SAE-CD derivatives are not.

By "complexed" is meant "being part of a clathrate or inclusion complex with", i.e., a complexed therapeutic agent is part of a clathrate or inclusion complex with a cyclodextrin derivative. By "major portion" is meant at least about 50% by weight. Thus, a formulation according to the present invention may contain an active agent of which more than about 50% by weight is complexed with a cyclodextrin. The actual percent of active agent that is complexed will vary according to the complexation equilibrium constant characterizing the complexation of a specific cyclodextrin to a specific active agent. The invention also includes embodiments wherein the active agent is not complexed with the cyclodextrin or wherein a minor portion of the active agent is complexed with the derivatized cyclodextrin. It should be noted that an SAE-CD, or any other anionic derivatized cyclodextrin, can form one or more ionic bonds with a positively charged compound. This ionic association can occur regardless of whether the positively charged compound is complexed with the cyclodextrin either by inclusion in the cavity or formation of a salt bridge.

The binding of a drug to the derivatized cyclodextrin can be improved by including an acid or base along with the drug and cyclodextrin. For example, the binding of a basic drug with the cyclodextrin might be improved by including an acid along with the basic drug and cyclodextrin. Likewise, the binding of an acidic drag with the cyclodextrin might be improved by including a base (alkaline material)

along with the acidic drug and cyclodextrin. The binding of a neutral drug might be improved by including a basic, acidic or other neutral compound along with the neutral drug and cyclodextrin. Suitable acidic compounds include inorganic and organic acids. Examples of inorganic acids are mineral acids, such as hydrochloric and hydrobromic acid. Other suitable acids include sulfuric acid, sulfonic acid, sulfenic acid, and phosphoric acid. Examples of organic acids are aliphatic carboxylic acids, such as acetic acid, ascorbic acid, carbonic acid, citric acid, butyric acid, fumaric acid, glutaric acid, glycolic acid, α-ketoglutaric acid, lactic acid, malic acid, mevalonic acid, maleic acid, malonic acid, oxalic acid, pimelic acid, propionic acid, succinic acid, tartaric acid, or tartronic acid. Aliphatic carboxylic acids bearing one or more oxygenated substituents in the aliphatic chain are also useful. A combination of acids can be used.

Suitable basic compounds include inorganic and organic bases. Suitable inorganic bases include ammonia, metal oxide and metal hydroxide. Suitable organic bases include primary amine, secondary amine, tertiary amine, imidazole, triazole, tetrazole, pyrazole, indole, diethanolamine, triethanolamine, diethylamine, methylamine, tromethamine (TRIS), aromatic amine, unsaturated amine, primary thiol, and secondary thiol. A combination of bases can be used.

An anionic derivatized cyclodextrin can complex or otherwise bind with an acid-ionizable agent. As used herein, the term acid-ionizable agent is taken to mean any compound that becomes or is ionized in the presence of an acid. An acid-ionizable agent comprises at least one acid-ionizable functional group that becomes ionized when exposed to acid or when placed in an acidic medium. Exemplary acid-ionizable functional groups include a primary amine, secondary amine, tertiary amine, quaternary amine, aromatic amine, unsaturated amine, primary thiol, secondary thiol, sulfonium, hydroxyl, enol and others known to those of ordinary skill in the chemical arts.

The degree to which an acid-ionizable agent is bound by non-covalent ionic binding versus inclusion complexation formation can be determined spectrophotometrically using methods such as $^1$HNMR, $^{13}$CNMR, or circular dichroism, for example, and by analysis of the phase solubility data for the acid-ionizable agent and anionic derivatized cyclodextrin. The artisan of ordinary skill in the art will be able to use these conventional methods to approximate the amount of each type of binding that is occurring in solution to determine whether or not binding between the species is occurring predominantly by non-covalent ionic binding or inclusion complex formation. An acid-ionizable agent that binds to derivatized cyclodextrin by both means will generally exhibit a bi-phasic phase solubility curve. Under conditions where non-covalent ionic bonding predominates over inclusion complex formation, the amount of inclusion complex formation, measured by NMR or circular dichroism, will be reduced even though the phase solubility data indicates significant binding between the species under those conditions; moreover, the intrinsic solubility of the acid-ionizable agent, as determined from the phase solubility data, will generally be higher than expected under those conditions.

As used herein, the term non-covalent ionic bond refers to a bond formed between an anionic species and a cationic species. The bond is non-covalent such that the two species together form a salt or ion pair. An anionic derivatized cyclodextrin provides the anionic species of the ion pair and the acid-ionizable agent provides the cationic species of the ion pair. Since an anionic derivatized cyclodextrin is multivalent, an SAE-CD can form an ion pair with one or more acid-ionizable agents.

The parent cyclodextrins have limited water solubility as compared to SAE-CD and HPCD. Underivatized α-CD has a water solubility of about 14.5% w/v at saturation. Underivatized β-CD has a water solubility of about 1.85% w/v at saturation. Underivatized γ-CD has a water solubility of about 23.2% w/v at saturation. Dimethyl-beta-cyclodextrin (DMCD) forms a 43% w/w aqueous solution at saturation. The SAE-CD can be combined with one or more other cyclodextrins or cyclodextrin derivatives in the inhalable solution to solubilize the corticosteroid.

Other water soluble cyclodextrin derivatives that can be used according to the invention include the hydroxyethyl, hydroxypropyl (including 2- and 3-hydroxypropyl) and dihydroxypropyl ethers, their corresponding mixed ethers and further mixed ethers with methyl or ethyl groups, such as methylhydroxyethyl, ethyl-hydroxyethyl and ethyl-hydroxypropyl ethers of alpha-, beta- and gamma-cyclodextrin; and the maltosyl, glucosyl and maltotriosyl derivatives of alpha, beta- and gamma-cyclodextrin, which may contain one or more sugar residues, e.g. glucosyl or diglucosyl, maltosyl or dimaltosyl, as well as various mixtures thereof, e.g. a mixture of maltosyl and dimaltosyl derivatives. Specific cyclodextrin derivatives for use herein include hydroxypropyl-beta-cyclodextrin, hydroxyethyl-beta-cyclodextrin, hydroxypropyl-gamma-cyclodextrin, hydroxyethyl-gamma-cyclodextrin, dihydroxypropyl-beta-cyclodextrin, glucosyl-alpha-cyclodextrin, glucosyl-beta-cyclodextrin, diglucosyl-beta-cyclodextrin, maltosyl-alpha-cyclodextrin, maltosyl-beta-cyclodextrin, maltosyl-gamma-cyclodextrin, maltotriosyl-beta-cyclodextrin, maltotriosyl-gamma-cyclodextrin and dimaltosyl-beta-cyclodextrin, and mixtures thereof such as maltosyl-beta-cyclodextrin/dimaltosyl-beta-cyclodextrin, as well as methyl-beta-cyclodextrin. Procedures for preparing such cyclodextrin derivatives are well-known, for example, from Bodor U.S. Pat. No. 5,024,998 dated Jun. 18, 1991, and references cited therein. Other cyclodextrins suitable for use in the present invention include the carboxyalkyl thioether derivatives such as ORG 26054 and ORG 25969 made by ORGANON (AKZO-NOBEL), hydroxybutenyl ether derivatives made by EASTMAN, sulfoalkyl-hydroxyalkyl ether derivatives, sulfoalkyl-alkyl ether derivatives, and other derivatives as described in US Fragrant Patent Application Publications No. 2002/0128468, No. 2004/0106575, No. 2004/0109888, and No. 2004/0063663, or U.S. Pat. No. 6,610,671, No. 6,479,467, No. 6,660,804, or No. 6,509,323.

The HP-β-CD can be obtained from Research Diagnostics Inc. (Flanders, N.J.). HP-β-CD is available with different degrees of substitution. Exemplary products include ENCAPSIN™ (degree of substitution~4; HP4-β-CD) and MOLECUSOL™ (degree of substitution~8; HP8-β-CD); however, embodiments including other degrees of substitution are also available. Since HPCD is non-ionic, it is not available in salt form.

Dimethyl cyclodextrin is available from FLUKA Chemie (Buchs, CH) or Wacker (Iowa). Other derivatized cyclodextrins suitable in the invention include water soluble derivatized cyclodextrins; Exemplary water-soluble derivatized cyclodextrins include carboxylated derivatives; sulfated derivatives; alkylated derivatives; hydroxyalkylated derivatives; methylated derivatives; and carboxy-β-cyclodextrins, e.g. succinyl-β-cyclodextrin (SCD), and $6^A$-amino-$6^A$-deoxy-N-(3-carboxypropyl)-β-cyclodextrin. All of these materials can be made according to methods known in the prior art. Suitable derivatized cyclodextrins are disclosed in *Modified Cyclodextrins: Scaffolds and Templates for Supramolecular Chemistry* (Eds. Christopher J. Easton, Stephen F. Lincoln, Imperial College Press, London, UK, 1999) and *New Trends in Cyclodextrins and Derivatives* (Ed. Dominique Duchene, Editions de Santé, Paris, France, 1991).

Sulfobutyl ether β-cyclodextrin (CAPTISOL, CyDex Inc., degree of substitution=6.6), 2-hydroxypropyl β-cyclodextrin (HP-β-CD, CERESTAR, degree of substitution=5.5), succinylated-β-cyclodextrin (S-CD, Cyclolab), and 2,6,di-o-methyl-β-cyclodextrin (DM-CD, Fluka) % w/w solutions were prepared at their native pH or buffered as needed. Sulfoalkyl ether γ-CD and sulfoalkyl ether α-CD derivatives were obtained from CyDex, Inc. (Lenexa, Kans.) and The University of Kansas (Lawrence, Kans.).

The amount of derivatized cyclodextrin required to provide the desired effect will vary according to the materials comprising the formulation.

Figure 3:
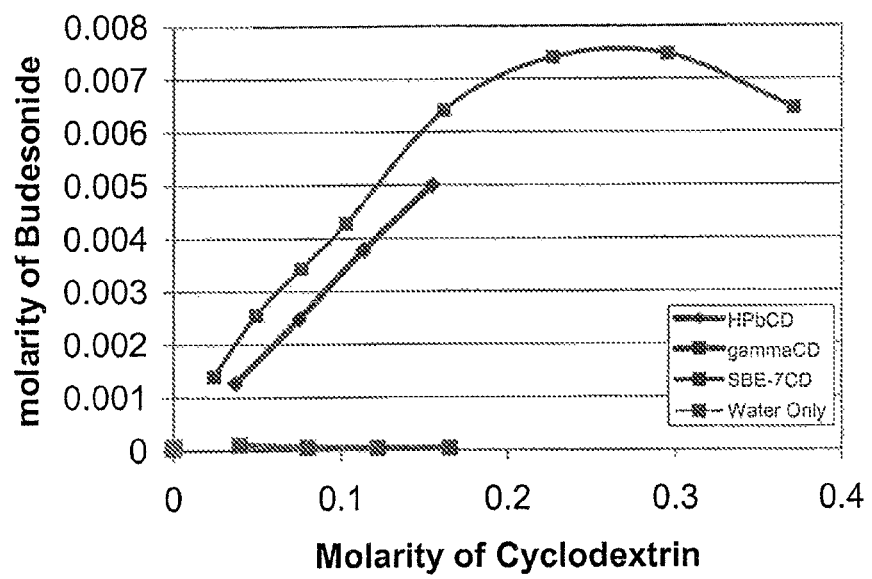
Figure 4:
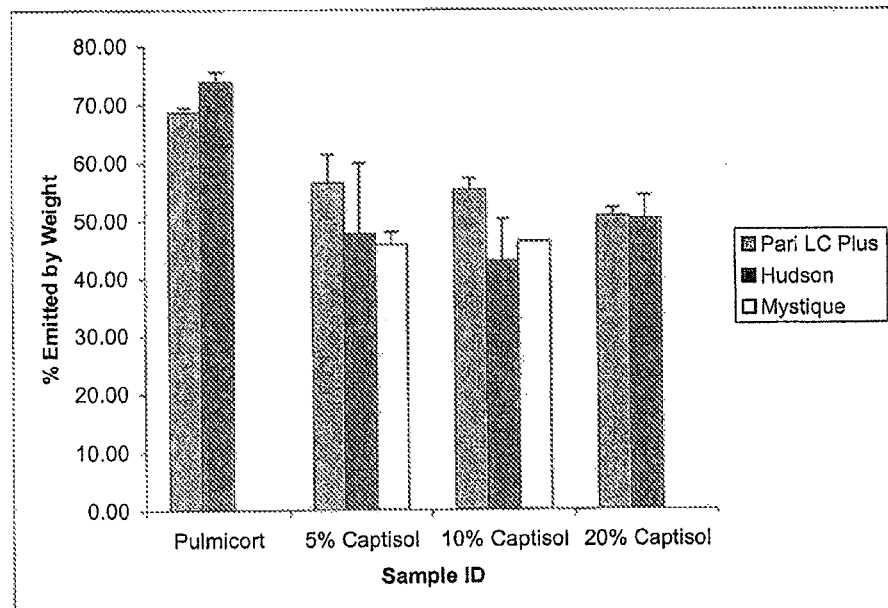

Different cyclodextrins are able to solubilize a corticosteroid to different extents. FIG. 3 depicts a molar phase solubility curve for budesonide with HP-β-CD, SBE7-β-CD, and γ-CD as compared to water. The inventors have found that SAE-CD is superior to other cyclodextrins and cyclodextrin derivatives at solubilizing budesonide. On a molar basis, SBE-β-CD is a better solubilizer of budesonide than HP-β-CD. In addition, the solubilizing power among the SAE-CD derivatives followed about this rank order for budesonide over a SAE-CD concentration range of 0.04 to 0.1M: SBE5.2-γ-CD ~SPE5.4-γ-CD>SBE6.1-γ-CD>SBE7-α-CD>SBE9.7-γ-CD SBE6.7-β-CD>SPE7-β-CD. For example, a 0.1M concentration of SBE7-β-CD was able to solubilize a greater amount of budesonide than either γ-CD or HP-β-CD. Moreover, SAE-CD-containing nebulizable formulations provide a greater output rate for corticosteroid by nebulization as compared to γ-CD or HP-β-CD administered under otherwise similar conditions.

It was unexpectedly discovered that the nebulization of Captisol solutions provides several advantages with respect to other cyclodextrins. The droplets leaving the nebulizer are of a more advantageous size and the Captisol solutions are nebulized faster than similar solutions of other Cyclodextrins. The table below shows that the average particle size (Dv50) of Captisol solutions is smaller than that of HP-β-CD or γ-CD. More importantly, as seen in the table below, the Dv90 shows that the other cyclodextrins had significant number of very large droplets. The data (Malvern particle size) was obtained for each formulation as emitted from a PARI LC PLUS nebulizer equipped with a PARI PRONEB ULTRA air compressor. The smaller droplet size is favored for an inhalable composition as it permits deeper lung delivery of active agents such as a corticosteroid.

| Formulation | Dv10 (μm) | Dv 50 (μm) | Dv 90 (μm) |
|---|---|---|---|
| 5% Captisol | 1.9 ± 0.04 | 3.84 ± 0.08 | 10.52 ± 0.2 |
| 10% Captisol | 1.82 ± 0.05 | 3.61 ± 0.25 | 11.18 ± 1.92 |
| 20% Captisol | 1.78 ± 0.04 | 3.12 ± 0.11 | 10.02 ± 0.23 |
| 5% Hydroxypropyl β-Cyclodextrin | 1.89 ± 0.04 | 3.99 ± 0.13 | 14.89 ± 2.45 |
| 10% Hydroxypropyl β-Cyclodextrin | 1.95 ± 0.03 | 4.62 ± 0.34 | 120.1 ± 172.67 |
| 20% Hydroxypropyl β-Cyclodextrin | 1.91 ± 0.02 | 4.26 ± 0.16 | 13.77 ± 1.00 |
| 5% γ-Cyclodextrin | 1.94 ± 0.05 | 3.99 ± 0.36 | 205.62 ± 222.10 |
| 10% γ-Cyclodextrin | 2.03 ± 0.05 | 4.84 ± 0.49 | 451.55 ± 25.92 |
| 20% γ-Cyclodextrin | 1.96 ± 0.04 | 4.97 ± 0.12 | 286.46 ± 235.13 |

This advantage is further shown in the output rate of these solutions. The table below shows that Captisol is emitted from the nebulizer faster and also to a greater extent than the other cyclodextrins, thus the output rate of the nebulizer is greater when Captisol is nebulized.

| Formulation | Percent Emitted | Sputter Time (min) | Output Rate mg/min |
|---|---|---|---|
| 5% Captisol | 56.42 | 3.81 | 296 |
| 10% Captisol | 55.13 | 3.84 | 287 |
| 20% Captisol | 50.56 | 4.06 | 249 |
| 5% Hydroxypropyl β-Cyclodextrin | 43.32 | 4.14 | 209 |
| 10% Hydroxypropyl β-Cyclodextrin | 46.22 | 4.27 | 216 |
| 20% Hydroxypropyl β-Cyclodextrin | 46.90 | 4.01 | 234 |
| 5% γ-Cyclodextrin | 52.74 | 5.41 | 195 |
| 10% γ-Cyclodextrin | 53.75 | 4.98 | 216 |
| 20% γ-Cyclodextrin | 51.91 | 4.81 | 216 |

Nebulization is stopped when the sound changes (time to sputter) or visible particles are no longer produced. Sputter occurs at substantial completion of delivery of solution in the reservoir of the nebulizer.

The advantage of Captisol was further demonstrated by preparing solutions containing budesonide dissolved in various cyclodextrins and comparing their performance in nebulization to the performance of commercial PULMICORT® RESPULES®, a commercially available suspension-based unit dose formulation. The suspension obtained from several unit dose ampoules of PULMICORT™ was pooled to form a multi-use suspension based unit dose formulation, and SAE-CD (specifically, CAPTISOL), HP-β- or γ-cyclodextrin powder was added to achieve a 0.25 mg/ml budesonide solution concentration. These budesonide-containing solutions contained 5% w/v Captisol (P5C), 1% w/v gamma-CD (P1γCD) and 5% w/v hydroxypropyl-beta-cyclodextrin (P5HPβCD). Each was prepared at least 30 minutes prior to all testing, All three formulations were clear, colorless solutions. (Note: a 250 mg/mL solution of budesonide cannot be achieved in a 5% w/v solution of γ-cyclodextrin as it exhibits "B" type solubility behavior) A 2 ml aliquot of the suspension or solution was placed in the same Pari LC Plus nebulizer setup and the amount of budesonide in the emitted droplets was determined by collecting them onto a filter and measuring the budesonide using HPLC. As shown in the table below, the total output rate (μg budesonide collected/time to sputter) for each suspension or solution.

| Sample ID | Total Output Rate (μg/min) | SD (μg/min) |
|---|---|---|
| Pulmicort | 33.85 | 3.85 |
| Pulmicort + 5% Captisol | 44.04 | 1.42 |
| Pulmicort + 5% HP-β-CD | 21.37 | 2.44 |
| Pulmicort + 1% γ-CD | 40.36 | 5.73 |

The output rate is highest for the Captisol solution indicating that an equivalent amount of drug can be delivered in a shorter period of time. Under the conditions used, β-CD is unable to solubilize an equivalent amount of corticosteroid due to the limited solubility of β-CD in water.

The present invention can be used with other suspension-based aqueous formulations, which formulations may be adapted for nasal delivery or pulmonary delivery. Exemplary suspension-based aqueous formulations include the UDB formulation (Sheffield Pharmaceuticals, Inc.), VANCENASE™ AQ (beclomethasone dipropionate aqueous suspension; Schering Corporation, Kenilworth, N.J.), ATOMASE™ (beclomethasone dipropionate aqueous suspension; Douglas Pharmaceuticals Ltd., Aukland, Australia), BECONASE™ (beclomethasone dipropionate aqueous suspension; Glaxo Wellcome, NASACORT AQ™ (triamcinolone acetonide nasal spray, Aventis Pharmaceuticals), TRI-NASAL™ (triamcinolone acetonide aqueous suspension; Muro Pharmaceuticals Inc.) and AEROBID-M™, (flunisolide inhalation aerosol, Forest Pharmaceuticals), NASALIDE™ and NASAREL™ (flunisolide nasal spray, Wax Corporation), FLONASE™ (fluticasone propionate, GlaxoSmithKline), and NASONEX™ (mometasone furoate, Schering-Plough Corporation).

The suspension formulation can comprise corticosteroid present in particulate, microparticulate, nanoparticulate or nanocrystallirie form. Accordingly, an SAE CD can be used to improve the administration of a corticosteroid suspension-based unit dose formulation. Moreover, the SAE-CD outperforms other cyclodextrin derivatives.

According to one embodiment, SAE-CD (in solid or liquid form) and a suspension-based unit dose formulation comprising corticosteroid are mixed. The SAE-CD is present in an amount sufficient to increase the amount of solubilized corticosteroid, i.e. decrease the amount of unsolubilized corticosteroid, therein. Prior to administration, the liquid may be optionally aseptically filtered or terminally sterilized. The liquid is then administered to a subject by inhalation using a nebulizer. As a result, the amount of drug that the subject receives is higher than the subject would have received had the unaltered suspension formulation been administered.

According to another embodiment, SAE-CD (in liquid form, as ready-to-use liquid or as a concentrate) and a solid unit dose formulation comprising corticosteroid are mixed to form a liquid formulation. The SAE-CD is present in an amount sufficient to solubilize a substantial portion of the corticosteroid. The liquid is then administered via inhalation using a nebulizer.

According to another embodiment, SAE-CD (in solid form) and a solid unit dose formulation comprising corticosteroid are mixed to form a solid mixture to which is added an aqueous liquid carrier in an amount sufficient to form a nebulizable formulation. Mixing and/or heating are optionally employed upon addition of the liquid carrier to form the formulation. The SAE-CD is present in an amount sufficient to solubilize a substantial portion of the corticosteroid. The formulation is then administered via inhalation using a nebulizer.

The size of the reservoir varies from one type of nebulizer to another. The volume of the liquid formulation may be adjusted as needed to provide the required volume for loading into the reservoir of a particular type or brand of nebulizer. The volume can be adjusted by adding additional liquid carrier or additional solution containing SAE-CD. In general, the reservoir volume of a nebulizer is about 10 μl to 100 ml. Low volume nebulizers, such as ultrasonic and vibrating mesh/vibrating plate/vibrating cone/vibrating membrane nebulizers, pre-filled reservoir strips inclusive of delivery nozzle typically have a reservoir volume of 10 μl to 6 ml or 10 μl to 5 ml. The low volume nebulizers provide the advantage of shorter administration times as compared to large volume nebulizers.

Example 28 details a procedure for preparation of a solution of the invention to be used with a low volume (low reservoir volume and/or low reservoir residual volume) nebulizer, such as an AERx nebulizer. The solutions of the invention can be nebulized with any nebulizer; however, with an AERx delivery system that coordinates both the inhalation and delivery processes to optimize deep lung penetration, an initial sample volume of about 10 to 100, or 50 μl can be used to load AERx Strip unit dose container. Administration of this solution with the system makes it feasible for a therapeutic dose to be administered to a subject in a single puff (a single full inhalation by a subject, i.e. 3-5 seconds) via nebulization. Based on general performance expectations of such devices where the emitted dose is 60-65% and the subsequent lung doses are 65-85%, about 10 μg to 60 μg or 10 μg to 110 μg of budesonide may be expected to be delivered to the lung in a single dosing event using budesonide solutions prepared with SAECD.

Example 32 details a procedure for the comparison of nebulization parameters in four different nebulizers using a formulation of the invention and PULMICORT RESPULES (suspension-based formulation). In each case, the formulation of the invention out performs the suspension-based formulation. The solution of the invention provide a 1.25, 1.4, 2.1, 3.3, 3.67, 1.25 to 3.7, or 1.25 to 4 fold increase in the amount of budesonide delivered. Under the conditions tested, the AIRSEP MYSTIQUE was most efficient at emitting/nebulizing the SAE-CD/budesonide formulation.

Unless otherwise specified, the term "dose", which is understood to include an effective dose, is taken to mean a nominal dose, emitted dose, nominal available dose, dose to subject, dose to lung or other such term of art. The term "nominal dose" refers to an amount of corticosteroid placed in the reservoir of a nebulizer, wherein the volume of liquid in the reservoir is determined according the size of the reservoir. The term "nominal available dose" refers to the amount of corticosteroid that is determined could be or should have been available to a subject when administered a formulation of the invention by nebulization but formulation is/was not administered in its entirety. The term "emitted dose" refers to the amount of corticosteroid emitted from a nebulizer. The term "dose to subject" refers to the amount of corticosteroid delivered to and retained by a subject following administration of a formulation of the invention by nebulization. The term "dose to lung" refers to the amount of corticosteroid delivered to and retained by the lungs of a subject following administration of a formulation of the invention by nebulization.

In general, a single-use suspension-based unit dose formulation of corticosteroid contains about 0.125, 0.25, 0.5, 1, 2, or about 0.125 to about 2 mg of corticosteroid suspended in about 50 μl to 10 ml of liquid carrier. Alternatively, the corticosteroid is present at a concentration of about 20 mcg to about 30 mg of corticosteroid per ml of suspension. As a result, about 10 to 500 mg of SAE-CD, or 10 to 250 mg of SAE-CD, or 10 to 300 mg of SAE-CD, be it in solid form or dissolved in a liquid carrier, is added to each ml the suspension in order to dissolve a substantial portion of the corticosteroid and form a nebulizable unit dose liquid formulation that is then administered to a subject.

The formulation, method or system can employ a dose of about 1 μg to 20 mg, 1 μg to 10 mg, 0.01 mg to 10 mg, 0.025 mg to 10 mg, 0.05 mg to 5 mg, 0.1 mg to 5 mg, 0.125 mg to 5 mg, 0.25 mg to 5 mg, 0.5 mg to 5 mg, 0.05 mg to 2 mg, 0.1 mg to 2 mg, 0.125 mg to 2 mg, 0.25 mg to 2 mg, 0.5 mg to 2 mg of corticosteroid. These dose amounts are suitable for the corticosteroids of the invention, in particular corticosteroids that are as lipophilic as or more lipophilic than flunisolide, which corticosteroids include beclomethasone, beclomethasone dipropionate, beclomethasone monopropionate, budesonide, ciclesonide, desisobutyryl-ciclesonide, flunisolide, fluticasone, fluticasone propionate, mometasone, mometasone furoate, triamcinolone acetonide.

The formulation of the invention comprises a dose of corticosteroid in an approximate solution volume of 10 µl to 100 ml, 50 µl to 50 ml, 50 µl to 10 ml, 0.1 to 10 ml, 0.1 ml to less than 10 ml, 0.1 ml to 7.5 ml, 0.1 ml to 5 ml, 0.1 ml to 3 ml, 0.1 ml to 2 ml, 0.1 ml to 1 ml, 0.05 ml to 7.5 ml, 0.05 ml to 5 ml, 0.05 ml to 3 ml, 0.05 ml to 2 ml, or 0.05 ml to 1 ml.

Due to the wide range of nebulizer reservoir volumes available and of varying dose requirements among the corticosteroids, a formulation of the invention can comprise 1 µg to 20 mg of corticosteroid in 0.01 ml to 100 ml of solution volume.

In general, a multi-use suspension-based unit dose formulation of corticosteroid contains approximately 0.125 to 2 mg of corticosteroid suspended in 1 to 100 ml of liquid carrier. A multi-use formulation actually contains two or more unit doses of corticosteroid. Single unit dose aliquots are taken from a multi-use unit dose formulation, and the single unit dose are typically administered one-at-a-time to a subject. As a result, about 10 to 500 mg of SAE-CD, be it in solid form or dissolved in a liquid carrier, is added to each ml the suspension in order to dissolve a substantial portion of the corticosteroid and form a multi-use unit dose liquid formulation that is then administered to a subject in single unit dose aliquots.

One aspect of the invention is that a suspension-based unit dose formulation is converted to a liquid unit dose formulation prior to pulmonary administration via inhalation (of a nebulized mist) to a subject. The conversion can take place in the same container in which the suspension is provided, in a different container, or in the reservoir of a nebulizer. In order to form a liquid formulation, a substantial portion of the corticosteroid must be dissolved. As used in reference to the amount of dissolved corticosteroid, a “substantial portion” is at least 20% wt., at least 30% wt., at least 40% wt., or at least 20% wt and less than 50% wt. of the corticosteroid. As used in reference to the amount of dissolved corticosteroid, a “major portion” is at least 50% wt. of the corticosteroid.

It is well known that pharmacists working in compounding pharmacies can and do prepare a suspension-based unit dose formulation comprising corticosteroid. Such pharmacists will now be able to prepare a single use or multi-use liquid unit dose formulation by employing a method described herein. Alternatively, a subject (patient) undergoing corticosteroid treatment may convert the suspension-based formulation to a liquid formulation of the invention by employing a method described herein. Instead of preparing the liquid formulation from the suspension at the pharmacy, a kit containing the suspension formulation and SAE-CD can be prepared.

The concentration of SAE-CD in solution can be expressed on a weight to weight or weight to volume basis; however, these two units are interconvertible. When a known weight of cyclodextrin is dissolved in a known weight of water, the % w/w cyclodextrin concentration is determined by dividing the cyclodextrin weight in grams by the total weight (cyclodextrin+water weight) in like units and multiplying by 100. When a known weight of cyclodextrin is dissolved to a known total volume, the % w/v cyclodextrin concentration is determined by dividing the cyclodextrin weight in grams by the total volume in milliliters and multiplying by 100. The correlation between the two cyclodextrin concentration percentages was experimentally determined by preparing various % w/w cyclodextrin solutions and measuring the density of each with a pycnometer at 25° C. The density (g/mL) of each % w/w CAPTISOL solution is presented in the table below.

| Captisol % w/w | Density (g/mL) | Viscosity (Cp, 25 C.) |
|---|---|---|
| 59.4 | 1.320 | 527.0 |
| 49.4 | 1.259 | 51.9 |
| 39.7 | 1.202 | 17.0 |
| 29.8 | 1.149 | 5.91 |
| 19.7 | 1.095 | 2.78 |
| 8.5 | 1.041 | 1.75 |
| 0.0 | 1.002 | 1 | slope = 0.0053
y-intercept = 0.995
correlation = 0.9989

The resulting linear relationship readily enables the conversion of CAPTISOL concentrations expressed in % w/w to that of % w/v by the following equation:

$$\% \ w/v = ((\% \ w/w * \text{slope}) + y\text{-intercept}) * \% \ w/w$$

where the slope and intercept values are determined from a linear regression of the density data in the table. For example, by using the above equation, a 40% w/w CAPTISOL solution would be equivalent to a ~48.3% w/v CAPTISOL solution.

The performance of an inhalable solution of the invention in a nebulizer may depend upon the viscosity of the solution in its reservoir, the nebulization solution. The viscosity of an aqueous solution of SBE7-β-CD changes with respect to concentration approximately as indicated in the table above. Viscosity of the inhalable composition can have an impact on percentage of nebulization composition emitted from a nebulizer, output rate of nebulized corticosteroid and droplet size distribution.

The amount of residual nebulization inhalable composition left in the reservoir of the nebulizer may be greater for solutions containing SAE-CD than for a budesonide-containing suspension. For example, FIG. 4 depicts a chart of the estimated percentage of nebulization composition emitted from three different nebulizers (PARI LC PLUS, HUDSON UPDRAFT II NEB-U-MIST, and MYSTIQUE) for each of four different nebulization compositions (PULMICORT RESPULES suspension, 5% w/w SBE7-β-CD solution, 10% w/w SBE7-β-CD solution and 20% w/w SBE7-β-CD solution). The PULMICORT RESPULES suspension was used as the control. The PARI LC PLUS, MYSTIQUE and HUDSON nebulizers were used for the comparison. The MYSTIQUE nebulizer was unable to nebulize the suspension and concentrated SAE-CD solution (20% w/w) efficiently so they were not evaluated with that nebulizer. The results suggest that, under the conditions tested, nebulization of PULMICORT RESPULES suspension results in a greater percentage of nebulized composition, meaning that, with the suspension, less nebulization composition is left in the reservoir of the nebulizer upon completion of nebulization as compared to with the solution. In some cases, nebulization of the suspension resulted in the greatest percentage by weight of total composition emitted by a nebulizer. In other words, under similar nebulization conditions, the PARI LC PLUS and HUDSON nebulizers more efficiently reduced the volume of nebulization suspension than of nebulization solution; however, this did not correspond with the total amount of drug emitted by the nebulizer.

Output rate of an SAE-CD nebulization solution versus that of a suspension, each containing budesonide, was compared. A modified version of the method of Example 10 was followed to determine output rate. The tables below summarize the data observed.

| Sample ID | 2 minutes Bud recvr'd (ug) | Total Bud Recovered (ug) | Total Neb Time (min:sec) | Total Neb Time (min) | Out Put Rate 2 minutes (ug/min) | Total Out Put Rate (ug/min) |
|---|---|---|---|---|---|---|
| 1-PUL-1 | 84.021 | 164.199 | 5:34 | 5.57 | 42.01 | 29.48 |
| 1-PUL-2 | 90.395 | 175.63 | 4:58 | 4.97 | 45.20 | 35.34 |
| 1-PUL-3 | 82.046 | 174.546 | 4:45 | 4.75 | 41.02 | 36.75 |
|  | Mean | 171.458 |  | Mean | 42.74 | 33.85 |
|  | SD | 6.310 |  | SD | 2.18 | 3.85 |
|  | CV | 3.680 |  | CV | 5.10 | 11.38 |
| 2-P5C-1 | 131.412 | 258.894 | 5:42 | 5.7 | 65.71 | 45.42 |
| 2-P5C-2 | 126.945 | 246.987 | 5:36 | 5.6 | 63.47 | 44.10 |
| 2-P5C-3 | 128.464 | 236.371 | 5:33 | 5.55 | 64.23 | 42.59 |
|  | Mean | 247.417 |  | Mean | 64.47 | 44.04 |
|  | SD | 11.268 |  | SD | 1.14 | 1.42 |
|  | CV | 4.554 |  | CV | 1.76 | 3.22 |

Data obtained using a PARI LC PLUS nebulizer equipped with a PART PRONEB ULTRA air compressor.

| Sample ID | 2 minutes Bud recvr'd (ug) | Total Bud Recovered (ug) | Total Neb Time (min:sec) | Total Neb Time (min) | Out Put Rate 2 minutes (ug/min) | Total Out Put Rate (ug/min) |
|---|---|---|---|---|---|---|
| 10-PUL-1 | 11.200 | 27.926 | 5:20 | 5.33 | 5.60 | 5.24 |
| 10-PUL-2 | 29.015 | 40.11 | 4:15 | 4.25 | 14.51 | 9.44 |
| 10-PUL-3 | 25.363 | 30.516 | 4:17 | 4.28 | 12.68 | 7.13 |
|  | Mean | 32.851 |  | Mean | 10.93 | 7.27 |
|  | SD | 6.419 |  | SD | 4.71 | 2.10 |
|  | CV | 19.539 |  | CV | 43.05 | 28.93 |
| 11-P5C-1 | 41.049 | 98.155 | 5:47 | 5.78 | 20.52 | 16.98 |
| 11-P5C-2 | 44.495 | 131.8 | 6:00 | 6 | 22.25 | 21.97 |
| 11-P5C-3 | 53.374 | 132.31 | 5:55 | 5.92 | 26.69 | 22.35 |
|  | Mean | 120.755 |  | Mean | 23.15 | 20.43 |
|  | SD | 19.574 |  | SD | 3.18 | 2.99 |
|  | CV | 16.210 |  | CV | 13.73 | 14.66 |

Data obtained using a MYSTIQUE ultrasonic nebulizer.

All of the above formulations contain approximately 250 μg/mL, of budesonide. The samples identified as "P5C" contain 50 mg/mL (or about 5%) SBE7-β-CD.

The table below shows the nebulizer output rate for solutions containing various levels of SAE-CD.

| Sample ID | Viscosity (Cp) | Nebulizer Volume (ml) | % Emitted (By Weight Difference) | Nebulization Time (Minutes: Seconds) | Output Rate |
|---|---|---|---|---|---|
| 21.5% w/w SBE7-β-CD | 3.06 | 3 | 47.47 | 10:51 | 4.52 |
| 10.75% w/w SBE7-β-CD | 1.84 | 3 | 51.36 | 8:53 | 6.02 |
| 5.15% w/w SBE7-β-CD | 1.23 | 3 | 55.47 | 9:59 | 5.78 |
| H₂O |  | 3 | 50.36 | 9:21 | 5.47 |

Surprisingly, nebulization of the SAE-CD-containing solution provided a higher budesonide output rate than nebulization of the PULMICORT RESPULES suspension even though the nebulizer emitted a greater total amount of the suspension. Higher SAE-CD concentrations, above 25% w/v led to slightly longer nebulization times and lower output rates once the viscosity exceeded an approximate upper limit.

Without being held bound to a particular mechanism, it is believed that the nebulizer preferentially nebulizes the water (supernatant) of the suspension rather than the particles of the suspension thereby causing an increase in the molar concentration of budesonide in the suspension in the reservoir. Since the corticosteroid is dissolved in the solution of the invention, this type of separation does not occur to a significant degree. As a result, the rate of increasing concentration of corticosteroid in the reservoir is lower for a solution than it is with a suspension. Further support for this phenomenon is detailed in the following table.

|  | Initial Conc | Final Conc | RIC over 2 min. mcg/mL per min | RIC over TTS, mcg/mL per min |
|---|---|---|---|---|
| Pulmicort Respules | 250 | 572 | 31.26 | 64.37 |
| CEB | 250 | 398 | 14.96 | 26.69 |

The data above was obtained by comparing the nebulization of a solution of the invention (CEB, SAE-CD, 5% wt./v, 2 ml; budesonide, 250 μg/ml) and PULMICORT RESPULES suspension 2 ml; budesonide, 250 μg/ml) using a PARI LC+ equipped with a PARI PRONEB ULTRA air compressor. The concentration of budesonide in the reservoir was measured at two minutes and at time to sputter (TTS). The rate of increasing concentration (RIC) of the corticosteroid in the solution in the reservoir was then calculated for each formulation over each interval of time. The RIC of the solution of the invention provided an approximately 48% decrease in the RIC over two minutes and an approximately 42% decrease in the RIC over the TTS. In some embodiments, the percentage decrease in the RIC ranges from 10% to 60%, 15% to 60%, 20% to 60%, 30% to 60%, or 40% to 60%. In some embodiments, the system may provide a RIC of 0 to 40, 1 to 40, 5 to 30, or 10 to 30 mcg of corticosteroid/mL of solution volume per min of operation/nebulization.

Accordingly, the invention provides a system for administration of a corticosteroid by nebulization comprising: a nebulizer comprising a reservoir; and an inhalable aqueous composition comprising SAE-CD and a dose of corticosteroid, whereby the system provides a reduced RIC for the corticosteroid in the reservoir as compared to the RIC provided by a suspension comprising approximately the same amount of corticosteroid and volume of aqueous composition operated under approximately the same conditions.

Based on data above, 21.5±5% w/w SBE7-β-CD concentration was identified as the approximate upper acceptable level for the nebulizer tested, "acceptable" being defined as the upper concentration of SBE7-β-CD that can be used without building up excessive viscosity, which may adversely affect the nebulization time and output rate. The practical upper limit for concentration of SAE-CD will vary among the nebulizer formats. The upper acceptable concentration of SAE-CD in a liquid formulation for use in a nebulizer may vary according to the DS of the derivative, the alkyl chain length of the sulfoalkyl functional group, and/or the CD ring size of the SAE-CD.

For administration to the respiratory tract, particularly the lungs, a nebulizer is used to produce appropriately sized droplets. Typically, the particle size of the droplet produced by a nebulizer for inhalation is in the range between about 0.5 to about 5 microns. If it is desired that the droplets reach the lower regions of the respiratory tract, i.e., the alveoli and terminal bronchi, the particle size range can be between about 0.5 and about 2.5 microns. If it is desired that the droplets reach the upper respiratory tract, the particle size range can be between 2.5 microns and 5 microns.

Figure 5A:
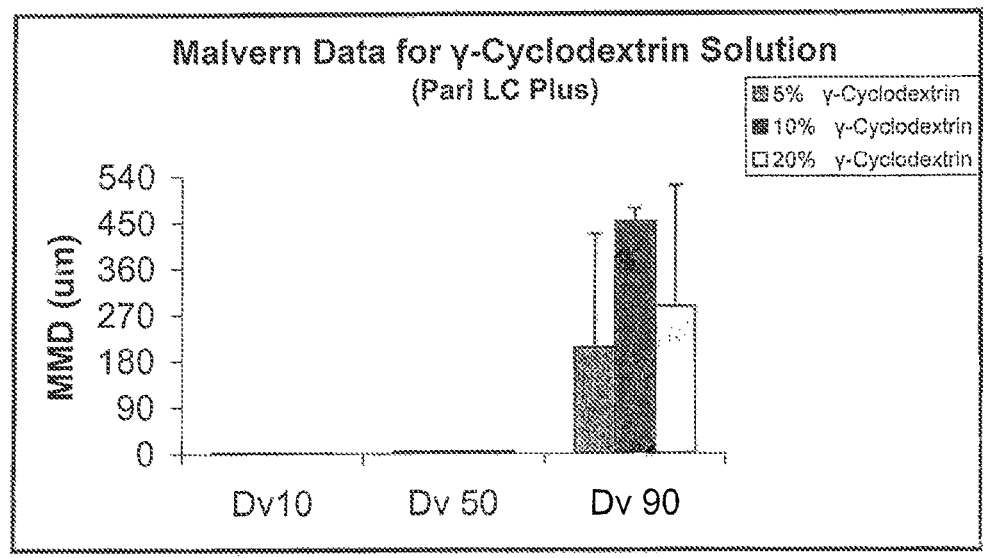
Figure 5B:
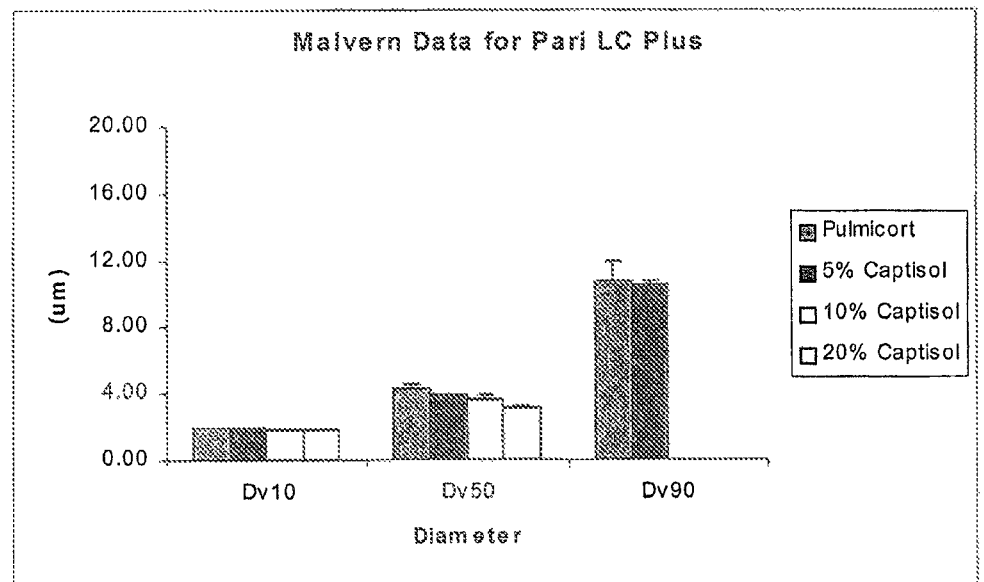

As noted above, viscosity of the nebulization composition, can impact droplet size and droplet size distribution. For example, the present formulations tend to form larger droplets, in terms of Dv50, at the lower concentrations, and thereby lower viscosity, of SAE-CD in the absence of budesonide. FIGS. 5a-5b depict droplet size data for nebulization of inhalable compositions with a PARI LC PLUS nebulizer. For each of the figures, a MALVERN laser light scattering device (Mastersizer S, Malvern Instruments Ltd. Malvern, Worcs, U.K.) was used to measure MMAD. FIG. 5a depicts the results obtained using γ-CD solutions of varying concentrations (5% w/v, 10% w/v and 20% w/v) in the absence of budesonide. The results indicate that γ-CD on its own would not behave acceptably in a nebulizer, since almost all of the mass of the solution is of an unacceptable droplet size range. Even with extensive recycling and droplet size selection by a nebulizer, a γ-CD based nebulization solution containing corticosteroid would require an extremely long dosing period due to the low percentage of mass that is of the appropriate droplet size range, especially since γ-CD is not an effective solubilizer of budesonide at the concentrations tested.

In comparison, FIG. 5b depicts the results obtained using the same nebulizer with PULMICORT RESPULES suspension or a modified PULMICORT RESPULES solution containing SAE-CD of different concentrations (5% w/v, 10% w/v and 20% w/v). With each of these samples, a significant portion of the nebulized mass is of a respirable size range. Moreover, the solutions containing SAE-CD apparently form droplets that are comparable in size to those of the nebulized suspension.

Figure 6:
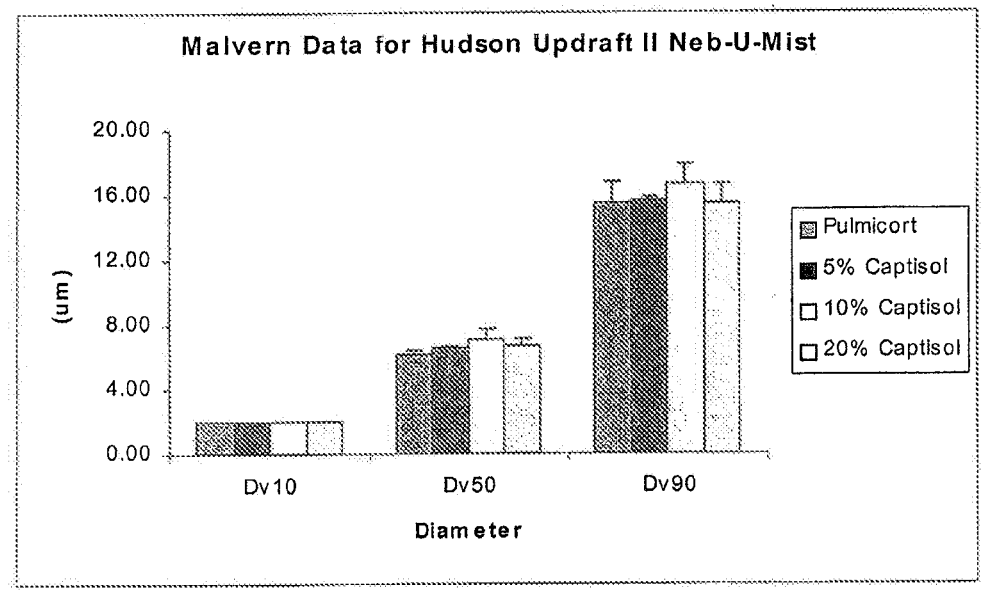

FIG. 6 depicts droplet size data for nebulization of inhalable compositions with a HUDSON UPDRAFT II NEBU-MIST nebulizer charged with PULMICORT RESPULES suspension or a solution containing SAE-CD at different concentrations. (5% w/v, 10% w/v and 20% w/v). As compared to the PARI LC PLUS nebulizer, the NEB-U-MIST forms a slightly larger particle size distribution, a significant portion of the nebulized mass is still in the appropriate size range. Accordingly, the nebulization solution made from the suspension and containing SAE-CD is suitable for use in a variety of different air driven jet nebulizers.

Figure 7:
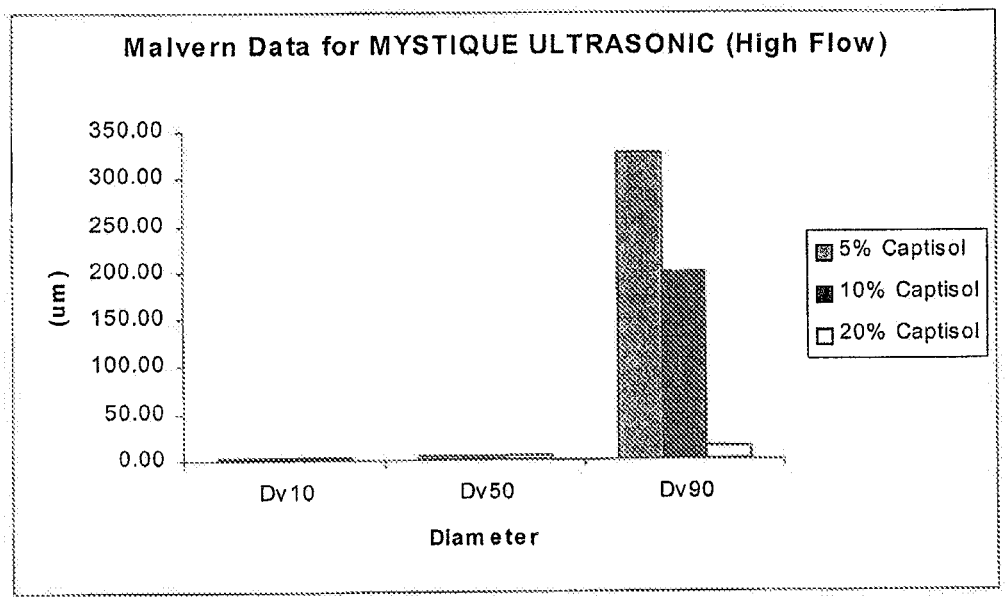

The package insert for PULMICORT RESPULES suspension states that the suspension should not be nebulized with an ultrasonic nebulizer. FIG. 7 depicts droplet size data for nebulization of inhalable compositions with a MYSTIQUE ultrasonic nebulizer. The compositions include three different SAE-CD containing solutions. Unlike the suspension, the SAE-CD containing solution can be nebulized with an ultrasonic nebulizer. Thus, the invention provides a method of improving the pulmonary delivery of corticosteroid in a suspension-based unit dose formulation from an ultrasonic nebulizer, the method comprising the step of including SAE-CD in the formulation in an amount sufficient to decrease the amount of undissolved corticosteroid in the suspension-based unit dose formulation.

The performance of nebulization compositions across a range of nebulizers is typically compared by comparing the Dv50 of the droplet size distribution for the respective compositions. FIG. 8 depicts comparative Dv50 droplet size data for nebulization of an inhalable composition with the three above-mentioned nebulizers. In each case, the SAE-CD containing solutions are suitable for administration by nebulization across a range of concentrations. Moreover, the droplet size distribution can be partially controlled by adjusting the concentration of SAE-CD.

FIG. 9 is a graph depicting the relationship between concentration of SAE-CD versus output rate of SAE-CD in various different nebulizers with different sources of compressed air required for the specific setup: the RAINDROP-Rat, RAINDROP-Dog, PARI LC STAR-UNC, PARI LC STAR-Rat PARI LC PLUS and DEVILBISS PULMO AIDE air jet driven nebulizers. The nebulizers were used in a variety of setups including free standing as well as animal exposure chambers and/or individual exposure masks. In general, the data demonstrate that output of SAE-CD increases with increasing SAE-CD concentration. Depending upon the nebulizer used, the conditions under which the nebulizer is operated and the concentration of SAE-CD in solution, different maximum output rates can be achieved. For example, the maximum output rate in the Raindrop-Dog setup is from a 250 mg/mL CAPTISOL concentration.

Figure 10A:
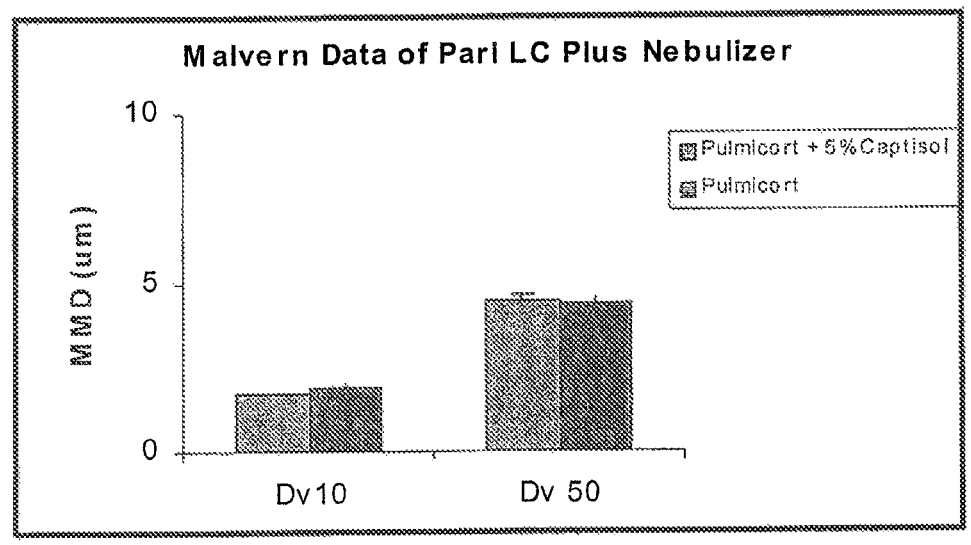
Figure 10B:
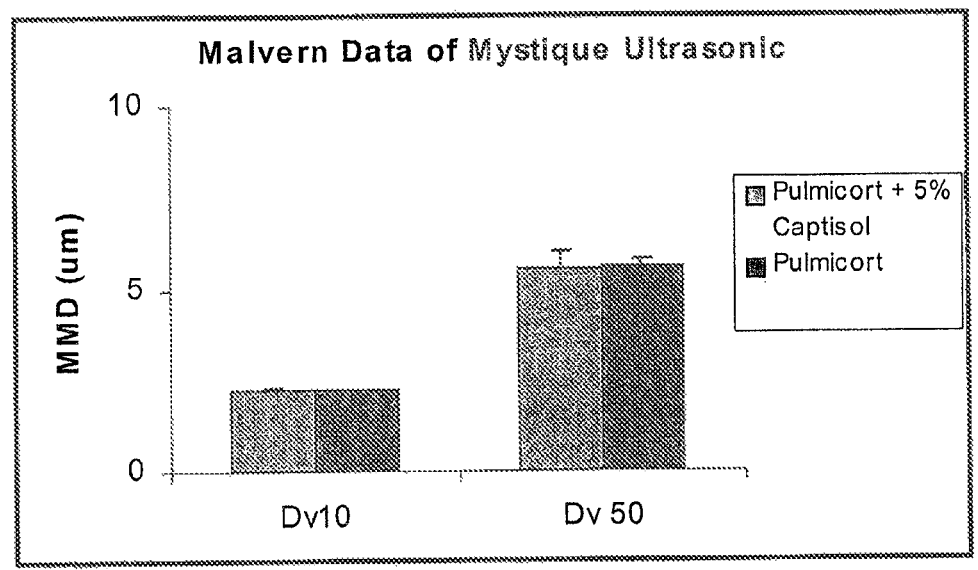

Even though nebulization of PULMICORT RESPULES suspension with an ultrasonic nebulizer is not recommended, it can be achieved. FIGS. 10a-10b depict comparative droplet size data for nebulization solutions with the PARI LC PLUS and MYSTIQUE nebulizers of PULMICORT RESPULES suspension and a modified PULMICORT RESPULES-based SAE-CD solution. PULMICORT RESPULES suspension with and without 5% w/v SBE7-β-CD were used as the test samples. The procedure of Example 12 was followed. FIG. 10a depicts the Dv10 and Dv50 data for the solutions run on the PARI LC PLUS air driven jet nebulizer and FIG. 10b depicts the Dv10 and Dv50 data for the solutions run on the MYSTIQUE ultrasonic nebulizer. In each case, the droplet size data for the two different solutions is comparable. However, the budesonide output rate for the two solutions was significantly different. Use of SAE-CD in a nebulization composition, however, results in an increased output rate of budesonide regardless of the format of the nebulizer. The invention, thus, provides a method of increasing the output rate of a corticosteroid-containing suspension-based unit dose formulation being delivered by a nebulizer, the method comprising the step of including SAE-CD in the formulation in an amount sufficient to increase the amount of dissolved corticosteroid in the formulation to form an altered formulation, whereby the output rate of corticoster- SPULES) as detailed below. In each device, the control suspension-based sample was the RESPULES suspension (2 ml containing 500 mg of budesonide). The RAINDROP nebulizer was equipped with a PARI PRONEB ULTRA compressor. The AERONEB GO micropump nebulizer was equipped with the OnQ Aerosol Generator. The total output of budesonide at cessation of aerolization (at sputter) was quantified. The emitted dose and fine particle dose were measured with the cascade impactor. The solution in the nebulizer of the '151 patent comprised budesonide, CAPTISOL, water, and technetium-99 radiolabel in the form of diethylenetriaminepenta-acetic acid as a surrogate marker for budesonide. The data from the two studies is summarized in the table below.

| Aerosol Performance Using NGI Cascade Impactor | | | | |
|---|---|---|---|---|
| | Nebulizer device | | | |
| | AeroNeb Go | | Raindrop/Pari Proneb Ultra | |
| Formulation | CEB #1 | Pulmicort | CEB #2 | Pulmicort |
| Amount of drug (µg)* | 500.00 | 500.00 | 500.00 | 500.00 |
| Nebulization Time (min)+ | 1.0 | 4.0 | 5.0 | 5.5 |
| Amt of drug exiting nebulizer (µg)* | 405.93 | 266.06 | 150.27 | 92.42 |
| Percent of drug exiting nebulizer (%) | 81.26 | 53.24 | 30.03 | 18.49 |
| Amt of drug exiting nebulizer in fine particle fraction (% < 5 µm) (µg)* | 262.17 | 131.73 | 131.44 | 76.27 |
| Percent of drug exiting nebulizer in fine particle fraction (<5 µm,) | 66.33 | 49.54 | 87.43 | 82.55 |
| Percent of total drug in fine particle fraction (< 5 µm, %) | 53.91 | 26.38 | 26.27 | 15.26 |
| MMAD (um, estimated by linear regression) | 4.10 | 5.54 | 2.22 | 2.86 |
| GSD (sigma g, estimated by linear regression) | 2.02 | 1.55 | 2.37 | 2.21 |

*Data normalized to 500 µg budesonide in each nebulizer using total of recovered drug.
+Note:
Nebulizers were run 30 seconds past end of nebulization time to insure complete emptying into the NGI impactor.

oid for the altered formulation is greater than the output rate of corticosteroid for the suspension formulation.

Two pulsating membrane nebulizers (AERONEB GO and the nebulizer of U.S. Pat. No. 6,962,151) were evaluated according to Examples 21 and 22, respectively, to determine the performance of the devices with a solution of the invention and to demonstrate the utility of using concentrated solutions of corticosteroids in an efficient electronic nebulizer. Several in vitro parameters, important for the clinical use of corticosteroids, were determined and compared to these parameters of the solution formulation described in Example 6 and the 2 mL commercial reference suspension both in an air jet nebulizer. The total delivery/nebulization time (time to sputter where production of aerosol is no longer visible), MMAD droplet size and fine particle fraction parameters were obtained for each device. A cascade impactor was engaged with the output of each device to determine performance during nebulization and characterize the in vitro aerosol drug output.

The solution used in the AERONEB GO device was compared side-by-side with a RAINDROP air jet nebulizer employing a solution (0.5 ml) comprising budesonide (500 µg/0.5 ml), CAPTISOL (10% w/v), water, and Tween 80 (optional), wherein the solution was made by adding CAPTISOL to a suspension of budesonide particles (RE- Using the electronic pulsating membrane nebulizers (AERONEB GO nebulizer and the nebulizer of the '151 patent), delivery of a unit dose of corticosteroid was completed within less than one minute. The RAINDROP nebulizer completed delivery of a unit dose in just over 5.5 min with the RESPULES and just over 5 min with a solution of the invention. In addition, the pulsating membrane nebulizers delivered a substantially greater percentage of corticosteroid in the FPF, which is generally defined as the fraction of particles less than 5µ a or the fraction of particles on cascade impactor stages with a cut-off of less than 6µ. Accordingly, the total nebulization time of the AERONEB GO is one fourth the time to sputter for the Pari LC+ air jet nebulizer. As a result, treatment time would be reduced with the pulsating membrane nebulizer as compared to the air jet nebulizer, and the amount of budesonide emitted from the pulsating membrane nebulizer is 2 to 3 times more than from the air jet nebulizer. It was also determined that the percent of drug exiting the nebulizer (the emitted dose) was 81% of the amount initially loaded into the reservoir (the nominal dose). Hence, less drug would need to be loaded into the pulsating membrane nebulizer to treat the patient in need thereof to provide the same "dose to subject" as provided by an air jet nebulizer.

Aerosol droplet size was determined using a Malvern Spraytec instrument. The Dv10, Dv50, and Dv90 from the pulsating membrane nebulizer are very similar to those for the reference product (PULMICORT RESPULES) and a CAPTISOL solution of the same concentration in an air jet nebulizer This suggests that the formulation would be similarly distributed within the patient after inhalation.

A clinical study according to Example 17 was conducted to compare the pulmonary disposition of budesonide from a radiolabeled liquid formulation and the clearance of budesonide from the lung as determined by appearance of budesonide in the plasma. A solution formulation of the invention was compared to a suspension-based formulation of budesonide. At various times up to 24 hours, plasma samples were collected and assayed for budesonide and various pharmacokinetic parameters determined. The area under the plasma concentration—time curve (AUC) is a measure of the delivery of budesonide to the lung, since oral absorption of the corticosteroid was blocked by the administration of charcoal. A comparison of the AUC data was made by consideration of the dose delivered to each subject ("dose to subject") or dose delivered to the lungs of each subject ("dose to lung") or dose emitted by the nebulizer or device ("emitted dose") or dose available for nebulization or delivery ("nominal dose" or "nominal available dose" or "loaded dose"). The AUC data ($_{0-t}$, and $_{0-\infty}$) was normalized in terms of the budesonide (μg) delivered to each subject by dividing the AUC data by the corresponding dose to subject. As used herein the term "dose to subject" is taken to mean the amount of corticosteroid delivered to a subject following completion of a dosing cycle with a nebulizer and is calculated by subtracting the sum of drug remaining in the nebulizer, drug removed from the mouth of a subject, and the amount collected from the exhalation filter from the amount of drug initially present in the reservoir of the nebulizer. The following expression can be used to calculate the dose to subject (Ds): $Ds=Dr_{init}-(D_{mw}+D_{dev})$, wherein $Dr_{init}$ denotes the amount of drug initially present in the reservoir of the nebulizer, $D_{mw}$ denotes the amount of drug removed from the mouth of a subject by using a mouthwash, $D_{dev}$ denotes the amount of drug remaining in the device following completion of an administration dosing cycle. The term $D_{dev}$ includes drug remaining in the reservoir after completion of dosing, and drug remaining in the remainder of the device after completion of dosing. As used herein, the term "dose to lung" is taken to mean the amount of drug delivered to the lungs of a subject, which amount is a subset of "dose to subject". The dosing parameters used in this example are detailed below and are provided on the basis of arithmetic means.

| | | Arithmetic Means | | | |
|---|---|---|---|---|---|
| | Parameter | Captisol Enabled Budesonide | | | Pulmicort Respules |
| Normalization | or Ratio | 25% TTS | 50% TTS | 75% TTS | 100% TTS |
| Intended | μg | 1000 | 1000 | 1000 | 1000 |
| Nominal | Ratio | 1 | 1 | 1 | 1 |
| Loaded Dose | CEB/PR | | | | |
| Nominal | μg | 250 | 500 | 750 | 1000 |
| Available | Ratio | 0.25 | 0.50 | 0.75 | 1 |
| Dose | CEB/PR | | | | |
| Dose to Lung | μg | 39.56 | 63.85 | 94.38 | 90.17 |
| | | Range = | Range = | Range = | Range = |
| | | 24.61→65.65 | 48.27→80.70 | 72.81→123.79 | 76.21→100.75 |
| | Ratio | 0.44 | 0.72 | 1.05 | 1 |
| | CEB/PR | Range = | Range = | Range = | |
| | | 0.27→0.78 | 0.57→0.95 | 0.87→1.46 | |
| Dose to | μg | 64.1 | 109.1 | 169.8 | 199.9 |
| Subject | | Range = | Range = | Range = | Range = |
| | | 47.57→81.75 | 85.43→156.67 | 142.48→219.03 | 159.58→249.88 |
| | Ratio | 0.33 | 0.55 | 0.86 | 1 |
| | CEB/PR | Range = | Range = | Range = | |
| | | 0.23→0.48 | 0.41→0.64 | 0.74→1.04 | |
| Emitted Dose | μg | 119.5 | 205.9 | 321.8 | 440.2 |
| | | Range = | Range = | Range = | Range = |
| | | 93.40→166.2 | 164.0→272.9 | 277.9→391.0 | 396.7→481.10 |
| | Ratio | 0.27 | 0.47 | 0.73 | 1 |
| | CEB/PR | Range = | Range = | Range = | |
| | | 0.20→0.37 | 0.41→0.57 | 0.66→0.87 | |

The pharmacokinetic data obtained from the study of Example 17 is summarized below. The data is presented on a geometric mean or individual subject basis. The data in the table below is based upon the "dose to subject".

|  |  | Captisol Enabled Budesonide Geometric Means | | | Pulmicort Respules |
| --- | --- | --- | --- | --- | --- |
|  | Parameter | 25% TTS[1] Dose to Subject = 62.7 μg Range[3] = 47.6 →81.8 | 50% TTS[1] Dose to Subject = 107.1 μg Range[3] = 85.4 →156.7 | 75% TTS[1] Dose to Subject = 168.2 μg Range[3] = 142.5 →219.0 | 100% TTS Dose to Subject = 197.7 μg Range[3] = 159.6 →249.9 |
| Non-normalized | $AUC_{0-t}$ (pg · h/ml) | 370 Range = 162 →1209 | 875 Range = 647 →1122 | 1130 Range = 865 →1588 | 516 Range = 378 →631 |
|  | $AUC_{0-\infty}$ (pg · h/ml) | 533 Range = 279 →1309 | 1022 Range = 778 →1285 | 1617 Range= 978 →2351 | 644 Range = 421 →864 |
| Normalized for dose to subject | $AUC_{0-t}$ (pg · h/ml)/μg | 6 Range = 3 →15 | 8 Range = 7 →11 | 7 Range = 4 →11 | 3 Range = 2 →5 |
|  | $AUC_{0-\infty}$ (pg · h/ml)/μg | 8 Range = 4 →16 | 10 Range = 8 →12 | 10 Range = 5 →16 | 3 Range = 2 →5 |

[1]TTS = Time to Sputter. The percentage value can be used to calculate a nominal available dose for the corticosteroid in the study conducted according to Example 17.
[2]Using the added radioactive tracer, the dose of budesonide delivered may be calculated by subtracting the amount of budesonide remaining in the nebulizer post-dose, on the exhalation filter, and in the mouthwash from the amount initially added to the nebulizer.
[3]The ranges in the table above are based upon the geometric means for a respective value as determined with each individual.

Figure 17:
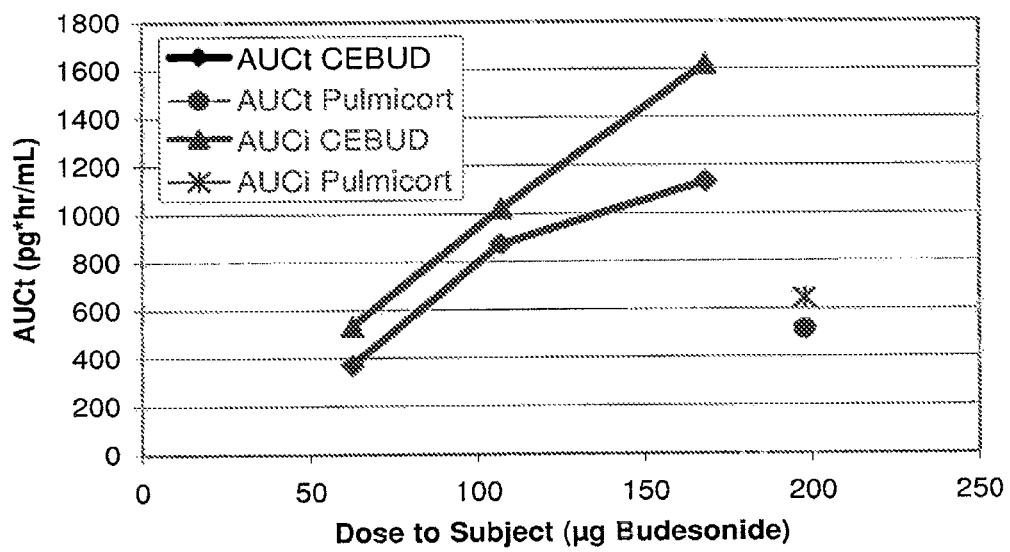
FIG. 17 depicts a plot of the geometric mean of dose (of corticosteroid, μg) to subject versus the geometric mean of AUC (pg*hr/ml) when budesonide is administered to subjects according to Example 17.
Figure 18:
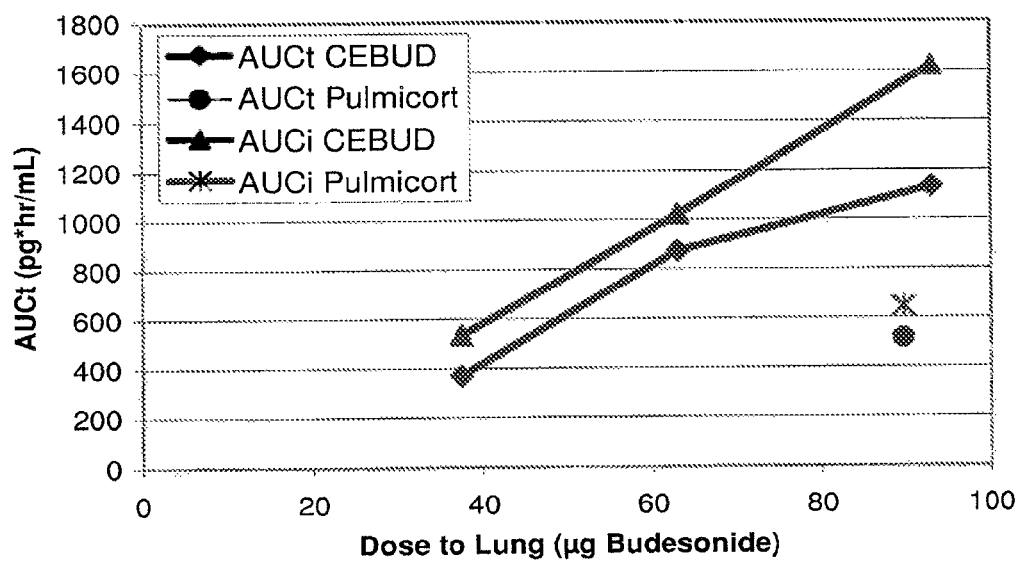
FIG. 18 depicts a plot of the geometric mean of dose (of corticosteroid, μg) to lung of subject versus the geometric mean of AUC (pg*hr/ml) when budesonide is administered to subjects according to Example 17.

Based upon the above data, the formulation of the invention provides a normalized AUCt of 3-15 (or about at least 6) (pg*h/ml)/μg of budesonide when about 60-65 μg of budesonide were delivered, a normalized AUCt of 7-11 (or about at least 8) (pg*h/ml)/μg of budesonide when about 105-110 μg of budesonide were delivered, and a normalized AUCt of 4-11 (or about at least 7) (pg*h/ml)/μg of budesonide when 165-170 μg of budesonide were delivered, based upon the "dose to subject". In addition, the formulation of the invention provided a normalized AUCi of 4-16 (or about at least 8) (pg*h/ml)/μg of budesonide when about 60-65 μg of budesonide were delivered, a normalized AUCi of 8-12 (or about at least 10) (pg*h/ml)/μg of budesonide when about 105-110 μg of budesonide were delivered, and a normalized AUCi of 5-16 (or about at least 10) (pg*h/ml)/μg of budesonide when 165-170 μg of budesonide were delivered, based upon the "dose to subject". The data is also summarized in FIG. 17, which is a plot of the geometric mean of "dose to subject" (μg budesonide) versus the geometric mean of AUC (pg*h/ml), and FIG. 18, which is a plot of the geometric mean of "dose to lung" (μg budesonide) versus the geometric mean of AUC (pg*h/ml).

In some embodiments, the invention includes a method of providing in a subject a mean plasma AUCt, normalized for dose of corticosteroid to subject, of at least 6 (pg*h/ml)/pg of corticosteroid delivered, as dose to subject, comprising: administering to the subject via nebulization a unit dose comprising at least 45 μg, at least 48 μg, or 45 μg to 1000 μg, about 1 μg to 20 mg, about 1 μg to 10 mg, 0.01 mg to 10 mg, 0.025 mg to 10 mg, 0.05 mg to 5 mg, 0.1 mg to 5 mg, 0.125 mg to 5 mg, 0.25 mg to 5 mg, 0.5 mg to 5 mg, 0.05 mg to 2 mg, 0.1 mg to 2 mg, 0.125 mg to 2 mg, 0.25 mg to 2 mg, or 0.5 mg to 2 mg of corticosteroid dissolved in an aqueous liquid carrier comprising sulfoalkyl ether cyclodextrin.

Figure 19:
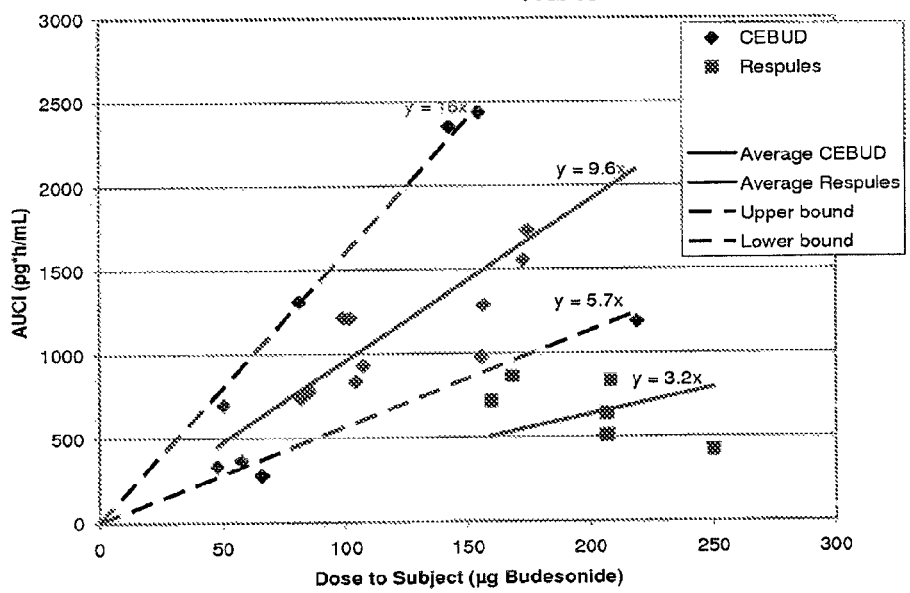
FIG. 19 depicts a plot of dose (of corticosteroid, μg) to subject versus the AUC (pg*hr/ml) for each individual when budesonide is administered to subjects according to Example 17.
Figure 20:
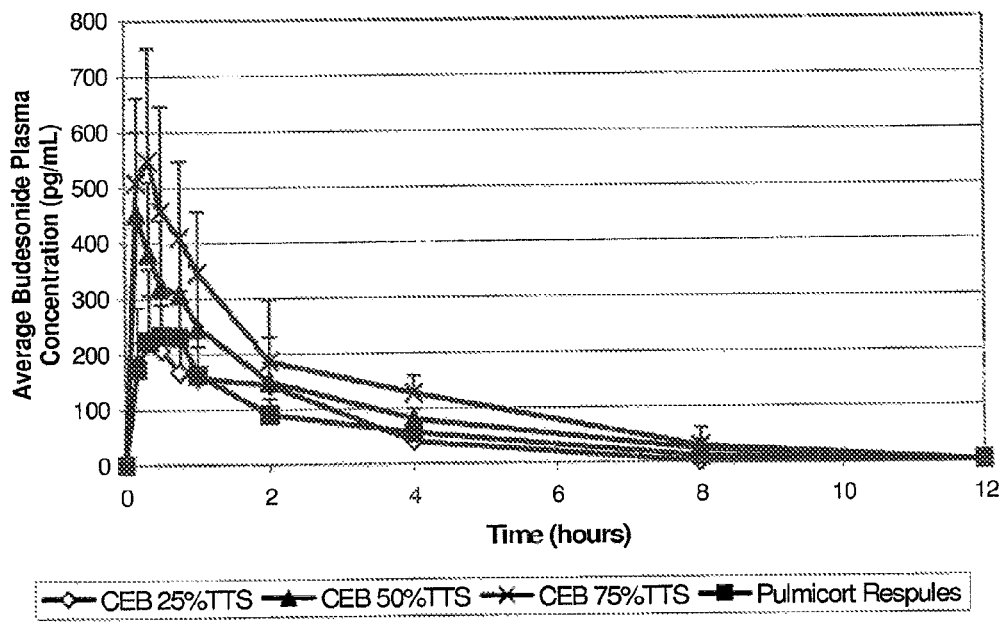
FIG. 20 depicts a plasma concentration profile for budesonide for individual subjects according to Example 17.

FIG. 19 is a plot of the "dose to subject" (μg budesonide) versus the corresponding AUC (pg*h/ml) for each individual subject of the study. The slope of the substantially linear solid line, taken from data across three different doses delivered, defines a dose response curve for a patient receiving the corticosteroid. As a result, the slope can be used to predict the dose a patient would need to provide a target plasma level at a second dose if the patient has received a first dose and the patient's AUC per μg of corticosteroid has been determined. The slope ranges from 5.7 to 16, or more specifically from 9 to 10, when the data is viewed on an individual subject basis The plasma concentration profile for budesonide for the subjects of the clinical study is depicted in FIG. 20.

This normalized AUC data and associated radiolabel distribution data show that more of the dose delivered to the subject made it into the lung and from there into systemic circulation when budesonide was administered as a solution than when the budesonide was administered as a suspension. Assuming that an equivalent dose deposited in the lung results in a similar efficacy and systemic absorption, these results suggest that 1.6 to 5 times or 2 to 4 times less dose to subject is required when administered in solution to be as effective as the reference suspension product. Depending upon whether it is determined on an individual basis or a geometric mean basis, administration of a solution of the invention provides a 1.6-fold increase, 2.2-fold increase, a 2.5-fold increase, a five-fold increase, a 1.6 to five fold increase, a two to four-fold increase, a two to 3.5-fold increase, a two to 3.3-fold increase or at least a two-fold increase in the AUCt or AUCi per μg of budesonide delivered as compared to administration of the PULMICORT RESPULES suspension-based aqueous formulation. The AUCt or AUCi per μg of budesonide delivered was observed as varying per individual, with the value being higher than the above-noted values for some individuals and lower than the above-noted values for other individuals.

The data in the table below is based upon the various different doses measured or determined during the study and summarizes the level (factor) of enhancement in the pharmacokinetic profile parameter $C_{max}$ non-normalized or normalized on the basis of nominal available dose, dose to lung, dose to subject, or emitted dose.

|  |  | Geometric Means | | | |
| --- | --- | --- | --- | --- | --- |
|  |  | Captisol Enabled Budesonide | | | Pulmicort Respules |
| Normalization | Parameter or Ratio | 25% TTS | 50% TTS | 75% TTS | 100% TTS |
| Non-normalized | $C_{max}$ (pg/mL) | 225.8 Range = 91.6→483.3 | 437.2 Range = 297.1→739.1 | 545.5 Range = 376.6→891.6 | 266.3 Range = 155.8→331.5 |
|  | Ratio CEB/PR | 0.85 Range = 0.55→1.55 | 1.64 Range = 0.90→2.60 | 2.05 Range = 1.50→2.86 | 1 |
| Normalized for nominal available dose[1] | (pg/mL) μg | 0.90 Range = 0.37→1.93 | 0.87 Range = 0.59→1.48 | 0.73 Range = 0.50→1.19 | 0.27 Range = 0.16→0.33 |
|  | Ratio CEB/PR | 3.39 Range = 2.20→6.21 | 3.28 Range = 1.79→5.20 | 2.73 Range = 2.01→3.82 | 1 |
| Normalised for dose to lung[2] | (pg/mL) μg | 6.03 Range = 3.49→8.51 | 6.93 Range = 5.49→9.16 | 5.86 Range = 4.52→7.45 | 2.97 Range = 1.59→3.95 |
|  | Ratio CEB/PR | 2.03 Range = 1.48→2.59 | 2.33 Range = 1.56→4.30 | 1.97 Range = 1.38→3.17 | 1 |
| Normalised for dose to subject[3] | (pg/mL) μg | 3.60 Range = 1.93→5.94 | 4.08 Range = 3.22→7.44 | 3.24 Range = 1.72→5.23 | 1.35 Range = 0.75→1.85 |
|  | Ratio CEB/PR | 2.67 Range = 1.99→3.21 | 3.03 Range = 2.17→5.01 | 2.41 Range = 1.72→3.76 | 1 |
| Normalized for emitted dose[4] | (pg/mL) μg | 1.93 Range = 0.98→2.91 | 2.15 Range = 1.71→3.25 | 1.71 Range = 1.00→2.68 | 0.61 Range = 0.34→0.84 |
|  | Ratio CEB/PR | 3.18 Range = 2.19→4.20 | 3.55 Range = 2.17→6.26 | 2.82 Range = 1.93→4.23 | 1 |

According to the table above, the formulation and system of the invention can provide a $C_{max}$ (pg/ml) of 90 to 900, 200 to 600, 200 to 550, 200 to 250, 400 to 450, 500 to 600, 225, 437, or 545 on a dose non-normalized basis. The formulation and system of the invention can provide a dose normalized $C_{max}$ (pg/ml/μg) of: 1) 0.3 to 2, 0.35 to 2, 0.6 to 1.5, 0.5 to 1.2, 0.8 to 1, 0.8 to 0.9, 0.7 to 0.8, 0.4, 1.9, 0.6, 1.5, 0.5, 1.2, 0.35, 2, 0.7, 0.8, or 0.9 on a nominal available dose normalized basis; 2) 3.4 to 9.2, 3.5 to 8.5, 5.5 to 9.2, 4.5 to 7.5, 5.8 to 7, 3.4, 3.5, 4.5, 5.5, 9.2, 8.5, 7.5, 5.8, 5.9, 6, or 7 on a dose to lung normalized basis; 3) 1.7 to 7.5, 3.2 to 4.1, 1.9 to 6, 3.2 to 7.5, 1.7 to 5.2, 3.6, 4.1, 3.2, 1.9, 6, 3.2, 7.4, 7.5, 1.7, 5.2 or 5.3 on a dose to subject normalized basis; 4) 0.9 to 3.3, 1.7 to 2.2, 0.9 to 3, 1 to 3, 1.7 to 3.3, 1 to 2.7, 1.9, 2.1, 2.2, 1.7, 0.9, 1, 2, 3, 2.9, 3.2, 3.3, or 2.7 on an emitted dose normalized basis.

The solution of the invention provides an enhanced pharmacokinetic profile over the suspension-based formulation. On the basis of the non-normalized dose of corticosteroid, the Cmax provided by the corticosteroid solution is 1.6 to 2, 1.5 to 3, 1.5 to 2.5, 1.5 to 2, 1.5, 1, 6, 2, 2.5, or 3 fold higher than the Cmax provided by the suspension-based formulation when the dose of corticosteroid in the solution and the suspension is approximately the same amount loaded. On the basis of normalization to the nominal available dose of corticosteroid, the Cmax provided by the corticosteroid solution is 1.8 to 6.2, 1.5 to 6.5, 2 to 6.5, 1.5 to 5.5, 2 to 4, 1.5 to 4, 1.5 to 3, 2.7, 3.3, 3.4, 1.5, 6.5, 2, 5.5, 4, or 3 fold higher than the Cmax provided by the suspension-based formulation. On the basis of normalization to the dose of corticosteroid to lung, the Cmax provided by the corticosteroid solution is 1.4 to 4.3, 1.4 to 4.5, 1.5 to 4.5, 1.5 to 3.5, 1.5 to 3, 1.4 to 3, 1.5 to 2.5, 1.5 to 2, 2, 2.3, 1.4, 4.5, 3.5, 3, 1.5 or 2.5 fold higher than the Cmax provided by the suspension-based formulation. On the basis of normalization to the dose of corticosteroid to subject, the Cmax provided by the corticosteroid solution is 2 to 3.5, 2 to 5, 1.7 to 3.8, 1.7 to 5, 2.7, 3, 2.4, 2, 3.5, 5, 1.7, or 3.8 fold higher than the Cmax provided by the suspension-based formulation. On the basis of normalization to the emitted dose of corticosteroid, the Cmax provided by the corticosteroid solution is 1.9 to 6.3, 1.75 to 6.5, 2.2 to 4.2, 2.2 to 6.3, 1.9 to 4.2, 3.2, 3.5, 3.6, 2.8, 1.75, 6.5, 2.2, 4.2, or 6.3 fold higher than the Cmax provided by the suspension-based formulation.

Alternatively, the Cmax provided by the corticosteroid solution is at least 1.5, 1.6, 2, 2.6, and 3 fold higher than the Cmax provided by the suspension-based formulation when the dose of corticosteroid in the solution is about 2 fold lower than the dose in the suspension.

The data in the table below is based upon the various different doses measured or determined during the study and summarize the level (factor) of enhancement in the pharmacokinetic profile parameter $AUC_{inf}$ non-normalized or normalized on the basis of nominal available dose, dose to lung, dose to subject, or emitted dose.

|  |  | Geometric Means | | | |
| --- | --- | --- | --- | --- | --- |
|  | Parameter | Captisol Enabled Budesonide | | | Pulmicort Respules |
| Normalization | or Ratio | 25% TTS | 50% TTS | 75% TTS | 100% TTS |
| Non-normalized | AUCinf (pg*h/mL) | 533.0 Range = 278.6→1309 | 1022.2 Range = 777.5→1285 | 1616.8 Range = 977.5→2438.2 | 643.6 Range = 420.6→864.1 |
|  | Ratio CEB/PR | 0.83 Range = 0.44→1.51 | 1.59 Range = 1.00→3.06 | 2.51 Range = 1.53→3.28 | 1 |
| Normalized for nominal available dose | (pg*h/mL) μg | 2.13 Range = 1.11→5.23 | 2.04 Range = 1.55→2.57 | 2.16 Range = 1.30→3.25 | 0.64 Range = 0.42→0.86 |
|  | Ratio CEB/PR | 3.31 Range = 1.77→6.06 | 3.18 Range = 2.00→6.11 | 3.35 Range = 2.04→4.37 | 1 |
| Normalized for dose to lung | (pg*h/mL) μg | 14.24 Range = 10.17→19.94 | 16.20 Range = 13.59→18.77 | 17.37 Range = 11.16→24.69 | 7.17 Range = 5.52→10.22 |
|  | Ratio CEB/PR | 1.98 Range = 1.19→2.85 | 2.26 Range = 1.47→3.40 | 2.42 Range = 1.37→3.52 | 1 |
| Normalized for dose to subject | (pg*h/mL) μg | 8.50 Range = 4.23→16.08 | 9.54 Range = 8.01→12.23 | 9.61 Range = 5.41→16.5 | 3.26 Range = 1.68→5.14 |
|  | Ratio CEB/PR | 2.61 Range = 1.60→3.64 | 2.93 Range = 2.00→4.87 | 2.95 Range = 1.93→3.93 | 1 |
| Normalized for emitted dose | (pg*h/mL) μg | 4.55 Range = 2.62→7.87 | 5.04 Range = 4.23→6.66 | 5.07 Range = 3.16→8.48 | 1.43 Range = 0.81→2.31 |
|  | Ratio CEB/PR | 3.18 Range = 1.92→5.37 | 3.52 Range = 2.31→5.82 | 3.55 Range = 1.91→5.47 | 1 |

According to the table above, the formulation and system of the invention can provide an $AUC_{inf}$ (pg*h/ml) of 500 to 1700, 530 to 1650, 250 to 2500, 280 to 1300, 780 to 1300, 980 to 2450, 275, 775, 980, 2400, 2500, 1300, 1290, 530, 1650, 250, 280 or 780 on a dose non-normalized basis. The formulation and system of the invention can provide a dose normalized $AUC_{inf}$ (pg/ml/μg) of: 1) 1 to 5.5, 2 to 2.2, 1 to 5.3, 1.1 to 5.2, 1.5 to 2.6, 1.3 to 3.3, 2, 2.1, 2.2, 1, 5.5, 5.3, 5.2, 1.5, 2.6, 1.3 or 3.3 on a nominal available dose normalized basis; 2) 10 to 25, 14 to 18, 10.2 to 20, 13.6 to 18.8, 11.2 to 24.7, 10.2, 20, 13.6, 14, 19, 18.8, 11, 11.2, 25, 24.7, 14.2, 16.2, 17.3 on a dose to lung normalized basis; 3) 4 to 16, 4.2 to 16.1, 8 to 12.2, 5.4 to 16, 5.4 to 17, 8.5 to 9.6, 8.5, 9.5, 9.6, 4.2, 16.1, 8, 12.2, 12, 5.4, 16, 17, or 16.5 on a dose to subject normalized basis; 4) 2.5 to 9, 2.6 to 8.5, 4.5 to 5.1, 2.5 to 8, 2.6 to 7.9, 4.2 to 6.7, 3.1 to 8.5, 3.2 to 8.5, 4.5, 4.6, 5, 5.1, 2.5, 2.6, 4.2, 3.1, 9, 8.5, 5.1, 8, 7.9, or 6.7 to on an emitted dose normalized basis.

Accordingly, the solution of the invention provides an enhanced pharmacokinetic profile over the suspension-based formulation. On the basis of the non-normalized dose of corticosteroid, the $AUC_{inf}$ provided by the corticosteroid solution is 1.6 to 2.5, 1.6 to 3.1, 1.5 to 3.5, 1.5 to 3.3, 2.5 to 3.3, 3.1, 1.5, 3.3, 1.6, or 2.5 fold higher than the $AUC_{inf}$ provided by the suspension-based formulation when the dose of corticosteroid in the solution and the suspension is approximately the same. On the basis of normalization to the nominal available dose of corticosteroid, the $AUC_{inf}$ provided by the corticosteroid solution is 1.75 to 6.5, 1.75 to 6.1, 2 to 6.5, 2 to 6.1, 2 to 4.5, 2 to 4.4, 3.3, 3.2, 3.5, 3.4, 1.75, 6.5, 6.1, 2, 4.5, or 4.4 fold higher than the $AUC_{inf}$ provided by the suspension-based formulation. On the basis of normalization to the dose of corticosteroid to lung, the $AUC_{inf}$ provided by the corticosteroid solution is 1.2 to 3.5, 1.2 to 4, 1.2 to 3, 1.2 to 2.85, 1.5 to 3.5, 1.4 to 3.5, 2, 2.2, 2.3, 2.4, 1.2, 3, 4, 2.85, 1.5, 3.5, or 1.4 fold higher than the $AUC_{inf}$ provided by the suspension-based formulation. On the basis of normalization to the dose of corticosteroid to subject, the $AUC_{inf}$ provided by the corticosteroid solution is 1.6 to 4.9, 1.5 to 5, 1.6 to 5, 1.6 to 3.7, 1.6 to 3.6, 2 to 4.9, 1.9 to 4, 2.6, 1.5, 5, 1.6, 3.7, 3.6, 2, 4.9, 1.9, or 4 fold higher than the $AUC_{inf}$ provided by the suspension-based formulation. On the basis of normalization to the emitted dose of corticosteroid, the $AUC_{inf}$ provided by the corticosteroid solution is 1.5 to 6, 1.7 to 6, 1.9 to 6, 1.9 to 5.4, 2.3 to 5.8, 1.9 to 5.5, 1.9 to 5.8, 1.5, 6, 1.7, 1.9, 5.4, 2.3, 5.8, 5.8, 3.2, 3.5, or 3.6 fold higher than the $AUC_{inf}$ provided by the suspension-based formulation.

Alternatively, the $AUC_{inf}$ provided by the corticosteroid solution is at least 1.5, 1.6, 2, 2.5, 3 and 3.1 fold higher than the $AUC_{inf}$ provided by the suspension-based formulation when the dose of corticosteroid in the solution is about 2 fold lower than the dose in the suspension.

The data in the table below is based upon the various different doses measured or determined during the study and summarize the level (factor) of enhancement in the pharmacokinetic profile parameter $AUC_{last}$ non-normalized or normalized on the basis of nominal available dose, dose to lung, dose to subject, or emitted dose.

|  |  | Geometric Means | | | |
| --- | --- | --- | --- | --- | --- |
|  | Parameter | Captisol Enabled Budesonide | | | Pulmicort Respules |
| Normalization | or Ratio | 25% TTS | 50% TTS | 75% TTS | 100% TTS |
| Non-normalized | AUCtlast (pg*h/mL) | 396.7 Range = 162.3→1209 | 874.5 Range = 646.7→1122 | 1130 Range = 864.6→1588 | 516.2 Range = 377.6→630.9 |
|  | Ratio | 0.77 | 1.69 | 2.19 | 1 |
|  | CEB/PR | 0.32→1.92 | 1.14→2.97 | 1.55→2.93 |  |
| Normalized for nominal available dose [1] | (pg*h/mL) | 1.59 | 1.75 | 1.51 | 0.52 |
|  | µg | 0.65→4.84 | 1.29→2.24 | 1.15→2.12 | 0.38→0.63 |
|  | Ratio | 3.07 | 3.39 | 2.92 | 1 |
|  | CEB/PR | 1.29→7.66 | 2.28→5.94 | 2.07→3.90 |  |
| Normalized for dose to lung [2] | (pg*h/mL) | 10.60 | 13.86 | 12.14 | 5.75 |
|  | µg | 6.18→18.41 | 11.12→16.82 | 9.44→17.96 | 4.96→7.47 |
|  | Ratio | 1.84 | 2.41 | 2.11 | 1 |
|  | CEB/PR | 1.21→2.49 | 1.68→3.31 | 1.53→3.38 |  |
| Normalized for dose to subject [3] | (pg*h/mL) | 6.33 | 8.16 | 6.72 | 2.61 |
|  | µg | 3.34→14.85 | 6.56→10.74 | 3.95→11.15 | 1.51→3.75 |
|  | Ratio | 2.42 | 3.13 | 2.57 | 1 |
|  | CEB/PR | 1.40→3.96 | 2.27→4.74 | 2.09→3.50 |  |
| Normalized for emitted dose [4] | (pg*h/mL) | 3.39 | 4.31 | 3.54 | 1.18 |
|  | µg | 1.74→7.27 | 3.46→6.01 | 2.30→5.72 | 0.78→1.42 |
|  | Ratio | 2.88 | 3.67 | 3.02 | 1 |
|  | CEB/PR | 1.59→5.19 | 2.52→5.24 | 2.36→4.03 |  |

Figure 22:
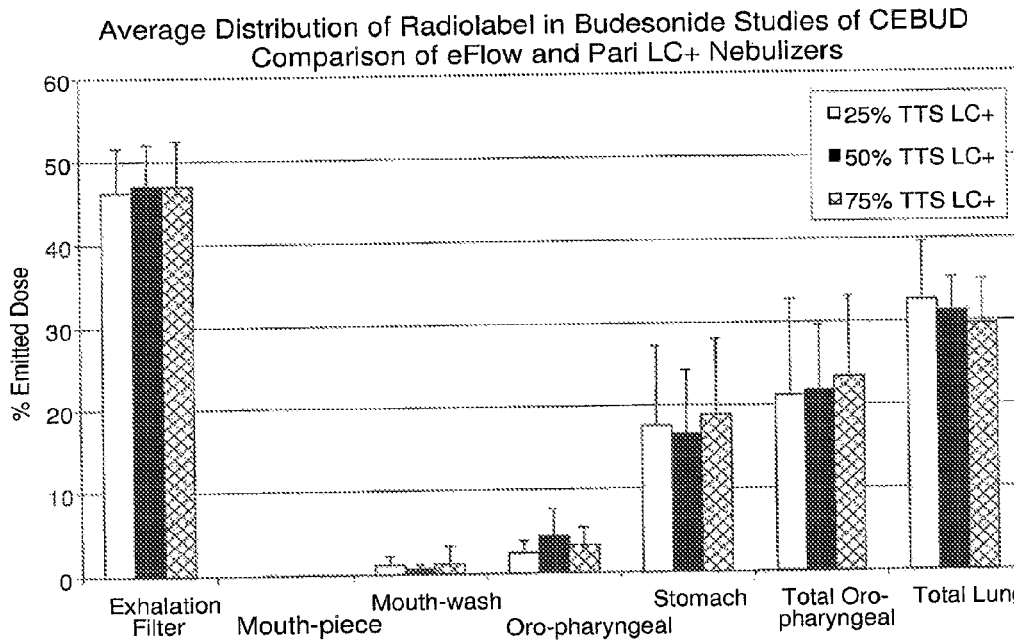
FIG. 22 is a chart detailing the approximate distribution of a dose of budesonide upon administration of a solution of the invention according the procedure of Example 17.

A determination of dose distribution in subjects (Example 17) was made to determine the efficiency of dose deposition to the lungs. The results are detailed in the table below and in FIG. 22.

|  | 1(A) | 2(B) | 3(C) | 4(D) |
| --- | --- | --- | --- | --- |
|  | Lung Scintigraphy (mean values) | | | |
| Dose in lungs (µg) | 90.17 | 39.56 | 63.85 | 94.39 |
| % wt. in lungs | 20.61 | 32.61 | 31.30 | 29.61 |
| % wt. in oropharyngeal/ stomach region | 24.79 | 21.13 | 21.68 | 23.39 |
| % wt. in exhalation filter/mouthpiece | 54.61 | 46.26 | 47.02 | 47.00 |
| Mass Balance | 100.47 | 100.97 | 103.21 | 103.49 |

1(A) Budesonide Suspension nebulized to sputter—100% TTS (time to sputter)
2(B) Captisol-Enabled ® Budesonide Formulation—25% TTS
3(C) Captisol-Enabled ® Budesonide Formulation—50% TTS
4(D) Captisol-Enabled ® Budesonide Formulation—75% TTS The data demonstrate that administration of the solution of the invention resulted in a lower oropharyngeal deposition of the corticosteroid as compared to administration of the control suspension formulation. Moreover, the formulation provided at least a 20% to 85%, or 30% to 80%, or at least 30%, at least 40%, at least 56%, at least 59%, at least 62% wt. pulmonary deposition of corticosteroid based upon the emitted dose. The percentage of pulmonary deposition can be further increased by employing a nebulizer capable of providing a higher respirable fraction and lower MMAD for the nebulized mist. Suitable nebulizers are ultrasonic, vibrating mesh, vibrating cone, vibrating plate nebulizers or those that extrude a liquid formulation through a self-contained nozzle array. For example, the Aradigm AERx pulmonary delivery systems, the AERx Essence and AERx Ultra, is particularly suitable for use according to the invention, as it is recognized in the art as providing controlled dose expression, control of generated aerosol particle size, control of inhaled aerosol particle size, and management of the inhalation and delivery process (Farr et al., Drug Delivery Technology May 2002 Vol. 2, No. 3, 42-44). For example, the PARI eFlow vibrating plate nebulizer is particularly suitable for use according to the invention, as it is recognized in the art as providing the above-mentioned desired performance parameters (Keller et al. (ATS 99th International Conference, Seattle, May 16-21, 2003; poster 2727).

By virtue of the improved systemic bioavailability of a corticosteroid delivered to the lungs by pulmonary administration according to the invention, the composition or formulation of the invention will provide an improved therapeutic benefit or improved clinical benefit over an equivalent dose of corticosteroid administered as an aqueous suspension.

Figure 21:
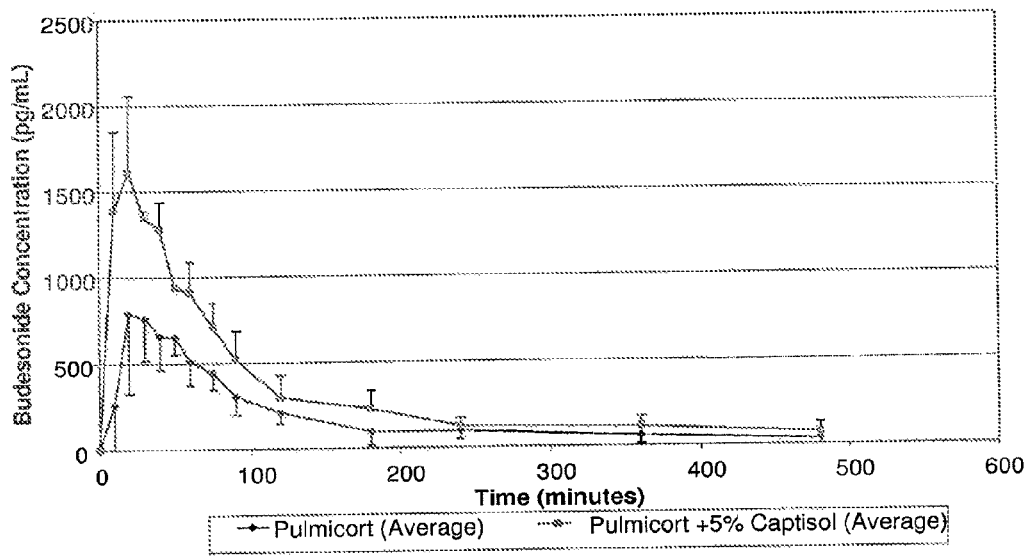
FIG. 21 depicts a plasma concentration profile for budesonide for dogs according to Example 31.

Example 30 details a study conducted on dogs wherein a budesonide solution of the invention and a reference formulation (PULMICORT RESPULES suspension) was administered via nebulization with a Pari LC air-jet nebulizer. The results depicted in FIG. 21 demonstrate an average plasma level of budesonide as a function of time. The $AUC_{0 \to 8 \, hr}$ of the solution formulation was 1.9 times greater than the reference suspension formulation. The solution formulation also emitted 1.23 times as much budesonide as the reference formulation in the same length of time. Detailed results are also provided in the table below.

|  | Dog PK Study | | |
| --- | --- | --- | --- |
| Parameter | Captisol Enabled Budesonide | Pulmicort Respules | Ratio CEB/PR |
| Loaded Dose (nominal dose) | 1000 µg | 1000 µg | 1 |
| Emitted Dose | 769 µg | 626 µg | 1.23 |

-continued

Dog PK Study

| Parameter | Captisol Enabled Budesonide | Pulmicort Respules | Ratio CEB/PR |
|---|---|---|---|
| Average $AUC_{0 \to 8\ hr}$ | 2599 pg × hr/mL | 1355 pg × hr/mL | 1.91 |
| Average $C_{max}$ | 1685 pg/mL | 901 pg/mL | 1.87 |
| Loaded Dose—normalized $AUC_{0 \to 8\ hr}$ | 2.60 (pg × hr/mL)/µg | 1.36 (pg × hr/mL)/µg | 1.91 |
| Emitted Dose—normalized $AUC_{0 \to 8\ hr}$ | 3.38 (pg × hr/mL)/µg | 2.16 (pg × hr/mL)/µg | 1.56 |
| Loaded Dose—normalized $C_{max}$ | 1.69 (pg/mL)/µg | 0.90 (pg/mL)/µg | 1.88 |
| Emitted Dose—normalized $C_{max}$ | 2.19 (pg/mL)/µg | 1.44 (pg/mL)/µg | 1.52 |

According to the table above, the formulation and system of the invention can provide an $AUC_{0-8\ hr}$ (pg*h/ml) of 2000 to 3000, 2500 to 2700, 2000, 3000, or 2600 on a dose non-normalized basis. The formulation and system of the invention can provide a dose normalized $AUC_{inf}$ (pg/ml/µg) of: 1) 2 to 3, 2.5 to 2.7, or 2.6 on a loaded dose nominal normalized basis; 2) 3 to 4, 3.4 to 3.5, or 3.4 on an emitted dose normalized basis.

The formulation, system and method of the invention provided a higher $AUC_{0-8\ hr}$ than did the suspension-based PULMICORT RESPULES formulation. On the basis of the normalized nominal (loaded) dose of corticosteroid, the $AUC_{0-8\ hr}$ provided by the corticosteroid solution is at least 1.7, 1.8, 1.9, or 2 fold higher than the $AUC_{0-8\ hr}$ provided by the suspension-based formulation when the dose of corticosteroid in the solution and the suspension is approximately the same. On the basis of normalization to the emitted dose of corticosteroid, the $AUC_{0-8\ hr}$ provided by the corticosteroid solution is at least 1.5, 1.6, to 2 fold higher than the $AUC_{0-8\ hr}$ provided by the suspension-based formulation.

According to the table above, the formulation and system of the invention can provide an $C_{max}$ (pg/ml) of 1600 to 1800, 1650 to 1750, or 1700 on a dose non-normalized basis. The formulation and system of the invention can provide a dose normalized $C_{max}$ (pg/ml/µg) of: 1) 1 to 2, 1.6 to 1.8, or 1.7 on a loaded dose nominal normalized basis; 2)2 to 2.5, or 2.2 on an emitted dose normalized basis.

The formulation, system and method of the invention provided a higher $C_{max}$ than did the suspension-based PULMICORT RESPULES formulation. On the basis of the normalized nominal (loaded) dose of corticosteroid, the C provided by the corticosteroid solution is at least 1.7, 1.8, 1.9, or 2 fold higher than the $C_{max}$ provided by the suspension-based formulation when the dose of corticosteroid in the solution and the suspension is approximately the same. On the basis of normalization to the emitted dose of corticosteroid, the $C_{max}$ provided by the corticosteroid solution is at least 1.5, 1.6, to 2 fold higher than the $C_{max}$ provided by the suspension-based formulation.

In some aspects, the method and dosage form of the invention thus provides an improved method of administering a corticosteroid suspension-based unit dose, the method comprising the step of adding a sufficient amount of SAE-CD to convert the suspension to a clear solution and then administering the clear solution to a subject. As a result, the method of the invention provides increased total delivery of the corticosteroid as well as increased rate of administration as compared to the initial unit dose suspension formulation.

The data herein can also be used to estimate the percentage of the dose of corticosteroid emitted or delivered that is absorbed into the bloodstream of a patient. In some embodiments, greater than 20%, greater than 25%, greater than 29%, greater than 35% of the emitted dose may be absorbed into the bloodstream of the patient. In some embodiments, greater than 40%, greater than 50%, greater than 55% of the dose to subject may be absorbed into the bloodstream of the patient. In some embodiments, greater than 10%, greater than 12%, greater than 15% of the nominal available dose may be absorbed into the bloodstream of the patient.

The corticosteroids that are useful in the present invention generally include any steroid produced by the adrenocortex, including glucocorticoids and mineralocorticoids, and synthetic analogs and derivatives of naturally occurring corticosteroids having anti-inflammatory activity. Suitable synthetic analogs include prodrugs, ester derivatives Examples of corticosteroids that can be used in the compositions of the invention include aldosterone, beclomethasone, betamethasone, budesonide, ciclesonide (Altana Pharma AG), clopredenol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, methylprednisolone, mometasone, paramethasone, prednisolone, prednisone, rofleponide, RPR 106541, tixocortol, triamcinolone, and their respective pharmaceutically acceptable derivatives, such as beclomethasone dipropionate (anhydrous or monohydrate), beclomethasone monopropionate, dexamethasone 21-isonicotinate, fluticasone propionate, icomethasone enbutate, tixocortol 21-pivalate, and triamcinolone acetonide. Particularly preferred are compounds such as beclomethasone dipropionate, budesonide, flunisolide, fluticasone propionate, mometasone furoate, and triamcinolone acetonide. Other corticosteroids not yet commercialized, but that are commercialized subsequent to the filing of this application, are considered useful in the present invention unless it is otherwise established experimentally that they are not suitable.

Corticosteroids can be grouped according to their relative lipophilicity as described by Barnes et al. (*Am. J. Respir. Care Med.* (1998), 157, p. S1-S53), Miller-Larsson et al. (*Am J. Respir. Crit. Care Med.* (2003), 167, A773), D. E. Mager et al. (*J. Pharm. Sci.* (Nov. 2002), 91(11), 2441-2451) or S. Edsbäcker (Uptake, retention, and biotransformation of cortico steroids in the lung and airways. In: Schleimer R P, O'Byrne P M O, Szefler S J, Brattsand R, editor(s). Inhaled steroids in asthma: optimizing effects in the airways. New York: Marcel Dekker, 2002: 213-246). Generally, the less lipophilic a corticosteroid is, the lower the amount of SAE-CD required to dissolve it in an aqueous medium and vice versa. Corticosteroids that are less lipophilic than flunisolide generally require a SAE-CD to corticosteroid molar ratio of less than 10:1 to dissolve the corticosteroid in an aqueous medium. Exemplary corticosteroids of this group include hydrocortisone, prednisolone, prednisone, dexamethasone, betamethasone, methylprednisolone, triamcinolone, and fluocortolone. Some embodiments of the invention exclude corticosteroids that are less lipophilic than flunisolide.

Corticosteroids that are at least as lipophilic as or more lipophilic than flunisolide generally require a SAE-CD to corticosteroid molar ratio of more than 10:1 to dissolve the corticosteroid in an aqueous medium. In some embodiments, the corticosteroid used in the invention is at least as lipophilic as or more lipophilic than flunisolide. Exemplary corticosteroids of this group include beclomethasone, beclomethasone dipropionate, beclomethasone monopropionate, budesonide, ciclesonide, desisobutyryl-ciclesonide, flunisolide, fluticasone, fluticasone propionate, mometasone, mometasone furoate, triamcinolone acetonide.

The suitability of a corticosteroid for use in the inhalable liquid composition/formulation can be determined by performing a phase solubility binding study as detailed in Example 23. Phase solubility binding data is used to determine the saturated solubility of a corticosteroid in the presence of varying amounts of SAE-CD in an aqueous liquid carrier. The phase solubility binding curve depicted in FIG. 3 demonstrates the saturated solubility of budesonide in an aqueous liquid carrier comprising γ-CD, HP-β-CD or SBE7-β-CD. A phase solubility curve in the graph defines the boundary for the saturated solubility the corticosteroid in solutions containing various different concentrations of cyclodextrin. A molar phase solubility curve can be used to determine the molar ratio of SAE-CD to corticosteroid or of corticosteroid to SAE-CD at various concentrations of corticosteroid. The area below the phase solubility curve, e.g. of FIG. 3, denotes the region where the corticosteroid is solubilized in an aqueous liquid medium to provide a substantially clear aqueous solution. In this region, the SAE-CD is present in molar excess of the corticosteroid and in an amount sufficient to solubilize the corticosteroid present in the liquid carrier. The boundary defined by the phase solubility curve will vary according to the corticosteroid and SAE-CD within a composition or formulation of the invention. The table below provides a summary of the minimum molar ratio of SAE-CD to corticosteroid required to achieve the saturated solubility of the corticosteroid in the composition or formulation of the invention under the conditions studied.

| Corticosteroid | SAE-CD | Approximate Molar Ratio at Saturated Solubility of Corticosteroid* (SAE-CD:corticosteroid) |
|---|---|---|
| Beclomethasone dipropionate | SAE-β-CD | 358 |
| Beclomethasone dipropionate | SAE-γ-CD | 62 |
| Budesonide | SAE-β-CD | 16 |
| Budesonide | SAE-γ-CD | 13 (SBE6.1), 10.8 (SBE5.2), 10.1 (SPE5.4) |
| Budesonide | SAE-α-CD | 12 |
| Flunisolide | SAE-β-CD | 16 |
| Flunisolide | SAE-γ-CD | 9 |
| Fluticasone | SAE-β-CD | 32 |
| Fluticasone | SAE-β-CD | 797 |
| Fluticasone Propionate | SAE-γ-CD | 51 |
| Fluticasone Propionate | SAE-α-CD | 501 |
| Mometasone | SAE-α-CD | 73 |
| Mometasone | SAE-β-CD | 33 |
| Mometasone furoate | SAE-α-CD | 141 |
| Mometasone furoate | SAE-β-CD | 274 |
| Mometasone furoate | SAE-γ-CD | 101 |
| Triamcinolone acetonide | SAE-β-CD | 9 |

*This value was determined in the presence of SAE-CD under the conditions detailed in Examples 18, 23 accompanying the solubility values presented in the preceding and following text.

The saturated solubility of a corticosteroid in the presence of a fixed amount of SAE-CD will vary according to the identity of the corticosteroid and the SAE-CD. The table below summarizes some solubility data for the listed corticosteroids in the absence (intrinsic solubility of corticosteroid in the aqueous test medium) and in the presence of two different SAE-CD's as determined herein.

| Steroid | [Steroid] $\times 10^5$ M | | |
|---|---|---|---|
| | Intrinsic Solubility (In $H_2O$) | Captisol (0.04M) | $(SBE)_{6.1}$ γ-CD (0.04M) |
| Hydrocortisone | 92.4 | 2656.3 | 2369.3 |
| Methylprednisolone | 43.6 | 743.1 | 1215.3 |
| Prednisolone | 62.5 | 1995.3 | 2095.0 |
| Prednisone | 50.5 | 1832.7 | 1313.7 |
| Triamcinolone Acetonide | 3.56 | 457.0 | 1059.5 |
| Flunisolide | 11.3 | 261.5 | 455.1 |
| Budesonide | 6.6 | 254.8 | 306.6 |
| Fluticasone Propionate | 0.39 | 5.41 | 51.8 |
| Beclomethasone Dipropionate | 0.41 | 11.6 | 46.8 |
| Mometasone Fuorate | 1.82 | 16.4 | 41.5 |

The above data can be used in combination with the phase solubility data to prepare formulations according to the invention having a target concentration of corticosteroid and SAE-CD. Accordingly, some embodiments of the invention comprise a corticosteroid having an intrinsic solubility in water that approximates or is less than the intrinsic solubility of flunisolide (less than about $11 \times 10^{-5}$ M or less than about $11.3 \times 10^{-5}$ M) in water as determined herein.

Even though a composition or formulation of the invention can comprise the corticosteroid present in an aqueous medium at a concentration up to its saturated solubility in the presence of a particular concentration of SAE-CD, some embodiments of the invention include those wherein the corticosteroid is present at a concentration that is less than its saturated solubility in the presence of that concentration of SAE-CD. The corticosteroid can be present at a concentration that is 95% or less, 90% or less, 85% or less, 80% or less, or 50% or less of its saturated solubility as determined in the presence of SAE-CD. It is generally easier to prepare solutions that comprise the corticosteroid at a concentration that is less than its saturated solubility in the presence of SAE-CD.

Therefore, the molar ratio of SAE-CD to corticosteroid in a formulation or composition of the invention can exceed the molar ratio obtained at the saturated solubility of the corticosteroid in the presence of SAE-CD, such as defined by the phase solubility binding curve for the corticosteroid. In such a case, the molar ratio of SAE-CD to corticosteroid in the composition or formulation will be at least 1%, at least 2%, at least 5%, at least 7.5%, at least 10%, at least 15%, at least 20%, at least 25%, at least 50%, at least 75%, at least 100%, or at least 200% greater than the molar ratio at the saturated solubility of the corticosteroid in the presence of SAE-CD. For example, if the molar ratio at the saturated solubility is about 14:1, then the molar ratio in the composition or formulation can be at least 14.1:1 (for at least 1% higher), at least 14.3:1 (for at least 2% higher), at least 14.7:1 (for at least 5% higher), at least 15.4:1 (for at least 10% higher), at least 16.1:1 (for at least 15% higher), at least 16.8:1 (for at least 20% higher), at least 17.5:1 (for at least 25% higher), at least 21:1 (for at least 50% higher), at least 24.5:1 (for at least 75% higher), at least 28:1 (for at least 100% higher), or at least 42:1 (for at least 100% higher).

Changes in the molar ratio of SAE-CD to corticosteroid can have an impact upon the total output of a nebulizer. A study was conducted using a PARI LC PLUS air jet nebulizer and solutions containing varying amounts of SAE-CD in 2 ml of 250 μg/ml PULMICORT RESPULES. Each preparation was nebulized for until no further sustained vapor was visibly being emitted. At the end of each run, the amount of budesonide remaining in the reservoir of the nebulizer was determined. The SAE-CD to corticosteroid molar ratios used were 10:1, 14:1, and 20:1. The data indicate that increasing the molar ratio resulted in an increase of the amount of budesonide delivered and a decrease in the amount of budesonide remaining in the reservoir.

Changes in the molar ratio of SAE-CD to corticosteroid can also have an impact upon the dissolution rate of corticosteroid in an aqueous medium. A study was conducted on a roller mixer having containers with solutions containing varying amounts of SAE-CD, e.g. CAPTISOL, and a fixed amount of fluticasone propionate or mometasone furoate. The samples were prepared by mixing the corticosteroid with a solution containing the SAE-CD in a vortexer for about 30 seconds and then placing the containers on the roller mixer. Aliquots were taken periodically from each container and the amount of dissolved corticosteroid was determined. The SAE-CD to corticosteroid molar ratios used were 10:1, 14:1, and 20:1. The data indicate that increasing the molar ratio resulted in an increase in the rate of dissolution of the corticosteroid.

The corticosteroid compound is present in the final, diluted corticosteroid composition designed for inhalation in an amount from about 1 μg/ml to about 10 mg/ml, about 10 μg/ml to about 1 mg/ml, or about 20 μg/ml to about 500 μg/ml. For example, the drug concentration can be between about 30 and 1000 μg/ml for triamcinolone acetonide, and between about 50 and 2000 μg/ml for budesonide, depending on the volume to be administered. By following the preferred methods of the present invention, relatively high concentrations of the corticosteroid can be achieved in an aqueous-based composition.

Similarly, the corticosteroid compound is present in the final, diluted corticosteroid composition designed for nasal administration in an amount from about 10 μg/ml to 6 mg/ml, 50 μg/ml to about 10 mg/ml, about 100 μg/ml to about 2 mg/ml, or about 300 μg/ml to 1 mg/ml. For example, the drug concentration can be between about 250 μg/ml and 1 mg/ml or 250 μg/ml and 6 mg/ml for triamcinolone acetonide, and between about 400 μg/ml and 1.6 mg/ml or 250 μg/ml and 6 mg/ml for budesonide, depending on the volume to be administered.

For the treatment of pulmonary disorders and sinus-related disorders, the diluted corticosteroid composition is prepared as described herein. The corticosteroid for such treatment is preferably, beclomethasone dipropionate, beclomethasone monopropionate, betamethasone, budesonide, ciclesonide, desisobutyryl-ciclesonide, flunisolide, fluticasone, fluticasone propionate, fluticasone furoate, mometasone, mometasone furoate, or triamcinolone acetonide, and is formulated in the concentrations set forth herein. The daily dose of the corticosteroid is generally about 0.05 to 10 mg, depending on the drug and the disease, in accordance with the *Physician's Desk Reference* (PDR). However, in view of the improved bioavailability of a corticosteroid when administered as a solution of the invention, the dose required to achieve a desired clinical endpoint, clinical benefit or therapeutic benefit may be lower than the corresponding dose indicated in the PDR.

A unit dose of budesonide may also be administered once daily, once every two days, once every week, once every month, or even less frequently as set forth in U.S. Pat. No. 6,598,603 and No. 6,899,099, wherein a dose comprises 0.05 to 2.0 mg or 0.25 to 1.0 mg of budesonide. Administration can be during the daytime and/or nighttime. A dose of budesonide, or corticosteroid, can be administered twice, thrice or more times per day or on an as-needed basis.

in some embodiments, a dose comprises 1 μg to 20 mg, 0.01 mg to 10 mg, 0.025 mg to 10 mg, 0.05 mg to 5 mg, 0.1 mg to 5 mg, 0.125 mg to 5 mg, 0.25 mg to 5 mg, 0.5 mg to 5 mg, 0.05 mg to 2 mg, 0.1 mg to 2 mg, 0.125 mg to 2 mg, 0.25 mg to 2 mg, 0.5 mg to 2 mg, 1 μg, 10 μg, 25 μg, 50 μg, 100 μg, 125 μg, 200 μg, 250 μg, 25 to 66 μg, 48 to 81 μg, 73 to 125 μg, 40 μg, 64 μg, 95 μg, 35 to 95 μg, 25 to 125 μg, 60 to 170 μg, 110 μg, 170 μg, 45 to 220 μg, 45 to 85 μg, 48 to 82 μg, 85 to 160 μg, 140 to 220 μg, 120 to 325 μg, 205 μg, 320 μg, 325 μg, 90 to 400 μg, 95 to 170 μg, 165 to 275 μg, or 275 to 400 μg of budesonide, said dose being a nominal dose, nominal available dose, emitted dose, delivered dose, dose to subject, or dose to lung.

The corticosteroid can be present in its neutral, ionic, salt, basic, acidic, natural, synthetic, diastereomeric, isomeric, isomeric, enantiomerically pure, racemic, solvate, anhydrous, hydrate, chelate, derivative, analog, esterified, non-esterfied, or other common form. Whenever an active agent is named herein, all such forms available are included. For example, all known forms of budesonide are considered within the scope of the invention.

The formulation of the invention can be used to deliver two or more different active agents (active ingredients, therapeutic agents, etc.). Particular combinations of active agents can be provided by the present formulation. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity. Exemplary combinations of active agents are described herein.

A corticosteroid, such as budesonide, can be administered in combination with one or more other drugs (active ingredients, therapeutic agents, active agents, etc., the terms being used interchangeably herein unless otherwise specified). Such other drugs include: $B_2$ adrenoreceptor agonist, topical anesthetic, $D_2$ receptor agonist, anticholinergic agent.

$B_2$-Adrenoreceptor agonists for use in combination with the compositions provided herein include, but are not limited to, Albuterol (alpha$^1$-(((1,1-dimethylethyl)amino) methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyeamino)-1-hydroxyethyl)-1,2-phenyleneester); Broxaterol (3-bromo-alpha-(((1,1-dimethylethyl)amino)methyl)-5-isoxazolemethanol); Isoproterenol (4-(1-hydroxy-2-((1-methylethyl-)amino) ethyl)-1,2-benzene-diol); Trimetoquinol (1,2,3,4-tetrahydro-1-((3,4-,5-trimethoxyphenyl)-methyl)-6,7-isoquinolinediol); Clenbuterol (4-amino-3,5-dichloro-alpha-(((1,1-diemthylethyl)amino)methyl)benzenemethanol); Fenoterol (5-(1-hydroxy-2-((2-(4-hydroxyphenyl)-1-methylethyl) amino)ethyl)-1,3-benzenediol); Formoterol (2-hydroxy-5-((1RS)-1-hydroxy-2-(((1RS)-2-(p-methoxyphenyl)-1-methylethyl)amino)ethyl)formanilide); (R,R)-Formoterol; Desformoterol ((R,R) or (S,S)-3-amino-4-hydroxy-alpha-(((2-(4-methoxyphenyl)-1-methyl-ethyl)amino)methyl)benzenemethanol); Hexoprenaline (4,4'-(1,6-hexane-diyl)-bis (imino(1-hydroxy-2,1-ethanediyl)))bis-1,2-benzenediol); Isoetharine (4-(1-hydroxy-2((1-methylethyl)-amino)butyl)-1,2-benzenediol); Isoprenaline (4-(1-hydroxy-2-((1-methylethyl)amino)ethyl)-1,2-benzenediol); Meta-proterenol (5-(1-hydroxy-2((1-methylethyl)amino)ethyl)-1,3-benzenediol); Picumeterol (4-amino-3,5-dichloro-alpha-(((6-(2-(2-pyridinyl)ethoxy)hexyl)-amino)methyl)benzenemethanol); Pirbuterol (.alpha.$^6$-(((1,1-dimethylethyl)-amino)methyl)-3-hydroxy-2,6-pyridinemethanol); Procaterol (((R*,S*)-(.+-.)-8-hydroxy-5-(1-hydroxy-2-((1-methylethyl)amino)butyl)-2(1H)-quinolin-one); Reproterol ((7-(3-((2-(3,5-dihydroxyphenyl)-2-hydroxyethyl)amino)-propyl)-3,7-dihydro-1,3-dimethyl-1H-purine-2,6-dione); Rimiterol (4-(hydroxy-2-piperidinylmethyl)-1,2-benzenediol); Salbutamol ((.+-.)-alpha$^1$-(((1,1-dimethylethyl)amino) methyl)-4-hydroxy-1,3-b-enzenedimethanol); (R)-Salbutamol; Salmeterol ((.+-.)-4-hydroxy-.alpha$^1$-(((6-(4-phenylbutoxy)hexyl)-amino)methyl)-1,3-benzenedimethanol); (R)-Salmeterol; Terbutaline (5424(1,1-dimethylethyl) amino)-1-hydroxyethyl)-1,3-benzenediol); Tulobuterol (2-chloro-.alpha.-(((1,1-dimethylethyl)amino)methyl)benzenemethanol); and TA-2005 (8-hydroxy-5((1R)-1-hydroxy-2-(N-((1R)-2-(4-methoxyphenyl)-1-methylethyl) amino)ethyl)carbostyril hydrochloride).

Dopamine ($D_2$) receptor agonists include, but are not limited to, Apomorphine ((r)-5,6,6a,7-tetrahydro-6-methyl-4H-dibenzo[de,glquinoline-10,11-diol); Bromocriptine ((5', alpha.)-2-bromo-12'-hydroxy-2'-(1-methylethyl)-5'-(2-methylpropyl)ergotaman-3',6'', 18-trione); Cabergoline ((8.beta.)-N-(3-(dimethylamino)propyl)-N-((ethylamino) carbony-1)-6-(2-propenyl)ergoline-8-carboxamide); Lisuride (N'-((8-alpha-)-9,10-didehydro-6-methylergolin-8-yl)-N,N-diethylurea); Pergolide ((8-beta-)-8-((methylthio) methyl)-6-propylergoline); Levodopa (3-hydroxy-L-tryrosine); Pramipexole ((s)-4,5,6,7-tetrahydro-N$^6$-prop-yl-2,6-benzothiazolediamine); Quinpirole hydrochloride (trans-(−)-4aR-4,4a,5,6,7,8,8a,9-octahydro-5-propyl-1H-pyrazolo[3,4-g]quinoline hydrochloride); Ropinirole (4-(2,-(dipropylamino)ethyl)-1,3-dihydro-2H-indol-2-one); and Talipexole (5,6,7,8-tetrahydro-6-(2-propenyl)-4H-thia-zolo [4,5-d]azepin-2-amine). Other dopamine $D_2$ receptor agonists for use herein are disclosed in International Patent Application Publication No, WO 99/36095, the relevant disclosure of which is hereby incorporated by reference.

Anticholinergic agents for use herein include, but are not limited to, ipratropium bromide, oxitropium bromide, atropine methyl nitrate, atropine sulfate, ipratropium, belladonna extract, scopolamine, scopolamine methobromide, homatropine methobromide, hyoscyamine, isopriopramide, orphenadrine, benzalkonium chloride, tiotropium bromide and glycopyrronium bromide, in certain embodiments, the compositions contain an anticholinergic agent, such as ipratropium bromide or tiotropium bromide, at a concentration of about 5 µg/mL to about 5 mg/mL, or about 50 µg/mL to about 200 µg/mL. In other embodiments, the compositions for use in the methods herein contain an anticholinergic agent, including ipratropium bromide and tiotropium bromide, at a concentration of about 83 µg/mL or about 167 µg/mL.

Other active ingredients for use herein in combination therapy, include, but are not limited to, IL-5 inhibitors such as those disclosed in U.S. Pat. No. 5,668,110, No. 5,683,983, No. 5,677,280, No. 6,071,910 and No. 5,654,276, the relevant disclosures of which are hereby incorporated by reference; antisense modulators of IL-5 such as those disclosed in U.S. Pat. No. 6,136,603, the relevant disclosure of which is hereby incorporated by reference; milrinone (1,6-dihydro-2-methyl-6-oxo-[3,4'-bipyridine]-5-carbonitrile); milrinone lactate; tryptase inhibitors such as those disclosed in U.S. Pat. No. 5,525,623, the relevant disclosure of which is hereby incorporated by reference; tachykinin receptor antagonists such as those disclosed in U.S. Pat. No. 5,691, 336, U.S. Pat. No. 5,877,191, U.S. Pat. No. 5,929,094, No. 5,750,549 and No. 5,780,467, the relevant disclosures of which are hereby incorporated by reference; leukotriene receptor antagonists such as montelukast sodium (Singular™, R-(E)]-1-[[[1-[3-[2-(7-chloro-2-quinolinyl)ethenyl-] phenyl]-3-[2-(1-hydroxy-1-methylethyl)phenyl]-propyl] thio]methyl]cyclopro-paneacetic acid, monosodium salt), 5-lypoxygenase inhibitors such as zileuton (Zyflo™, Abbott Laboratories, Abbott Park, Ill.), and anti-IgE antibodies such as Xolair™ (recombinant humanized anti-IgE monoclonal antibody (CGP 51901; IGE 025A; rhuMAb-E25), Genentech, Inc., South San Francisco, Calif.), and topical anesthetics such as lidocaine, N-arylamide, aminoalkylbenzoate, prilocalne, etidocaine (U.S. Pat. No. 5,510,339, U.S. Pat. No. 5,631,267, and U.S. Pat. No. 5,837,713, the relevant disclosures of which are hereby incorporated by reference).

Exemplary combination formulations of the invention comprise the following components.

| FORM. | Corticosteroid (A) | Other Active Ingredient (B) |
|---|---|---|
| I | Budesonide | Formoterol |
| II | Budesonide | Salmeterol |
| III | Budesonide | Albuterol |
| IV | Fluticasone propionate | Salmeterol |

A formulation comprising a corticosteroid and another active ingredient can be prepared according to the examples below. In one embodiment, the SAE-CD is present in an amount sufficient to solubilize the corticosteroid and the other active ingredient. In another embodiment, the SAE-CD is present in an amount sufficient to solubilize the corticosteroid or the other active ingredient.

Depending upon the other active ingredient used, it may or may not bind competitively against the corticosteroid with the SAE-CD. In some embodiments, the SAE-CD has a higher equilibrium binding constant for the other active ingredient than it has for the corticosteroid. In some embodiments, the SAE-CD has a higher equilibrium binding constant for the corticosteroid than it has for the other active ingredient. In some embodiments, the SAE-CD has approximately the same equilibrium binding constant for the other active ingredient as it has for the corticosteroid. Alternatively, the other active ingredient does not bind with the SAE-CD even though the corticosteroid does. Accordingly, the invention provides embodiments wherein, the SAE-CD solubilizes the corticosteroid, the other active ingredient, or a combination thereof. The invention also provides embodiments wherein, the SAE-CD solubilizes at least a major portion of the corticosteroid, the other active ingredient, or of each. The invention also provides embodiments wherein, the SAE-CD does not solubilize the other active ingredient.

The molar ratio of SAE-CD to corticosteroid and SAE-CD to other active ingredient can vary as needed to provide a combination formulation as described herein. The SAE-CD is generally present in molar excess over the corticosteroid, the other active ingredient, or both.

The phase solubility binding curve for Salmeterol xinafoate and budesonide was determined as described herein, and the approximate equilibrium binding constant (Ki) of each with CAPTISOL was determined. The approximate Ki for Salmeterol xinafoate was approximately 3,500, and the approximate Ki for budesonide was 600 under the test conditions used. The molar ratio of CAPTISOL to Salmeterol xinafoate at saturated solubility was about 3.2 under the test conditions used. Their may be a reduction in the amount of budesonide solubilized by CAPTISOL in the presence of Salmeterol xinafoate; however, clear aqueous liquid solution formulations comprising therapeutically effective amounts of budesonide and Salmeterol xinafoate were prepared.

A formulation comprising budesonide, albuterol and SAE-CD was prepared according to Example 25. The formulation was clear after preparation. The combination of budesonide and albuterol has been shown to be physically and chemically stable and would be expected to provide the same improved aerosol performance and AUC per µg budesonide dosed as the solution of budesonide alone. Furthermore, the patient would benefit from the simultaneous administration of the two drugs.

The invention includes methods for the treatment, prevention, or amelioration of one or more symptoms of a corticosteroid-responsive disorder, a disease or disorder of the air passageways e.g. respiratory or pulmonary disorders such as bronchoconstrictive disorders; sinus disorders such as sinusitis. The method further includes administering one or more of (a), (b), (c) or (d) as follows: (a) a $b_2$-adrenoreceptor agonist; (b) a dopamine ($D_2$) receptor agonist; (c) a prophylactic therapeutic, such as a steroid; or (d) an anticholinergic agent; simultaneously with, prior to or subsequent to the composition provided herein.

Embodiments of the present invention allow for combinations to be prepared in a variety of ways:

1) Mixing ready to use solutions of a β2-agonist such as levalbuterol or anticholinergic such as ipatropium bromide with a ready to use solution of a corticosteroid in SAE-CD;

2) Mixing ready to use solutions of a β2-agonist or anticholinergic with a concentrated solution of a corticosteroid dissolved using SAE-CD;

3) Mixing a ready to use solution of a β2-agonist or anticholinergic with substantially dry SAE-CD and a substantially dry corticosteroid;

4) Mixing a ready to use solution of a β2-agonist or anticholinergic with a substantially dry mixture of SAE-CD and a corticosteroid or more conveniently a pre-measured amount of the mixture in a unit container such as a capsule (empty a capsule into ready to use solution);

5) Mixing a ready to use solution of a corticosteroid such as budesonide with a substantially dry long acting or short acting β2-agonist and/or with a substantially dry anticholinergic such as ipatropium bromide or tiotropium bromide; or 6) Dissolving a substantially dry β2-agonist, and/or a substantially dry anticholinergic and a substantially dry SAE-CD plus a substantially dry corticosteroid.

The materials used herein can be used in micronized or non-micronized form and crystalline, polymorphic or amorphous form. This is particularly true of the corticosteroids and other active ingredients.

It is well understood by those of ordinary skill in the art that the above solutions or powders may optionally contain other ingredients such as buffers and/or tonicity adjusters and/or antimicrobials and/or additives or other such excipients as set forth herein or as presently used in inhalable liquid formulations to improve the output of the nebulizer.

Dosing, use and administration of the therapeutic agents disclosed herein is generally intended to follow the guidelines set forth in the Physician's Desk Reference, $55^{th}$ Edition (Thompson Healthcare, Montvale, N.J., 2005) the relevant disclosure of which is hereby incorporated by reference.

The bronchoconstrictive disorder to be treated, prevented, or whose one or more symptoms are to be ameliorated is associated with asthma, including, but not limited to, bronchial asthma, allergic asthma and intrinsic asthma, e.g., late asthma and airway hyper-responsiveness; and, particularly in embodiments where an anticholinergic agent is used, other chronic obstructive pulmonary diseases (COPDs), including, but not limited to, chronic bronchitis, emphysema, and associated cor pulmonale (heart disease secondary to disease of the lungs and respiratory system) with pulmonary hypertension, right ventricular hypertrophy and right heart failure. COPD is frequently associated with cigarette smoking, infections, environmental pollution and occupational dust exposure.

A formulation according to the invention will generally have a storage shelf life of no less than 6 months. In this case, shelf life is determined only as regards the increase in the amount of corticosteroid degradation by-products or a reduction in the amount of corticosteroid remaining in the formulation. For example, for a formulation having a shelf life of at least six months, the formulation will not demonstrate an unacceptable and substantial increase in the amount of degradants during the storage period of at least six months. The criteria for acceptable shelf-life are set as needed according to a given product and its storage stability requirements. In other words, the amount of degradants in a formulation having an acceptable shelf-life will not increase beyond a predetermined value during the intended period of storage. On the other hand, the amount of degradants of a formulation having an unacceptable shelf-life will increase beyond the predetermined value during the intended period of storage.

The method of Example 3 was followed to determine the stability of budesonide in solution. The shelf-life was defined as the time to loss of 10% potency. Under the conditions tested, the loss of potency was first order. The shelf life of a Captisol-Enabled® Budesonide Inhalation Solution (a solution comprising budesonide and SBE7-β-CD) is greater than about 3 years at a pH between 4 and 5, i.e. about 90 months at pH 4.0 and about 108 months at pH 5.0 without the need to add any other stabilizers, such as EDTA, in water in the presence of about 5% wt./vol. SAE-CD. This shelf-life is greater than that reported by Otterbeck (U.S. Pat. No. 5,914,122; up to six weeks at pH 4.0-6.0 in water in the presence of EDTA, HP-β-CD and other additives.)

Figure 11:
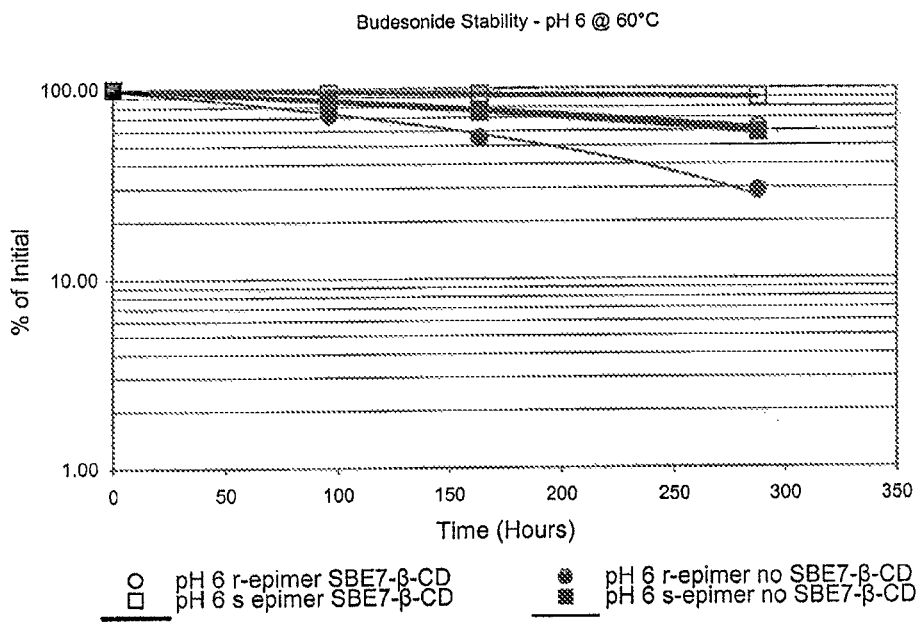

The inventors have also discovered that SAE-CD is capable of stabilizing the isomers of budesonide to different extents. A study to determine if SBE7-β-CD stabilized budesonide solutions and if it preferentially stabilized one isomer was conducted according to Example 13. FIG. 11 is a semi-log plot of the % of initial concentration at each time point for the samples stored at 60° C. Loss of budesonide was first order at each temperature. The table below shows the pseudo-first order rate constants calculated for each isomer at 60° C. and 80° C.

| Pseudo $1^{st}$ Order Rate constant (hours$^{-1}$) Temperature 60° C. | | | | |
|---|---|---|---|---|
| Ph | Rate constant R-isomer | With/without CAPTISOL ratio for R-isomers | Rate constant S-isomer | With/without CAPTISOL ratio for S-isomers | R/S rate constant ratio |
| 4 w/ CAPTISOL | 0.000597 | 0.547 | 0.00012 | 0.323 | 5.06 |
| 4 no CAPTISOL | 0.00109 | | 0.0037 | | 2.99 |
| 6 w/ CAPTISOL | 0.001661 | 0.385 | 0.000361 | 0.193 | 4.60 |
| 6 no CAPTISOL | 0.00432 | | 0.001872 | | 2.31 |

| Pseudo $1^{st}$ Order Rate constant (hours$^{-1}$) Temperature 80° C. | | | | |
|---|---|---|---|---|
| pH | Rate Constant R-isomer | With/without CAPTISOL ratio for R-isomers | Rate constant S-isomer | With/without CAPTISOL ratio for S-isomers | R/S rate constant ratio |
| 4 w/ CAPTISOL | 0.002250 | 0.607 | 0.000644 | 0.491 | 3.49 |
| 4 no CAPTISOL | 0.003704 | | 0.00131 | | 2.83 |
| 6 w/ CAPTISOL | 0.00732 | 0.529 | 0.00254 | 0.384 | 2.88 |
| 6 no CAPTISOL | 0.0138 | | 0.00661 | | 2.09 |

SBE7-β-CD stabilized both R- and S-isomers of budesonide in solutions at both pH 4 and 6. The with/without CAPTISOL ratio of rate constants was much less than 1 at all temperatures. SBE7-β-CD had a greater effect on the stability of both the R and S-isomer at pH 6 than at pH 4. At a given temperature the ratio of rate constants with/without SBE7-β-CD was less at pH 6 than at pH 4. Although SBE7-β-CD stabilized both isomers, the S-isomer appears to be stabilized to an even greater extent than the R. At all temperatures and pHs tested, the ratio of rate constants with/without SBE7-ß-CD was lower for the S isomer. The degree of stabilization affected by SBE7-P-CD at 60° C. is greater than at 80° C. An even greater degree of stabilization would be expected at 40° C. and/or room temperature (20-30 C).

Figure 12:
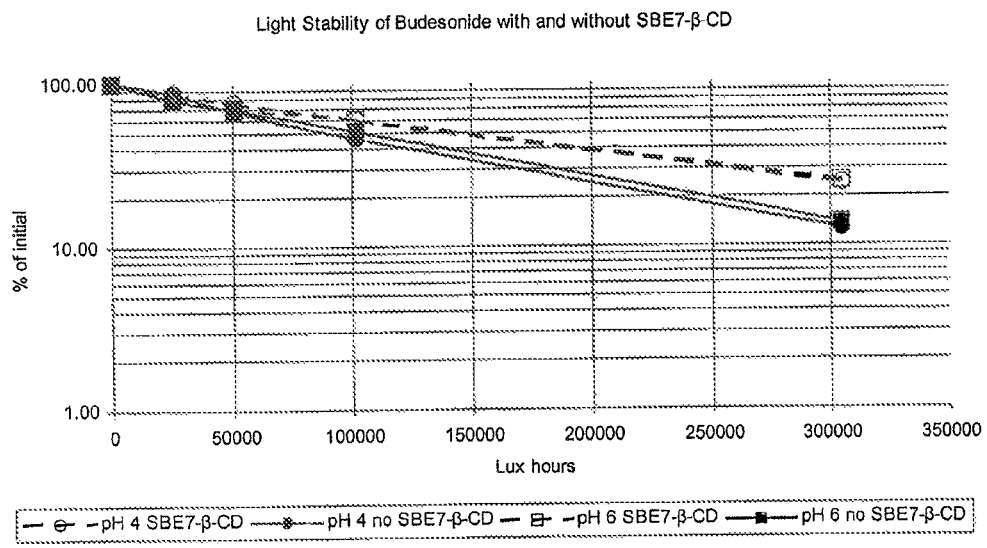

Samples of the above solutions were also placed in a chamber under a bank of fluorescent lights. Vials were periodically removed and assayed for budesonide. FIG. 12 shows the semi-log plot of the % of initial value remaining as a function of light exposure (light intensity*time). As noted in the table below, SBE7-β-CD significantly reduced the photodecomposition of budesonide. The loss of budesonide was first order and independent of pH.

| Light Stability of Budesonide Pseudo 1st Order Rate constant (hour$^{-1}$) | | |
|---|---|---|
| | pH 4 | pH 6 |
| Captisol | 0.0585 | 0.0562 |
| No Captisol | 0.0812 | 0.0822 |

The formulation of the invention can be provided as a kit adapted to form an inhalable solution for nebulization. The kit can comprise a corticosteroid, SAE-CD, an aqueous carrier, and optionally one or more other components. The corticosteroid and SAE-CD can be provided together or separately in solid, suspended or dissolved form. After mixing SAE-CD with corticosteroid in the presence of an aqueous carrier, the solids will dissolve to form an inhalable solution rather than suspension for nebulization. Each component can be provided in an individual container or together with another component. For example, SAE-CD can be provided in an aqueous solution while budesonide is provided in dry solid form or wet suspended form. Alternatively, SAE-CD is provided in dry form and budesonide is provided as an aqueous suspension, e.g., PULMICORT RESPULES™. The kit can instead comprise an admixture of a solid derivatized cyclodextrin and solid cortico steroid and, optionally, at least one solid pharmaceutical excipient, such that a major portion of the active agent is not complexed with the derivatized cyclodextrin prior to reconstitution of the admixture with an aqueous carrier. Alternatively, the composition can comprise a solid mixture comprising the inclusion complex of a derivatized cyclodextrin and an active agent, wherein a major portion of the active agent is complexed with the derivatized cyclodextrin prior to reconstitution of the solid mixture with an aqueous carrier. Depending upon the storage temperature of the kit, the aqueous carrier may be a liquid or frozen solid. In one embodiment, the kit excludes the aqueous carrier during storage, but the aqueous carrier is added to the SAE-CD and corticosteroid prior to use to form the nebulization solution. The corticosteroid and SAE-CD can be complexed and present in aqueous concentrated form prior to addition of the aqueous carrier, which is later added to bring the solution to volume and proper viscosity and concentration for nebulization. A reconstitutable formulation can be prepared according to any of the following processes. A liquid formulation of the invention is first prepared, then a solid is formed by lyophilization (freeze-drying), spray-drying, spray freeze-drying, antisolvent precipitation, various processes utilizing supercritical or near supercritical fluids, or other methods known to those of ordinary skill in the art to make a solid for reconstitution. Example 29 details a method for the preparation of a lyophilized solid composition comprising corticosteroid and SAE-CD by lyophilization of a liquid composition or formulation of the invention. The lyophilized solid can be dissolved in an aqueous liquid carrier prior to administration via nebulization. The dried powder would provide a stable form for long-term storage and would also be useful to rapidly prepare inhalation compositions on a larger scale, or as an additive to another inhalation solution medication to prepare combination products.

While the liquid composition or formulation of the invention can be administered to the lung, it would also be suitable for nasal, oral, ophthalmic, otic or topical administration. The liquid composition or formulation may also be administered via inhalation using a device such as a pump spray, metered dose inhaler, or pressurized metered dose inhaler. Accordingly, the invention provides a method of treating a corticosteroid-responsive disease or disorder by administration of the liquid to a subject in need of such treatment.

A liquid vehicle (carrier) included in a formulation of the invention comprises an aqueous liquid carrier, such as water, aqueous alcohol, propylene glycol, or aqueous organic solvent. Example 30 details the preparation of a liquid formulation comprising 20% w/v SAE-CD, corticosteroid, water and ethanol (0-5%). Increasing the concentration of the ethanol in the liquid resulted in a decrease in the maximum saturated solubility of the corticosteroid.

Although not necessary, the formulation of the present invention may include a conventional preservative, antioxidant, buffering agent, acidifying agent, alkalizing agent, colorant, solubility-enhancing agent, complexation-enhancing agent, electrolyte, glucose, stabilizer, tonicity modifier, bulking agent, antifoaming agent, oil, emulsifying agent, cryoprotectant, plasticizer, flavors, sweeteners, a tonicity modifier, surface tension modifier, viscosity modifier, density modifier, volatility modifier, other excipients known by those of ordinary skill in the art for use in preserved formulations, or a combination thereof.

As used herein, the term "alkalizing agent" is intended to mean a compound used to provide alkaline medium, such as for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

Inclusion of a conventional preservative in the inhalable solution formulation is optional, since the formulation is self-preserved by SAE-CD depending upon its concentration in solution. Nonetheless, a conventional preservative can be further included in the formulation if desired. Preservatives can be used to inhibit microbial growth in the compositions. The amount of preservative is generally that which is necessary to prevent microbial growth in the composition for a storage period of at least six months. As used herein, a conventional preservative is a compound used to at least reduce the rate at which bioburden increases, but preferably maintains bioburden steady or reduces bioburden after contamination has occurred. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl or butyl parabens and others known to those of ordinary skill in the art.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, EDTA, pentetate, and sodium metabisulfite and others known to those of ordinary skill in the art.

As used herein, the term "buffering agent" is intended to mean a compound used to resist change in pH upon dilution or addition of acid or alkali. Buffers are used in the present compositions to adjust the pH to a range of between about 2 and about 8, about 3 to about 7, or about 4 to about 5. Such compounds include, by way of example and without limitation, acetic acid, sodium acetate, adipic acid, benzoic acid, sodium benzoate, boric acid, sodium borate, citric acid, glycine, maleic acid, monobasic sodium phosphate, dibasic sodium phosphate, HEPES, lactic acid, tartaric acid, potassium metaphosphate, potassium phosphate, monobasic sodium acetate, sodium bicarbonate, tris, sodium tartrate and sodium citrate anhydrous and dihydrate and others known to those of ordinary skill in the art. Other buffers include citric acid/phosphate mixture, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)imino-tris(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)-butanesulfonic acid), TAPSO (3-(N-tris(hydroxymethyl)methylamino)-2-hydroxypropanesulfonic acid), TRIZMA™ (tris(hydroxymethylaminomethane), HEPPSO (N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS (N-(2-hydroxyethyl)piperazine-N'-(3-propanesulfonic acid), TRICINE (N-tris(hydroxymethyl)methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS(N-tris(hydroxymethyl)methyl-3-aminopropanesulfonic acid), AMPD (2-amino-2-methyl-1,3-propanediol), and/or any other buffers known to those of skill in the art.

A complexation-enhancing agent can be added to a formulation of the invention. When such an agent is present, the ratio of cyclodextrin/active agent can be changed. A complexation-enhancing agent is a compound, or compounds, that enhance(s) the complexation of the active agent with the cyclodextrin. Suitable complexation enhancing agents include one or more pharmacologically inert water soluble polymers, hydroxy acids, and other organic compounds typically used in liquid formulations to enhance the complexation of a particular agent with cyclodextrins.

Hydrophilic polymers can be used as complexation-enhancing, solubility-enhancing and/or water activity reducing agents to improve the performance of formulations containing a cyclodextrin. Loftsson has disclosed a number of polymers suitable for combined use with a cyclodextrin (underivatized or derivatized) to enhance the performance and/or properties of the cyclodextrin. Suitable polymers are disclosed in *Pharmazie* (2001), 56(9), 746-747; *International Journal of Pharmaceutics* (2001), 212(1), 29-40; Cyclodextrin: From Basic Research to Market, International Cyclodextrin Symposium, 10th, Ann Arbor, Mich., United States, May 21-24, 2000 (2000), 10-15 (Wacker Biochem Corp.; Adrian, Mich.); PCT International Publication No. WO 9942111; *Pharmazie*, 53(11), 733-740 (1998); *Pharm. Technol. Eur.*, 9(5), 26-34 (1997); *J. Pharm. Sci.* 85(10), 1017-1025 (1996); European Patent Application EP0579435; Proceedings of the International Symposium on Cyclodextrins, 9th, Santiago de Comostela, Spain, May 31-Jun. 3, 1998 (1999), 261-264 (Editor(s): Labandeira, J. J. Torres; Vila-Jato, J. L. Kluwer Academic Publishers, Dordrecht, Neth); *S.T.P. Pharma Sciences* (1999), 9(3), 237-242; ACS Symposium Series (1999), 737(Polysaccharide Applications), 24-45; *Pharmaceutical Research* (1998), 15(11), 1696-1701; *Drug Development and Industrial Pharmacy* (1998), 24(4), 365-370; *International Journal of Pharmaceutics* (1998), 163(1-2), 115-121; Book of Abstracts, 216th ACS National Meeting, Boston, Aug. 23-27 (1998), CELL-016, American Chemical Society; *Journal of Controlled Release*, (1997), 44/1 (95-99); *Pharm. Res.* (1997) 14(11), S203; *Investigative Ophthalmology & Visual Science*, (1996), 37(6), 1199-1203; Proceedings of the International Symposium on Controlled Release of Bioactive Materials (1996), 23rd, 453-454; *Drug Development and Industrial Pharmacy* (1996), 22(5), 401-405; Proceedings of the International Symposium on Cyclodextrins, 8th, Budapest, Mar. 31-Apr. 2, (1996), 373-376. (Editor(s): Szejtli, I.; Szente, L. Kluwer: Dordrecht, Neth.); *Pharmaceutical Sciences* (1996), 2(6), 277-279; *European Journal of Pharmaceutical Sciences*, (1996) 4(SUPPL.), S144; Third European Congress of Pharmaceutical Sciences Edinburgh, Scotland, UK Sep. 15-17, 1996; *Pharmazie*, (1996), 51(1), 39-42; *Eur. J. Pharm. Sci.* (1996), 4(Suppl.), S143; U.S. Pat. No. 5,472,954 and U.S. Pat. No. 5,324,718; *International Journal of Pharmaceutics* (Netherlands), (Dec. 29, 1995) 126, 73-78; Abstracts of Papers of the American Chemical Society, (2 Apr. 1995) 209(1), 33-CELL; *European Journal of Pharmaceutical Sciences*, (1994) 2, 297-301; *Pharmaceutical Research* (New York), (1994) 11(10), S225; *International Journal of Pharmaceutics* (Netherlands), (Apr. 11, 1994) 104, 181-184; and *International Journal of Pharmaceutics* (1994), 110(2), 169-77, the entire disclosures of which are hereby incorporated by reference.

Other suitable polymers are well-known excipients commonly used in the field of pharmaceutical formulations and are included in, for example, *Remington's Pharmaceutical Sciences*, 18th Edition, Alfonso R. Gennaro (editor), Mack Publishing Company, Easton, Pa., 1990, pp. 291-294; Alfred Martin, James Swarbrick and Arthur Commarata, *Physical Pharmacy*. Physical Chemical Principles in Pharmaceutical Sciences, 3rd edition (Lea & Febinger, Philadelphia, Pa., 1983, pp. 592-638); A. T. Florence and D. Altwood, (*Physicochemical Principles of Pharmacy*, 2nd Edition, MacMillan Press, London, 1988, pp. 281-334. The entire disclosures of the references cited herein are hereby incorporated by references. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

An emulsifying agent is intended to mean a compound that aids the formation of an emulsion. An emulsifier can be used to wet the corticosteroid and make it more amenable to dissolution. Emulsifiers for use herein include, but are not limited to, polyoxyetheylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2-lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract.

As used herein, the term "stabilizer" is intended to mean a compound used to stabilize the therapeutic agent against physical, chemical, or biochemical process that would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those of ordinary skill in the art. Other tonicity modifiers include both inorganic and organic tonicity adjusting agents. Tonicity modifiers include, but are not limited to, ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, proplyene glycol, silver nitrate, sodium acetate, sodium bicarbonate, sodium biphosphate, sodium bisulfate, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine and zinc sulfate. In one embodiment, the tonicity of the liquid formulation approximates the tonicity of the tissues in the respiratory tract.

An osmotic agent can be used in the compositions to enhance the overall comfort to the patient upon delivery of the corticosteroid composition. Osmotic agents can be added to adjust the tonicity of SAE-CD containing solutions. Osmolality is related to concentration of SAE-CD in water. At SBE7-β-CD concentrations below about 11-13% w/v, the solutions are hypotonic or hypoosmotic with respect to blood and at SBE7-β-CD concentrations above about 11-13% w/v the SBE7-β-CD containing solutions are hypertonic or hyperosmotic with respect to blood. When red blood cells are exposed to solutions that are hypo- or hypertonic, they can shrink or swell in size, which can lead to hemolysis. As noted above and in FIG. 1, SBE-CD is less prone to induce hemolysis than other derivatized cyclodextrins. Suitable osmotic agents include any low molecular weight water-soluble species pharmaceutically approved for pulmonary and nasal delivery such as sodium chloride, lactose and glucose. The formulation of the invention can also include biological salt(s), potassium chloride, or other electrolyte(s).

As used herein, the term "antifoaming agent" is intended to mean a compound or compounds that prevents or reduces the amount of foaming that forms on the surface of the liquid formulation. Suitable antifoaming agents include dimethicone, simethicone, octoxynol, ethanol and others known to those of ordinary skill in the art.

As used herein, the term "bulking agent" is intended to mean a compound used to add bulk to the lyophilized product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

As used herein, the term "cryoprotectant" is intended to mean a compound used to protect an active therapeutic agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

A solubility-enhancing agent or solubility enhancer can be added to the formulation of the invention. A solubility-enhancing agent is a compound, or compounds, that enhance(s) the solubility of the corticosteroid when in an aqueous liquid carrier. When another solubility enhancing agent is present, the ratio of SAE-CD to corticosteroid can be changed, thereby reducing the amount of SAE-CD required to dissolve the corticosteroid. Suitable solubility enhancing agents include one or more cyclodextrins, cyclodextrin derivatives, SAE-CD, organic solvents, detergents, soaps, surfactant and other organic compounds typically used in parenteral formulations to enhance the solubility of a particular agent. Exemplary solubility enhancers are disclosed in U.S. Pat. No. 6,451,339; however, other surfactants used in the pharmaceutical industry can be used in the formulation of the invention. Some suitable cyclodextrin include underivatized cyclodextrins and cyclodextrin derivatives, such as SAE-CD, SAE-CD derivatives, hydroxyalkyl ether cyclodextrin and derivatives, alkyl ether cyclodextrin and derivatives, sulfated cyclodextrin and derivatives, hydroxypropyl-β-cyclodextrin, 2-HP-β-CD, methyl-β-cyclodextrin, carboxyalkyl thioether derivatives, succinyl cyclodextrin and derivatives, and other cyclodextrin suitable for pharmaceutical use. SAE-CD cyclodextrins are particularly advantageous.

Suitable organic solvents that can be used in the formulation include, for example, ethanol, glycerin, poly(ethylene glycol), propylene glycol, poloxamer, aqueous forms thereof and others known to those of ordinary skill in the art.

It should be understood that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

An active agent contained within the present formulation can be present as its pharmaceutically acceptable salt. As used herein, "pharmaceutically acceptable salt" refers to derivatives of the disclosed compounds wherein the active agent is modified by reacting it with an acid or base as needed to form an ionically bound pair. Examples of pharmaceutically acceptable salts include conventional non-toxic salts or the quaternary ammonium salts of the parent compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. The pharmaceutically acceptable salts of the present invention can be synthesized from the parent active agent which contains a basic or acidic moiety by conventional chemical methods. Lists of other suitable salts are found in *Remington's Pharmaceutical Sciences*, 17$^{th}$, ed., Mack Publishing Company, Easton, Pa., 1985, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" are taken to mean warm blooded animals such as mammals, for example, cats, dogs, mice, guinea pigs, horses, bovine cows, sheep and humans.

A formulation of the invention will comprise an active agent present in an effective amount, effective dose or therapeutically effective dose. By the term "effective amount" or "effective dose" or "therapeutically effective dose", is meant the amount or quantity of active agent that is sufficient to elicit the required or desired response, or in other words, the amount that is sufficient to elicit an appreciable biological response when administered to a subject.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

Example 1

Exemplary formulations according to the invention were made according to the following general procedures.

Method A

Cyclodextrin is dissolved in water (or buffer) to form a solution containing a known concentration of cyclodextrin. This solution is mixed with an active agent in solid, suspension, gel, liquid, paste, powder or other form while mixing, optionally while heating to form an inhalable solution.

Method B

A known amount of substantially dry cyclodextrin is mixed with a known amount of substantially dry active agent. A liquid is added to the mixture to form a suspension, gel, solution, syrup or paste while mixing, optionally while heating and optionally in the presence of one or more other excipients, to form an inhalable solution.

Method C

A known amount of substantially dry cyclodextrin is added to a suspension, gel, solution, syrup or paste comprising a known amount of active agent while mixing, optionally while heating and optionally in the presence of one or more other excipients, to form an inhalable solution.

The methods of this example may be modified by the inclusion of a wetting agent in the composition in order to facilitate dissolution and subsequent inclusion complexation of the corticosteroid. A surfactant, soap, detergent or emulsifying agent can be used as a wetting agent.

Method D

To a solution comprising a known concentration or amount of SAE-CD, aqueous liquid carrier, and optionally one or more other excipients, is added a molar excess of the corticosteroid based upon the molar ratio of SAE-CD to corticosteroid at the point of saturated solubility of the corticosteroid, in the presence of the SAE-CD, as determined herein. For example, corticosteroid would be added at a 5%, 10%, 15%, 20%, 25%, 30% or greater molar excess. The components are mixed until equilibration, the point at which there is only a minor change in the concentration of budesonide over a one-hour period of time. Then, the excess corticosteroid is removed leaving behind the target solution of the invention.

The budesonide is added to the SAE-CD-containing solution as either a solid or suspension in an aqueous liquid carrier, which can be water, buffer, aqueous alcohol, aqueous organic solvent or a combination thereof. The alcohol and organic solvent are of a pharmaceutically acceptable grade, such as ethanol, propylene glycol, and others as described herein.

Method E

The SAE-CD and corticosteroid are triturated to form a mixture. Then, an aqueous liquid carrier is added to the mixture form the target solution of the invention.

The trituration can be conducted dry or in the presence of moisture, water, buffer, alcohol, surfactant, organic solvent, glycerin, poly(ethylene glycol), poloxamer, or a combination thereof.

Method F

Any of the methods herein are conducted in the presence of heat, e.g. at a temperature of least 40° C.

Method G

Any of the methods herein are conducted with cooling, e.g. at a temperature of less than 20° C. or less than 10° C. or less than 5° C.

Method H

Any of the methods herein are conducted in the presence of high shear mixing such as with a sonicator, narrow gauge syringe(s), mixer/homogenizer (POLYTRON from KINEMATICA, Europe; FLUKO, Shanghai, China; ULTIMAGRAL from GEA Niro, Inc., Columbia, Md.), rotor-stator mixer, or saw tooth mixer.

Method I

Any of the methods herein are conducted under reduced pressure.

Example 2

The MMD of nebulized solutions containing SBE7-β-CD and budesonide was determined as follows.

Placebo solutions of three different cyclodextrins were prepared at different concentrations. Two ml of the solutions were added to the cup of a Pari LC Plus nebulizer supplied with air from a Pari Proneb Ultra compressor. The particle size of the emitted droplets was determined using a Malvern Mastersizer S laser light scattering instrument.

Example 3

The stability of liquid formulations containing SAE-CD was determined by HPLC chromatography of aliquots periodically drawn from the liquid in storage.

Citrate-phosphate (McIlvaines) buffer solutions at a pH of 4, 5, 6, 7, or 8 were prepared by mixing various portions of 0.01M citric acid with 0.02 M $Na_2HPO_4$. These stock solutions contained 5% w/w Captisol. Approximately 250 μg/mL of budesonide was dissolved in each buffer solution. Aliquots of the solutions were stored at 40° C., 50° C. and 60° C. Control samples were stored at 5° C. but are not reported here. HPLC analysis of the samples was performed initially and after 1, 2, and 3 months storage.

The HPLC conditions included:

| | |
|---|---|
| Instrument: | PE Series 200 |
| Column: | Phenomenex Luna C18(2) 4.6 × 150 mm 3 um |
| Mobile Phase: | 58% Phosphate Buffer pH 3.4/39.5% ACN/2.5% MeOH |
| Mobile Phase Program: | 100% A (isocratic) |
| Wavelength | 240 |
| Flow Rate: | 6.6 mL/min |
| Standard Range: | Seven standards—1 to 500 μg/mL |

Example 4

The viscosity of aqueous solutions containing SAE-CD were measured using a cone and plate viscometer.

A Brookfield Programmable DV-III+ Rheometer, CPE-40 cone and CPE 40Y plate (Brookfield Engineering Laboratories, Middleboro, Mass.) was used to make measurements on 0.5 ml samples at 1, 2, 3, 5 and 10 rpm, Samples were sheered for approximately 5 revolutions prior to each measurement. This allowed accurate theological characterization of the samples. The temperature of all samples was equilibrated to 25+/−1 degree centigrade using a double wall viscometer cone supplied with water from an electronically controlled thermostatic circulating water bath (Model, 8001, Fisher Scientific, Pittsburgh, Pa.) The viscometer was calibrated using 5 and 50 centipoise using silicon oil calibration standards. Viscosity measurements were made at 5 or more rotation speeds to look for sheer thinning behavior (viscosities that decrease as the rate of sheer increases). Higher rotation speeds result in increased rates of sheer.

Example 5

Nebulizer output rate as a function of SAE-CD concentration was measured according to the following general procedure.

Nebulizer Output was tested using Pari LC Plus Nebulizer with a Pari ProNeb Ultra Air Compressor (Minimum Nebulizer Volume=2 ml, Maximum Nebulizer Volume=8 ml) for solutions containing 43%, 21.5%, 10.75% and 5.15% w/w SBE7-β-CD. Percentage of sample emitted was estimated gravimetrically. The nebulizer cup was weighed before and after nebulization was complete. Nebulization Time was defined as the duration of time when nebulizer run was started until the time of first sputter. Nebulizer Output Rate was calculated by dividing % Emitted with Nebulization Time.

Example 6

Preparation of an inhalable solution containing budesonide.

A buffer solution containing 3 mM Citrate Buffer and 82 mM NaCl at pH 4.45 is prepared. ~12.5 grams of CAPTISOL was placed into a 250 ml volumetric flask. ~62.5 mg of budesonide was placed into the same flask. Flask was made to volume with the 3 mM citrate buffer/82 mM NaCl solution. The flask was well-mixed on a vortexer for 10 minutes and sonicated for 10 minutes. The flask was stirred over weekend with magnetic stirrer. Stirring was stopped after ~62 hours and flask was revortexed and resonicated again for 10 minutes each. The solution was filtered through a 0.22 μm Durapore Millex-GV Millipore syringe filter unit. The first few drops were discarded before filter rest of solution into an amber glass jar with a Teflon-lined screw cap. Sample concentration was ~237 μg/ml.

Example 7

Preparation of an inhalable solution containing budesonide.

Approximately 5 grams of CAPTISOL was placed into a 100 mL volumetric flask. ~26.3 mg of budesonide was placed into the same flask. The flask was made to volume with the 3 mM citrate buffer/82 mM NaCl solution. The mixture was well-mixed on a vortexer for 10 minutes and sonicated for 10 minutes. The mixture was stirred overnight with a magnetic stirrer. Stirring was stopped after ~16 hours and flask was revortexed and resonicated again for 10 minutes each. The solution was filtered through 0.22 μm Durapore Millex-GV Millipore syringe filter unit. The first 5 drops were discarded before filter rest of solution into an amber glass jar with a Teflon-lined screw cap. Sample was analyzed to be 233 μg budesonide/ml.

Example 8

Preparation of an inhalable solution containing budesonide.

The procedure of Example 7 was followed except that 12.5 g of CAPTISOL, 62.5 mg of budesonide and about 250 ml of buffer were used. Sufficient disodium EDTA was added to prepare a solution having an EDTA concentration of about 0.01 or 0.05% wt/v EDTA.

Example 9

Preparation of a solution containing SAE-CD and budesonide as prepared from a PULMICORT RESPULES suspension.

Method A

To the contents of one or more containers of the Pulmicort Respules (nominally 2 mL of the suspension), about 50 mg (corrected for water content) of CAPTISOL was added per mL of Respule and mixed or shaken well for several minutes. After standing from about 30 minutes to several hours, the solution was used as is for in vitro characterization. In addition to budesonide and water, the PULMICORT RESPULE (suspension) also contains the following inactive ingredients per the label: citric acid, sodium citrate, sodium chloride, disodium EDTA and polysorbate 80.

Method B

Weigh approximately 200 mg amounts of CAPTISOL (corrected for water content) into 2-dram amber vials. Into each vial containing the weighed amount of CAPTISOL empty the contents of two Pulmicort Respules containers (0.5 mg/2 mL, Lot #308016 February05) by gently squeezing the deformable plastic container to the last possible drop. The Respules were previously swirled to re-suspend the budesonide particles. The vials are screw capped, mixed vigorously by vortex and then foil wrapped. The material can be kept refrigerated until use.

The inhalable liquid composition prepared according to any of these methods can be used in any known nebulizer. By converting the suspension to a liquid, an improvement in delivery of budesonide (a corticosteroid) is observed.

Example 10

Other solutions according to the invention can be prepared as detailed below.

| | Mg per ml (as prepared) | | Mg per ml |
|---|---|---|---|
| Component | Concentrate A | Concentrate B | (per target) Final Solution |
| Budesonide EP | 1 | ~1.6 (sat'd) | 0.250 |
| CAPTISOL | 200 | 200 | 50 |
| Sodium Citrate tribasic dihydrate | 0 | 0 | 0.44 |
| Citric Acid | 0 | 0 | 0.32 |
| Sodium Chloride | 0 | 0 | 4.8 |
| Disodium EDTA | 0 | 0 | 0-0.5 |
| Polysorbate 80 (Tween 80) | 0 | 0 | 0-1 |
| Water | Qs | Qs | QS with buffer containing CAPTISOL or budesonide |

Dilute Concentrate A at a ratio of 1 to 4 with pH 4.5 salinated citrate buffer (4 mM containing 109 mM sodium chloride) to contain 5% w/v CAPTISOL on an anhydrous basis. Filter the diluted concentrate through a 0.22 μm Millipore Durapore Millex-GV syringe filter unit. Assay the filtered solution by HPLC then add supplemental budesonide as needed to give a solution final concentration of about 250 μg/mL (±<5%).

Dilute Concentrate B at a ratio of 1 to 4 with pH 4.5 salinated citrate buffer (4 mM containing 109 mM sodium chloride) to contain 5% w/v CAPTISOL on an anhydrous basis. Filter the diluted concentrate through a 0.22 μm Millipore Durapore Millex-GV syringe filter unit. Assay the filtered solution by HPLC then dilute further with pH 4.5 salinated citrate buffer (3 mM containing 82 mM sodium chloride containing 5% w/v CAPTISOL) as required to give a final solution concentration of about 250 μg/mL (±<5%). This technique takes advantage of the excess solid budesonide used to saturate the solution.

Example 11

Clarity of solutions was determined by visual inspection or instrumentally. A clear solution is at least clear by visual inspection with the unaided eye.

Example 12

The following method was used to determine the performance of nebulization compositions emitted from a nebulizer according to FIGS. 10*a*-10*b*.

Two ml of the test CD solution or Pulmicort suspension was accurately pipetted by volumetric pipettes into a clean nebulizer cup prior to starting each experiment. The test nebulizer was assembled and charged with the test inhalation solution or suspension according to the manufacturer instructions. The end of the mouthpiece was placed at a height of approximately 18 cm from the platform of the MALVERN MASTERSIZER to the middle point of tip of the nebulizer mouthpiece. A vacuum source was positioned opposite the mouthpiece approximately 6 cm away to scavenge aerosol after sizing. The distance between the mouthpiece and the detector was approximately 8 cm. The center of the mouthpiece was level with the laser beam (or adjusted as appropriate, depending on the individual design of each nebulizer). The laser passed through the center of the emitted cloud when the nebulizer was running. Measurements were manually started 15 seconds into nebulization. Data collection started when beam obscuration reached 10% and was averaged over 15,000 sweeps (30 seconds). Scattered light intensity data on the detector rings was modeled using the "Standard-Wet" model. Channels 1 and 2 were killed due to low relative humidity during measurement to prevent beam steering. The volume diameter of droplets defining 10, 50 (volume median), and 90% of the cumulative volume undersize was determined. (Dv10 is the size below which 10% of the volume of material exists, Dv50 is the size below which 50% of the volume of material exists and Dv90 is the size below which 90% of the volume of material exists.

The procedure above may be practiced with slight modification on a MALVERN SPRAYTEC to determine the particle size of droplets emitted by a nebulizer.

Example 13

Solutions of budesonide with and without SBE7-β-CD were prepared at two different pHs (4 and 6) and stored at 2 different temperatures (60° C. and 80° C.). Citrate buffers (50 mM) at each pH value were prepared by mixing differing portions of 50 mM citric acid and 50 mM sodium citrate (tribasic, dihydrate) solutions. To achieve a concentration of budesonide in the buffers without SBE7-β-CD sufficient for accurate measurement, the budesonide was dissolved first in 100% ethyl alcohol. An aliquot of the ethanol/budesonide solution was then added drop-wise with stirring to each buffer solution. The theoretical budesonide concentration was 100 μg/mL with a final ethanolic content of 5% in each buffer. All solution preps and procedures involving budesonide were done in a darkened room under red light. After shaking solutions for 24 hours, both buffer solutions were filtered through Millipore Millex-GV 0.22 μm syringe filters to remove any solid that had precipitated (no significant amounts observed) from the solutions. The final budesonide concentration was about 50 μg/mL. Both the pH 4 and 6 solutions were split in two, and solid SBE7-β-CD was added to one of the portions to create solutions with and without 1% w/v SBE7-β-CD at each pH. Each solution was aliquoted into individual amber vials. They were then placed in ovens at 60° C. and 80° C. Sample vials were removed from the ovens and analyzed by HPLC at 0, 96, 164, and 288 hours. The HPLC assay conditions are summarized below.

| | |
|---|---|
| Chromatographic Conditions (Adapted from Hou, S., Hindle, M., and Byron, P. R. A. Stability-Indicating HPLC Assay Method for Budesonide. *Journal of Pharmaceutical and Biomedical Analysis*, 2001; 24: 371-380.) | |
| Instrument: | PE Series 200 |
| Column: | Phenomenex Luna C18(2) 4.6 × 150 mm 3 um |
| Mobile Phase: | 58% Phosphate Buffer pH 3.4/39.5% ACN/2.5% MeOH |
| Mobile Phase Program: | 100% A (isocratic) |
| Wavelength | 240 nm |
| Flow Rate: | 0.6 mL/min |
| Standard Range: | Seven standards—1 to 500 µg/mL |

Example 14

Preparation and use of a combination solution containing SAE-CD, budesonide, and albuterol sulfate.

A budesonide solution is prepared per EXAMPLE 9 (mixing SAE-CD with the PULMICORT RESPULES suspension) and added to 3 ml of a solution containing 2.5 mg albuterol (The World Health Organization recommended name for albuterol base is salbutamol) provided as albuterol sulfate. The albuterol solution is commercially available prediluted and sold under the name PROVENTIL® Inhalation Solution, 0.083%, or prepared from a commercially available concentrate 0.5% (sold under the names: PROVENTIL® Solution for inhalation and VENTOLIN® Inhalation Solution).

To provide the required dose for children 2 to 12 years of age, the initial dosing should be based upon body weight (0.1 to 0.15 mg/kg per dose), with subsequent dosing titrated to achieve the desired clinical response. Dosing should not exceed 2.5 mg three to four times daily by nebulization. The appropriate volume of the 0.5% inhalation solution should be diluted in sterile normal saline solution to a total volume of 3 mL prior to administration via nebulization. To provide 2.5 mg, 0.5 mL of the concentrate is diluted to 3 mL with sterile normal saline. The albuterol aqueous solutions also contain benzalkonium chloride; and sulfuric acid is used to adjust the pH to between 3 and 5. Alternatively, an aqueous solution of an appropriate strength of albuterol may be prepared from albuterol sulfate, USP with or without the added preservative benzalkonium chloride and pH adjustment using sulfuric acid may also be unnecessary when combining with the corticosteroid solution. Furthermore the volume containing the appropriate dose of corticosteroid may be decreased four-fold as described in the following example allowing the total volume to be less and the time of administration to diminish accordingly.

Example 15

Preparation and use of a combination solution containing SAE-CD, budesonide, and albuterol sulfate or levalbuterol HCl (XOPENEX).

A citrate buffer (3 mM pH 4.5) was prepared as follows. Approximately 62.5 mg of citric acid was dissolved in and brought to volume with water in one 100 ml volumetric flask. Approximately 87.7 mg of sodium citrate was dissolved in and brought to volume with water in another 100 mL volumetric flask. In a beaker the sodium citrate solution was added to the citric acid solution until the pH was approximately 4.5.

Approximately 10.4 mg of budesonide and 1247.4 mg of Captisol were ground together with a mortar and pestle and transferred to a 10 mL flask. Buffer solution was added, and the mixture was vortexed, sonicated and an additional 1.4 mg budesonide added. After shaking overnight, the solution was filtered through a 0.22 µm Durapore Millex-GV Millipore syringe filter unit. The resulting budesonide concentration was ~1 mg/ml. Approximately 0.5 ml of the budesonide solution was added to a unit dose of either Proventil (2.5 mg/3 mL) or Xopenex (1.25 mg/3 mL) thereby forming the combination clear liquid dosage form of the invention. The resulting mixture remained essentially clear for a period of at least 17 days at ambient room conditions protected from light.

Example 16

Preparation and use of a combination solution containing SAE-CD, budesonide, and formoterol (FORADIL® (formoterol fumarate inhalation powder)).

The contents of one capsule containing 12 mcg of formoterol fumarate blended with 25 mg of lactose was emptied into a vial to which was added 3-mL of 3 mM citrate buffer (pH 4.5) prepared as described in the previous example. The contents of the vial were vortexed to dissolve the solids present. The budesonide concentrate was prepared as described in the previous example to provide a concentration of ~1 mg/mL. Approximately 1 ml of the budesonide solution was added to the formoterol fumarate buffered solution. The resulting solution remained essentially clear for a period of at least one month at room ambient conditions protected from light.

Example 17

Clinical evaluation of a dosage form according to the invention was conducted by performing gamma scintigraphy analyses on subjects before and after administration of the dosage form by nebulization.

A single centre, four-way crossover gamma scintigraphy study to compare pulmonary delivery of budesonide via Pulmicort Respules®, and Captisol-Enabled® budesonide formulations using a Pari LC air-jet nebulizer was conducted. The purpose of the study was to determine, by gamma scintigraphy, the intra-pulmonary deposition of radiolabeled budesonide following nebulization of a budesonide suspension (Pulmicort Respules®, Astra Zeneca, reference formulation) and a Captisol®-Enabled budesonide solution (test formulation) in healthy male volunteers. During the course of the study, blood was collected periodically up to 24 hours, and the plasma was isolated. The concentration of budesonide in the plasma was determined using a validated HPLC MS-MS method in order to determine pharmacokinetic parameters. Dosing was conducted using a Pari LC Plus air-jet nebulizer. The use of gamma scintigraphy in conjunction with radiolabeled study drug and/or vehicle is the standard technique for the quantitative assessment of pulmonary deposition and clearance of inhaled drugs and/or vehicle.

The study dosage forms consisted of: 1) 1 mg Budesonide as 2 mL×0.5 mg/mL Pulmicort Respules®; or 2) 1 mg Budesonide as 2 mL×0.5 mg/mL Pulmicort Respules to which 7.5% w/v Captisol® has been added.

Each subject received each of four study administrations of radiolabeled Budesonide in a non-randomized manner. A non-randomized design was utilized for this study since the reference formulation (Pulmicort Respule) must be administered first to all subjects in order to determine the time to sputter (TTS). The TTS differed between subjects. For subsequent administrations the dose administered was controlled by the length of administration, expressed as a fraction of the time to sputter determined following administration of the reference formulation (i.e. 25% TTS, 50% TTS and 75% TTS). It was expected that even though the same concentration of budesonide would be nebulized for a shorter time, the amount of drug reaching the volunteers lungs would be essentially the same as the reference suspension for one of the legs of the study. Scintigraphic images were acquired using a gamma camera immediately after completion of dosing the volunteers.

Comparison of the image from the reference product and the 25% TTS leg indicated that a greater percentage of the budesonide from the Respule was in the stomach and throat immediately after administration. Thus a greater percentage of the budesonide reached the target lung tissue when Captisol was used to dissolve the budesonide. This could reduce undesirable side effects caused by the drug. One aspect of the method and dosage form of the invention thus provides an improved method of administering a corticosteroid suspension-based unit dose, the method comprising the step of adding a sufficient amount of SAE-CD to convert the suspension to a clear solution and then administering the clear solution to a subject. As a result, the method of the invention provides increased rate of administration as well as increased total pulmonary delivery of the corticosteroid as compared to the initial unit dose suspension formulation.

Example 18

Comparative evaluation of various forms of SAE-CD in the solubilization of corticosteroid derivatives.

The solubility of beclomethasone dipropionate (BDP), beclomethasone 17-monopropionate (B17P), beclomethasone 21-monopropionate (B21P) and beclomethasone (unesterifed) in solutions containing CAPTISOL and various $SBE_n\gamma$-CD was evaluated. BDP, B17P and B21P were obtained from Hovione. Beclomethasone was obtained from Spectrum Chemicals. CAPTISOL, SBE(3.4) γ-CD, SBE (5.23) γ-CD and SBE(6.1) γ-CD were provided by CyDex, Inc. (Lenexa, Kans.). γ-CD was obtained from Wacker Chemical Co. SBE(5.24) γ-CD and SBE(7.5) γ-CD were provided by the University of Kansas.

A 0.04M solution of each selected CD was prepared. Each form of beclomethasone required 2 ml of CD solution, therefore the 0.04M solutions were prepared in 20 or 25 mL volumetric flasks in duplicate (N=2). The following table indicates the amount of each CD used after accounting for the content of water in each CD.

| CD | MW (g/mole) | mg of CD (volume) |
|---|---|---|
| SBE(6.7) β-CD | 2194.6 | 2297.0 (25 ml) |
| γ-CD | 1297 | 1433.0 (25 ml) |
| SBE(3.4) γ-CD | 1834.9 | 1891.6 (25 ml) |
| SBE(5.24) γ-CD | 2119.5 | 1745.7 (20 ml) |
| SBE(6.1) γ-CD | 2261.9 | 1866.8 (20 ml) |
| SBE(7.5) γ-CD | 2483.3 | 2560.0 (25 ml) |

Beclomethasone forms were weighed in amounts in excess of the anticipated solubilities directly into 2-dram Teflon-lined screw-capped vials. These amounts typically provided approximately 6 mg/mL of solids. Each vial then received 2 ml of the appropriate CD solution. The vials were vortexed and sonicated for about 10 minutes to aid in wetting the solids with the fluid. The vials were then wrapped in aluminum foil to protect from light and placed on a lab quake for equilibration. The vials were visually inspected periodically to assure that the solids were adequately being wetted and in contact with the fluid. The time points for sampling were at 24 hrs for all samples and 72 hours for BDP only.

Solutions of SBE(6.1) γ-CD were prepared at 0.04, 0.08, and 0.1M and solutions of SBE (5.23) γ-CD were prepared at only 0.04 and 0.08M. Beclomethasone dipropionate was weighed in amounts in excess of the anticipated solubilities directly into 2-dram teflon-lined screw-capped vials. These amounts typically provided approximately 2 mg/mL of solids. Each vial then received 2 mL of the appropriate CD solution (N=1). The vials were vortexed and sonicated for about 10 minutes to aid in wetting the solids with the fluid. The vials were then wrapped in aluminum foil to protect from light and placed on a lab quake for a five-day equilibration.

Solutions of γ-CD were prepared at 0.01 and 0.02M. Beclomethasone dipropionate was weighed in amounts in excess of the anticipated solubilities directly into 2-dram teflon-lined screw-capped vials. These amounts typically provided approximately 2 mg/mL of solids. Each vial then received 2 mLs of the γ-CD solution (N=2). A solution was also prepared to measure the intrinsic solubility of BDP using HPLC grade water in place of the CD. The samples were wrapped in foil and placed on a lab quake for five days.

At the end of the equilibration time for each stage, the vials were centrifuged and 1 ml of the supernatant removed. The removed supernatant was then filtered using the Durapore PVDF 0.22 μm syringe filter (discarded first few drops), and diluted with the mobile phase to an appropriate concentration within the standard curve. The samples were then analyzed by HPLC to determine concentration of solubilized corticosteroid.

Example 19

Preparation and use of a combination solution containing SAE-CD, budesonide, and formoterol fumarate.

Formoterol fumarate dry powder is blended with Captisol dry powder which are both sized appropriately to provide for content uniformity at a weight ratio of 12 mcg formoterol fumarate/100 mg Captisol. An amount of powder blend corresponding to a unit dose of formoterol fumarate is placed in a suitable unit dose container such as a HPMC capsule for later use or is added directly to a unit dose of Pulmicort Respules budesonide inhalation suspension (500 mcg/2 mL), then mixed to achieve dissolution of all solids (a clear solution) and placed in the nebulizer reservoir for administration.

Example 20

Preparation and use of a combination solution containing SAE-CD, budesonide, and ipratropium bromide.

A budesonide solution is prepared as per EXAMPLE 9 and added to a ipratropium bromide solution that is commercially available and sold under the name ATROVENT® Inhalation Solution Unit Dose. ATROVENT® (ipratropium bromide) Inhalation Solution is 500 mcg (1 unit dose Vial) administered three to four times a day by oral nebulization, with doses 6 to 8 hours apart. ATROVENT® inhalation solution unit dose Vials contain 500 mcg ipratropium bromide anhydrous in 2.5 ml sterile, preservative-free, isotonic saline solution, pH-adjusted to 3.4 (3 to 4) with hydrochloric acid. Furthermore the volume containing the appropriate dose of corticosteroid may be decreased four-fold as described in the above example (budesonide concentrate ~1 mg/mL) allowing the total volume to be less and the time of administration to diminish accordingly.

Example 21

Evaluation of the AERONEB GO nebulizer versus a RAINDROP nebulizer with a solution comprising budesonide, aqueous liquid carrier and SAE-CD.

The AERONEB GO nebulizer (AEROGEN Inc., Mountainview, Calif.) is detailed in U.S. Pregrant Publication No. 2005-011514 to Power et al. (application U.S. Ser. No. 10/833,932 filed Apr. 27, 2004), PCT International Publication No. WO 2005/009323 to Aerogen, Inc. et al. (PCT Application No. PCT/US2004/021268 filed Jul. 6, 2004), and European Application No. EP 16426276, the entire disclosures of which are hereby incorporated by reference.

The RAINDROP nebulizer is available from Nellcor (Tyco Healthcare).

The solution of the invention used for this study was prepared according to Example 28.

Characterization of droplet size distribution of an aerosolized solution using a cascade impactor was determined according to Example 26.

Determination of total drug output and drug output rate from a nebulizer containing a liquid of the invention was determined according to Example 27.

Example 22

Evaluation of the pulsating membrane nebulizer of U.S. Pat. No. 6,962,151 with a solution comprising budesonide, aqueous liquid carrier and SAE-CD. Inertial Impaction Characterization of $Tc^{99m}$-DTPA Labelled Captisol-Enabled® Budesonide Aerosols Generated via a Pari Electronic Nebulizer The nebulizer detailed in U.S. Pat. No. 6,962,151, is also described in PCT International Application No. PCT/US00/29541 filed Oct. 27, 2000, and U.S. application Ser. No. 11/269,783 filed Nov. 7, 2005.

Aerosol characterization was conducted by standard in vitro inertial impaction tests using an Andersen Cascade Impactor (ACI). Technetium-99m ($^{99m}$Tc), in the form of diethylenetriaminepenta-acetic acid (DTPA, GE Healthcare), was added to the Captisol-Enabled® Budesonide Inhalation Solution (CEBUD). The suitability of $^{99m}$Tc-DTPA to function as a surrogate for budesonide in CEBUD preparations was validated in the course of an earlier clinical trial (see Example 17). Preparation of the budesonide solution formulation for testing was conducted as per the description below. It was calculated that approximately 10 MBq of $^{99m}$Tc should be added to the budesonide formulation (11.05 g) on the day of testing, in order to provide sufficient activity for in vitro imaging.

Two Pari electronic vibrating membrane nebulizers were used. At the core of this electronic nebulizer is a stainless steel membrane with thousands of laser drilled holes. Laser drilling allows flexibility to customize particle size, ensure reproducibility, and maintain a high output rate with smaller particles. The perforated membrane is vibrated at high frequencies in a resonant "bending" mode which yields high particle output rates. The nebulizer provides rapid drug delivery, efficiency, ideal particle sizing, low residual volume, and optimal performance matched to the inhaled drug formulation (See Rajiv Dhand, *Respiratory Care* 2002; (12): 1406-1416). Approximately 0.5 mL of drug solution was loaded and subsequently delivered via each nebulizer on 3 separate occasions. Runs 1, 3 and 5 were conducted with Device 1 and runs 2, 4 and 6 were conducted with Device 2.

Pre-Dose

On each occasion, prior to dose delivery, the filled nebulizer was imaged for 60 seconds on Head I of the dual head gamma camera (Axis, Philips Medical Systems). Also, the nebulizers were weighed before and after addition of the budesonide formulation.

Inertial Impaction Testing

The nebulizer was positioned at the USP (United States Pharmacopoeia) inlet of the ACI and a flow rate of 28.3 L/min was drawn through the impactor using a vacuum pump. Flow through the impactor was started prior to activation of the electronic nebulizer. A stopwatch was used in order to measure the duration of dose delivery.

The ACI test conditions were the same as those used for Pari LC Plus air jet nebulizer evaluation in the course of the earlier clinical study.

Following deposition the USP throat was removed from the ACI and imaged for 120 seconds. The collection plates were removed from the impactor and placed on Head I of the gamma camera and imaged for 120 seconds. The plates were subsequently washed and dried before conduct of farther impaction tests.

Post-Dose

On each occasion, the nebulizer weight was recorded after delivery of the dose. The nebulizer was imaged as described below.

Image Processing

A rectangular ROI was applied to image to the nebulizer pre-dose. This ROI was then re-applied to image the nebulizer after dose delivery.

A rectangular ROI was also applied to the USP Inlet image.

A circular ROI was drawn around collection plate 0, copied and placed around plate 1. This was repeated for plates 2-7 and the filter. A rectangular ROI was also drawn to assess the background counts. Raw counts were corrected for background activity and adjusted to counts per minute (cpm).

Aerosol performance is characterized in the table, in terms of the fine particle fraction (FPF) i.e. % emitted dose with a particle size <5.8 μm, mass median aerodynamic diameter (MMAD), geometric standard deviation (GSD) and the nebulization delivery time.

CEBUD Preparation

The expelled contents of five Pulmicort Respules (1 mg/mL) were combined together. Captisol® (165 mg) on a dried basis was added per Respule used to the combined contents of the commercial suspension to provide a Captisol concentration of about 7.5% w/v.

The mixture was vortexed briefly to disperse and dissolve the Captisol®. Then placed on a roller-bed mixer and allowed to mix for two-four or several hours. Aliquots of the equilibrated mixture were used to recover any budesonide retained in the original Respule container, and the recombined together. The mixture was the further equilibrated overnight (~20 hours) on the roller-bed mixer. After visually checking that all the suspended solids had dissolved, the required volume of 99m Tc-D5PA/saline solution (provided by Medical Physical Department, UHW) was added. So about 1800 of the Radiolabel solution was added to the Captisol-Enabled® Budesonide Inhalation Solution and vortexed briefly.

Example 23

Determination of the phase solubility curve for corticosteroid dissolution with SAE-CD.

The solubility of coritcosteroid solutions containing SAECD was determined by HPLC chromatography of aliquots from equilibrated filtered or centrifuged corticosteroid solutions as follows.

SAE-CD/steroid solutions were prepared by weighing dry solids of SAE-CD (to provide 0.04 molar) and excess steroid drug (6 mg/mL) together into a screw-capped vial. A volume of water was aliquoted to each vial (separate vial for each steroid). Intrinsic solubility was determined by weighing excess steroid (6 mg/mL) and adding a volume of water in the absence of CD. Vials were capped, initially vortexed and sonicated. Vials were then placed on a roller-mixer (model: SRT2; Manufacturer: Stuart Scientific; Serial number: R000100052) or rocker/mixer (Model: LabQuake; Manufacturer: Barnstead/Thermolyne; Serial number: 1104010438202). Higher excesses of solid steroid (up to 10 mg/mL) were then added to any vial where the liquid contents clarified overnight (e.g. prednisolone, hydrocortisone, and prednisone). Samples were rolled and mixed on the roller or rocker for 72 hours. At various times during the equilibration, samples were additionally vortexed or sonicated briefly (up to 30 minutes). After the designated equilibration time, samples were filtered (0.22 µm, 25 mm, Duropore—PVDF, manufacturer: Millipore) into clean vials except for the intrinsic solubility sample for Beclomethasone Dipropionate which was centrifuged and the supernatant transferred to a clean vial. Samples were analyzed by conventional HPLC methods.

Example 24

Preparation of clear liquid formulations containing SAE-CD, budesonide and Salmeterol xinafoate. A formulation of this kind can be prepared according to other examples herein containing a combination of corticosteroid, SAE-CD and a second therapeutic agent.

Example 25

Preparation of clear liquid formulations containing SAE-CD, budesonide and albuterol sulfate.

A stock solution containing CAPTISOL (40.0 g), water (1 L), citric acid (387.6 mg), sodium citrate (519.6 mg), EDTA (120 mg), and NaCl (6.36 mg) was prepared by mixing the components together.

Budesonide (37.5 mg) and albuterol sulfate (150 mg) were added to an aliquot (150 ml) of the stock solution and mixed on a roller mixer at ambient temperature until dissolution of all components. The final solution was clear, however, it could be filtered if needed. The final concentration of components in the formulation was as follows: CAPTISOL (0.018 M); budesonide (5.9 mM or 254 µg/ml); and albuterol sulfate (1 mg/ml).

Example 26

Characterization of droplet size distribution of an aerosolized solution using a cascade impactor.

The droplet size distribution of an aerosolized solution of the invention was characterized using an NGI cascade impactor. Approximately 0.5 mL of the 1000 µg/mL was placed into a nebulizer, such as the AERONEB GO. The vacuum pump associated with the impactor was turn on. The nebulizer mouthpiece was positioned into the center of the USP induction port and sealed to it with parafilm. The nebulizer was turned on until no more vapors were visible. Collection continued for an additional 45 seconds to ensure complete collection of the sample. Vacuum was turned off and the impactor disassembled. The collection cups at each stage were extracted with known volumes of HPLC mobile phase and assayed for budesonide. The cumulative amount of budesonide on each stage was quantified. The percent of drug exiting the nebulizer was 81%, and the percent of drug in the fine particle fraction (<5 µm) was 66%.

Example 27

Determination of total drug output and drug output rate from a nebulizer containing a liquid of the invention.

A dose collection apparatus was constructed with a 300 ml glass filter unit of the type used to filter HPLC mobile phases. A specially fabricated Plexiglas lid covered the reservoir and had an opening to admit aerosol into the reservoir. The reservoir tapered towards a glass fiber filter supported by a metal mesh. The mesh was contained in a conical glass housing that terminated in a glass tube, which was attached to a flow controller and vacuum pump. The reservoir and filter support housing were clamped together. Two filters were sandwiched together in the apparatus to collect the emitted aerosol. This was necessary to avoid saturation of the filter, which can result in it tearing with subsequent drug loss into the vacuum, and changes in airflow rate over the course of aerosol collection. The end of nebulization was judged by intermittent aerosol output and/or a change in pitch of the nebulizer sound. To prevent loss of nebulized budesonide to the atmosphere, air was drawn into the filter faster than it was ejected from the nebulizers. By visually confirming that no aerosol escaped from the back of any nebulizer, a flow rate of 15±5% l/min was deemed satisfactory. This was regulated by a TPK flow controller (Copley Instruments, 4312) and vacuum pump, and confirmed before each experiment using a calibrated flow meter.

Example 28

Preparation of a liquid formulation comprising SAE-CD and hudesonide, optionally containing Tween.

A 3 mM citrate buffer at pH 4.5 was added to 2 grams of CAPTISOL and 25 mg of budesonide in a serum vial to make the final volume 10 mL. The suspension was well mixed by vortexing and sonication. A 20% stock solution of CAPTISOL without budesonide was also prepared in 3 mM citrate buffer. These mixtures, along with the buffer were sealed in separate vials and autoclaved using the 20-minute hold at 121° C. cycle. HPLC analysis of the clear budesonide solution showed the concentration was 2100 µg/mL. The 20% CAPTISOL stock solution was used to dilute the sample to 2000 µg/mL. A portion of the above resulting solution was optionally diluted with an equal volume of the 3 mM citrate buffer. HPLC analysis showed the final concentration was 990 µg of budesonide/mL.

The Tween could be added to the above solution as follows. A solution of 0.02% Tween was prepared with the autoclaved buffer only solution to form a Tween stock solution for use as a diluent for the above solutions. The dilutions for the 10% captisol/1 mg/mL budesonide were done by weight. Approximately 9 grams of the 20% captsiol/2000 µg/mL was mixed with ~9 grams of either the autoclaved buffer only solution or the autoclaved buffer/0.02% Tween solution. These solutions were well-mixed, filtered and reassayed by HPLC.

The hudesonide concentrations of the above formulations were found to be 986 μg/mL for the solution without Tween and 962 μg/mL for the solution with Tween.

The solutions can be nebulized with any nebulizer; however, with an AERx nebulizer, an initial sample volume of 50 μl can be used. Administration of this solution with the nebulizer makes it feasible for a therapeutic dose to be administered to a subject in a single puff (a single full inhalation by a subject) via nebulization.

Example 29

Preparation and dissolution of a lyophilized formulation comprising SAE-CD and budesonide.

An excess of budesonide, 3.5 mg/mL, was added to 3 L of 30% Captisol in 3 mM citrate buffer containing 0.1 mg/mL EDTA. After mixing for 2 days, an additional 1 mg/mL budesonide was added and equilibrated an additional 4 days. The preparation was filtered through a 0.22μ Duropore filter and placed in three stainless steel trays in a freeze dryer. The solution was frozen at −30° C. for one hour and lyophilized over 30 hours to remove essentially all the water. The lyophile was powdered, screened and the powder transferred to a plastic bottle. The final composition contained 8.2 mg budesonide per gram of powder.

When approximately 65 mg of powder was added to 2 mL of water, an essentially clear solution containing the same amount of budesonide as in the reference suspension product was rapidly obtained.

Example 30

Preparation of an aqueous liquid formulation comprising SAE-CD, ethanol and budesonide.

Captisol/Ethanol solutions were prepared by making a stock captisol solution at 22.2% (~0.1M) w/v which was diluted with either ethanol or water in varying amounts to create four solutions of 0, 1, 2, 5% ethanol and about 20% w/v Captisol. Captisol/Ethanol/Budesonide solutions were prepared by adding dry Budesonide (2.5 mg/mL) to a volume of the prepared Captisol/ethanol solutions and then these were equilibrated on a Labquake for 72 hours. These solutions were filtered (Duropore syringe filters) and analyzed by HPLC to determine the concentration (μg/ml) of budesonide dissolved in the formulation.

Example 31

An in-vivo evaluation of a dosage form according to the invention was conducted by performing a pharmacokinetic analysis on budesonide after administration of the dosage form by nebulization.

A four dog crossover study to compare pulmonary delivery of budesonide via Pulmicort Respules®, and a Captisol-Enabled® budesonide formulation using a Pari LC air-jet nebulizer was conducted. The purpose of the study was to determine, by HPLC-MS/MS analysis, the pharmacokinetics of budesonide the plasma, following nebulization of a budesonide suspension (Pulmicort Respules®, AstraZeneca, reference formulation) and a Captisol-Enabled® budesonide inhalation solution (test formulation) in healthy dogs. Dosing was conducted using a Pari LC Star air-jet nebulizer and anesthesia masks.

The study dosage forms consisted of: 1) 1 mg Budesonide as two 2 mL×0.25 mg/mL Pulmicort Respules®; or 2) 1 mg Budesonide as two 2 mL×0.25 mg/mL Pulmicort Respules to which 5% w/v Captisol® was added.

Prior to dosing, two capsules containing activated charcoal followed with approximately 30 mL of water were administered to each dog to block oral absorption of the budesonide. Each dog received each of the study administrations one week apart in a randomized manner. Administration time was the same for each formulation (23.9 min. for test formulation and 23.4 min. for reference). Blood was collected periodically up to 8 hours, the plasma was isolated and stored at −70° C. until analysis. After each administration, the nebulizer and test solution container were assayed for residual budesonide to determine the amount of drug delivered.

Example 32

To investigate how the incorporation of Captisol at 5% w/v into Pulmicort Respules impact performance of different types of nebulizers.

The emitted dose of budesonide from four different nebulizers (PARI LC PLUS (air jet), OMRON MICROAIR NE-U22, AIRSEP MYSTIQUE (ultrasonic), AEROGEN AERONEB) was determined. The package insert-approved Pari air jet system was used as the benchmark to judge performance of the other nebulizers. The emitted dose was from 1.25 to 3.7 times higher when Captisol was added to the budesonide suspension. The Emitted dose (ED) was determined by:

1) Drawing the nebulized formulations through a 300 mL glass filter apparatus at 15 l/min, and collecting drug on double or triple layers of glass fiber depth filter and the interior walls. Collection was stopped every two minutes, the budesonide quantitatively recovered, and filters were changed to prevent filter saturation or alterations in airflow. Budesonide recovery was quantified by HPLC; and/or
2) Summing the amount of budesonide on the cascade impactor stages after nebulization.

The results are detailed below. (ND means "not determined.")

| Formulation | Total Delivered (ED) (μg, mean & SD), Filter[1] | Total Delivered (ED) (μg, mean & SD), Impactor[2] |
|---|---|---|
| Pari LC Plus (Air Jet) Listed in the Pulmicort package insert | | |
| Pulmicort | 171.5 ± 6.3 | 137.8 ± 14.9 |
| Pulmicort + 5% Captisol | 247.4 ± 11.3 | 172.4 ± 6.6 |
| Omron MicroAir NE-U22 | | |
| Pulmicort | 179.9 ± 17.2 | 168.8 ± 30.1 |
| Pulmicort + 5% Captisol | 380.1 ± 8.5 | 349.6 ± 10.0 |
| AirSep Mystique (Ultrasonic) | | |
| Pulmicort | 32.9 ± 6.4 | ND* |
| Pulmicort + 5% Captisol | 120.8 ± 19.6 | ND* |
| Aerogen AeroNeb | | |
| Pulmicort | 90.7 ± 4.5 | ND* |
| Pulmicort + 5% Captisol | 301.2 ± 19.5 | ND* |

All documents cited herein are each incorporated by reference herein in its entirety. The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method of treating a disease or disorder of the airways in a subject in need thereof, comprising administering via pulmonary inhalation to the subject an aqueous liquid formulation comprising an aqueous liquid carrier, a sulfoalkyl ether cyclodextrin (SAE-CD), and a dose of corticosteroid dissolved therein, wherein i. the SAE-CD has the structure:

[chemical structure of cyclodextrin with ROCH$_2$ and OR substituents, CH$_2$OR groups]

wherein:
each R is independently —H or —(CH$_2$)$_4$SO$_3$Na;
wherein the average degree of substitution of —(CH$_2$)$_4$SO$_3$Na is 6.0 to 7.1 per cyclodextrin molecule;
ii. the corticosteroid is budesonide; and
iii. the formulation provides an enhanced pharmacokinetic profile over a suspension based formulation administered under similar conditions, wherein the molar ratio of SAE-CD to corticosteroid is greater than 10:1, and wherein more than 50 % by weight of the corticosteroid is complexed with the SAE-CD.

2. The method of claim 1, wherein the formulation is administered with a nebulizer selected from the group consisting of an air jet nebulizer, ultrasonic nebulizer, electronic nebulizer, vibrating membrane nebulizer, vibrating mesh nebulizer, and a vibrating plate nebulizer.

3. A method of treating a disease or disorder of the airways in a subject in need thereof, comprising administering via pulmonary inhalation to the subject an aqueous liquid formulation comprising an aqueous liquid carrier, a sulfoalkyl ether cyclodextrin (SAE-CD), and a dose of corticosteroid dissolved therein, wherein i. the SAE-CD has the structure:

[chemical structure of cyclodextrin with ROCH$_2$ and OR substituents, CH$_2$OR groups]

wherein:
each R is independently —H or —(CH$_2$)$_4$SO$_3$Na;
wherein the average degree of substitution of —(CH$_2$)$_4$SO$_3$Na is 6.0 to 7.1 per cyclodextrin molecule;
ii. the corticosteroid is budesonide; and
iii. the formulation provides an enhanced pharmacokinetic profile over a suspension based formulation administered under similar conditions, wherein the molar ratio of SAE-CD to corticosteroid is greater than 10:1, wherein more than 50% by weight of the corticosteroid is complexed with the SAE-CD, and wherein the formulation comprises nebulized droplets having a particle size of 0.5 to 5 microns.

* * * * *